(12) United States Patent
Tanner et al.

(10) Patent No.: US 7,455,995 B2
(45) Date of Patent: Nov. 25, 2008

(54) BAALC EXPRESSION AS A DIAGNOSTIC MARKER FOR ACUTE LEUKEMIA

(75) Inventors: Stephan Markus Tanner, Columbus, OH (US); Albert de la Chapelle, Delaware, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 705 days.

(21) Appl. No.: 10/293,239

(22) Filed: Nov. 12, 2002

(65) Prior Publication Data

US 2003/0119043 A1 Jun. 26, 2003

Related U.S. Application Data

(60) Provisional application No. 60/348,210, filed on Nov. 9, 2001.

(51) Int. Cl.
  *C12P 19/34* (2006.01)
  *C12Q 1/68* (2006.01)
(52) U.S. Cl. .................. 435/91.2; 435/91.21; 435/6
(58) Field of Classification Search ................ 435/6
See application file for complete search history.

(56) References Cited

FOREIGN PATENT DOCUMENTS

WO WO 03/040347 5/2003

OTHER PUBLICATIONS

International Search Report dated Aug. 23, 2004.
"Involvement of BAALC, a novel gene, in hematopoiesis and acute leukemia" by Tanner, et al., *Blood*, (Nov. 16, 2001) vol. 98, No. 11, Part 1, pp. 800a-801a.
"Overexpression of BAALC suppresses normal hematopoiesis" by Baldus, et al., *Blood*, vol. 100, No. 11, Abstract No. 4147, Nov. 16, 2001.
"BAALC, the human member of a novel mammalian neuroectoderm gene lineage, is implicated in hematopoiesis and acute leukemia" by Tanner, et al., *PNAS*, Nov. 20, 2001, vol. 98, No. 24, pp. 13901-13906.
Abstract P-300, "Gene expression in acute myeloid leukemia with trisomy 8" by Tanner, et al., 21st Annual Meeting of the European Society of Human Genetics, Geneva, Switzerland, May 29-Jun. 1, 1999.
Abstract 18434, "Novel gene in Acute Myeloid Leukemia with Trisomy 8" by Tanner, et al, *The American Journal of Human Genetics*, vol. 65, No. 4, Oct. 1999.
Abstract 3330, "Involvement of *BAALC*, a Novel Human Gene, in Hematopoiessi and Acute Leukemia" by Tanner, et al., Forty-third Annual Meeting of the American Society of Hematology, Orlando, Florida, Dec. 7-11, 2001.
Abstract LB-138, "Expression of *BAALC* predicts adverse prognosis in adult *de novo* acute myeloid leukemia (AML) with normal cytogenetics: A Cancer and Leukemia Group B (CALGB) Study" by Tanner, et al., 93rd Annual Meeting of the American Association for Cancer Research, San Francisco, California, Apr. 6-10, 2002.
GenBank Accession No. AA400649 (submitted Apr. 28, 1997).
GenBank Accession No. AC025370 (submitted Feb. 20, 2002).
GenBank Accession No. AC025936 (submitted May 27, 2001).
GenBank Accession No. AF363578 (submitted Mar. 22, 2001).
GenBank Accession No. AF371319 (submitted Apr. 17, 2001).
GenBank Accession No. AF371320 (submitted Apr. 17, 2001).
GenBank Accession No. AF371321 (submitted Apr. 17, 2001).
GenBank Accession No. AF371322 (submitted Apr. 17, 2001).
GenBank Accession No. AF371323 (submitted Apr. 17, 2001).
GenBank Accession No. AF371324 (submitted Apr. 17, 2001).
GenBank Accession No. AF371325 (submitted Apr. 17, 2001).
GenBank Accession No. AF371326 (submitted Apr. 17, 2001).
GenBank Accession No. BF 190130 (submitted Nov. 2, 2000).
GenBank Accession No. BF192691 (submitted Nov. 2, 2000).
GenBank Accession No. AB073318 (submitted Oct. 19, 2001).
Wang et al., "BAALC 1-6-8 protein is targeted to postsynaptic lipid rafts by its N-terminal myristoylation and palmitoylation, and interacts with $\alpha$, but not $\beta$, subunit of Ca2+/calmodulin-dependent protein kinase II," J. of Neurochemistry, 92, 647-659 (2005).

*Primary Examiner*—Gary Benzion
*Assistant Examiner*—Cynthia Wilder
(74) *Attorney, Agent, or Firm*—Calfee, Halter & Griswold LLP

(57) ABSTRACT

Overexpression of the gene, BAALC, in biological samples from a patient is prognostic for tumor aggressiveness and unfavorable patient outcome. The present invention provides polynucleotide primers and probes for assaying for overexpression of BAALC transcripts. Kits containing the primers and probes are also provided. Also provided are antibodies for assaying for overexpression of BAALC proteins as well as peptide immunogens for producing the anti-BAALC antibodies. The present invention also provides methods for characterizing acute myelogenous leukemia, chronic myelogenous leukemia and prostate cancer in a patient, base on detection of BAALC overexpression.

11 Claims, 16 Drawing Sheets

*BAALC* human exons:

Exon 1
gagagggcccggactaggggcggcgggcaccgcaggagctccgcgcggctgcagcgcgggcgggagcggggacgcgatgt
cgccgccgccgcctccttgcgggccggggctgcgcctccggggctgagccgccgccagagccgacagccgagcagccgct
gggcgctcccgcggcgcaggaggATGGGCTGCGGCGGGAGCCGGGCGGATGCCATCGAGCCCCGCTACTACGAGAGCTGG
ACCCGGGAGACAGAATCCACCTGGCTCACCTACACCGACTCGGACGCGCCGCCCAGCGCCGCCGCSCCGGACAGCGGCCC
CGAAGCGGGCGGCCTGCACTCGG Exon 2
CCCATTACCCTCTTGCCTTTGCACTTGCCTGGAGAGACAACAGTTTAGGGGCTCTGCTGGTTCAAGAAGGACTGTGCAGG
TAGCATGGCCACACACCATGTACAG Exon 3
GTTCTGGTGCTTAGGAGTGGACATCTTTGGGACCGAGGGTTATTCTGCCTTCCTACCATGTCACCAGAGTTGTGCTAATA
CACAGAGAGCTTCAGGGGATGAGATCTGCCATTCATTGAGCACCTTCTGTGCGGCAGACAGTGTTAG Exon 4
GGTGCCTTGAGGAACATTACCATCTGACTGCCCTACAGAAAGTTGGGCATCCCAACCATTGATTTAAAAAG Exon 5
TTCTGGAGGCTGAGAAGTCCAAGATCAAGGCACCAACAGATTCAGTGTCTGATGAAGGCTTGTTCTCTGCTTCAAAGATG
GCACCTCTTGCTGTGTTCTCACATG Exon 6
GCATGCTGGAAGATGGACTGCCCTCCAATGGTGTGCCCCGATCTACAGCCCCAGGTGGAATACCCAACCCAGAGAAGAAG
ACGAACTGTGAGACCCAGTGCCCAAATCCCCAGAGCCTCAGCTCAGGCCCTCTGACCCAGAAACAGAATGGCCTTCAGAC
CACAGAG Exon 7
GTTCTGCTGCCTTCCTAATGTCTGATCTTCTATCTGAAGTTCAAGTTGAAAAGCAACAACTCCTTTTGGCACTCGATACA
AACTCCCAGC Exon 8
GCTAAAAGAGATGCTAAGAGAATGCCTGCAAAAGAAGTCACCATTAATGTAACAGATAGCATCCAACAGATGGACAGAAG
TCGAAGAATCACAAAGAACTGTGTCAACTAGcagagagtccaagcagaagggcagatggacttcttcagtgtccttcacg
gcactggatcccatcaaagaaccttgaagaagtggctgccccttgctggacctgaattctactgagtccctggcaagact
gtcttacctggcagcaaactgctgcctgatttgttgggaccttctgagccttctacttatcatgtaaatgtattggcaca
gtgcttacatatgttAATAAActgcaaatgtgcagttcagtttgtctctttgcaactcctgtaatacggtctggtgtaaa
agtagtgagttaaagctacaggtcagtttatgaaacagaaaagtaggaatgcattttctgggtgaaagagtcacaccta
gtgctataactctcctgcccatgatagtgtattctgtttcaggcaagcttattctttccttctttcattttaaatattgt
cattacaaatcttaccaggttcacttaaaagctggctttcatccaactctaaacccacatattgaaaaaatcaaggtaca
ggaaaactccttgttatccttgtttccttagcttggtatgagacagatcggatccagtttcccatgcaccaacccactgc
ccatggcatgtctttgggaggtgtctgtgaagcagtcatacctgctcctcatctgcctggaaagtcctcctattccagtg
tccatgttggcctccagtccttaatgtcaccatgcttgtggccaatgcatccaaataaggataccccttcagggctcagct
agacattgcaattttgcatagcttccagttccctttgcttgtcttcttgactgtcttccctctctatcggggtcacttg
caattgttaatcaaagattgaacactgcgtaggagagggagatgatccagagacatgtggcagcaggcatggcttcccct
tggcctctctgtacactgccccaggactgtcattttggcatctgcaaaggaatcactttagaaagccagcacctggttga
tgtgtattcatactgacattagattgatgtgcactgcattagaaatgaggtagctgacacagaaaaaggatgttttgata
ggaataattttctagtatgtcttgaaacatgttcatctggaagtattttcctccaaagtaatgtagcatgattttttcaag
gattgttaacatgcctgggattgggaaagataggactaaagttgtgccaaactatatcAATAAAttccatgtttagcaga
aataggcagcctattggtgttatgtttatgtaacatagtccagagaactgacatgcaggtcaaaagtcagatacgcaacc
tccttatctgctaactctgttattcttcaaacacaacgtgggtagtgtcatttttccttccttccttccattggcagatt
gtatatttattcacaaaacattaaatgtccatcctgtgccaggtactatgcagatgttgagggatttggggtctggttag
tcgtgactatctatcctgaatctaacagtgacttcataactaggagactgaattagacccttaaggtatagtgtgtgttg
caaatcactctgcaatggaaactttatattcagggtaggtttgtgtcttaaactaggtgttctaatcaatgtacaagac
ttaccatacacgcaactatagtttttctaaaccttcatcatttgtgattctttgagaaagggcttttaggaactttat
gttctaaaaaatgtttttaacaataataagataaaagaaaaaacctgtgattcatatgtccccactggcattactcagcag
gagcccccagctgccaaaggttggcagtgatcctgcaagttcaagggctctttctccctggggatgtgctttgtggcttc
tctttacagctttgtttctgcatcagttcactgctgcatgttgtttggaatttatcaccttaagaaagtgtctctgttt
atatagaaacactttctcacttacaggggagaaggaaatgcagggcacatgatctggccctccccagaacaatctggatt
tcacggagacagcaaccagaagttaaaccatgtgactaaaaatgcatctggctacttttcatgtatgtatgagacagaa
actaatccttactatcctattaggataccacttttcattgcaaagtttgtgtcAATAAAgtcattaattttaaacat

Fig. 2

1-6-8
gagagggccggacuagggcggcgggcaccgcaggagcuccgcgcggcugcagcgcgggcgggagcggggacgc
gaugucgccgccgccgccuccuugcgggccggggcugcgccuccggggcugagccgccgccagagccgacagccg
agcagccgcugggcgcuccgcggcgcaggaggAUGGGCUGCGGCGGGAGCCGGGCGGAUGCCAUCGAGCCCCGC
UACUACGAGAGCUGGACCCGGGAGACAGAAUCCACCUGGCUCACCUACACCGACUCGGACGCGCCGCCCAGCGCC
GCCGCSCCGGACAGCGGCCCCGAAGCGGGCGGCCUGCACUCGGGCAUGCUGGAAGAUGGACUGCCCUCCAAUGGU
GUGCCCCGAUCUACAGCCCCAGGUGGAAUACCCAACCCAGAGAAGAAGACGAACUGUGAGACCCAGUGCCCAAAU
CCCCAGAGCCUCAGCUCAGGCCCUCUGACCCAGAAACAGAAUGGCCUUCAGACCACAGAGGCUAAAAGAGAUGCU
AAGAGAAUGCCUGCAAAAGAAGUCACCAUUAAUGUAACAGAUAGCAUCCAACAGAUGGACAGAAGUCGAAGAAUC
ACAAAGAACUGUGUCAACUAGcagagaguccaagcagaagggcagauggacuucuucagugccuucacggcacu
ggaucccaucaaagaaccuugaagaaguggcugccccuugcuggaccugaauucuacugaguccuggcaagacu
gucuuaccuggcagcaaacugcugccugauuuguugggaccuucugagccuucuacuuaucauguaaauguauug
gcacagugcuuacauauguuAAUAAAcugcaaaugugcaguucaguuugucucuuugcaacuccuguaauacggu
cuggugugaaaaguagugaguuaaagcuacaggucaguuuaugaaacagaaaaguaggaaugcauuuucggguga
aagagucacaccuuagugcuauaacucuccugcccaugauagguauucuguuucaggcaagcuuauucuuuccu
ucuuucauuuaaauauugucauuacaaaucuuaccagguucacuuaaaagcuggcuuucauccaacucuaaacc
cacauauugaaaaaaucaagguacaggaaaacuccuuguuauccuuguuuccuuagcuugguaugagacagaucg
gauccaguuucccaugcaccaacccacugcccauggcaugucuuugggaggugucugugaagcagucauaccugc
uccucaucugccuggaaaguccuccuauuccagugccauguuggccuccaguccuuaaugucaccaugcuugug
gccaaugcauccaaauaaggauaccccucagggcucagcuagacauugcaauuuugcauagcuuuccaguuccu
uugcuugucuuucuugacugucuucccucucuaucggggucacuugcaauuuuaaucaaagauugaacacugcgua
ggagagggagaugauccagagacauguggcagcaggcauggcuuccccuuggccucucuguacacugcccagga
cugucauuuuggcaucugcaaaggaaucacuuuagaaagccagcaccugguugauguguauucauacugacauua
gauugaugugcacugcauuagaaaugagguagcugacacagaaaaaggauguuuugauaggaauaauuuucuagu
augucuugaaacauguucaucuggaaguauuuuccuccaaaguaauguagcaugauuuucaaggauuguuaaca
ugccugggauugggaaagauaggacuaaaguugugccaaacuauauCAAUAAAuuccauguuuagcagaaauagg
cagccuauugguguauguuuauguaacauagucccagagaacugacaugcaggucaaaagucagauacgcaaccu
ccuuaucugcuaacucuguuauucuucaaacacaacguggguaguugucauuuuuccuuccuuccuuccauugca
gauuguauauuuauucacaaaacauuaaaugccauccugugccagguacuaugcagaugaugaugggaauugggg
ucugguuagucgugacuaucuauccugaaucuaacagugacuucauaacuaggagacugaauuagacccuuaagg
uauagugugguuugcaaaucacucugcaauggaaacuuuuauauucagggauggauuugugucuuaaacuaggugu
ucuaaucaauguacaagacuuuaccauacacgcaacuauaguuuuucuaaaccuucaucauuuugugauucuuug
agaaagggcuuuuaggaacuuuauguucuaaaaaauguuuuuaacaauaauaagauaaaagaaaaaccugugauu
cauaugucccccacuggcauuacucagcaggagccccagcugccaaaggguuggcagugauccugcaaguucaagg
gcucuuucuccoggggaugugcuuugugggcuucucuuuacagcuuuguuucugcaucaguucacugcugcaugu
uguuuggaauuuaucaccuuaagaaagugucucuguuuauauagaaacacuuucucacuuacaggggagaagga
aaugcagggcacaugaucuggcccuccccagaacaaucuggauuucacggagacagcaaccagaaguuaaaccau
gugacuaaaaaugcaucuggcuacuuuuucauguauguaugagacagaaacuaauccuuacuauccauuaggau
accacuuuucauugcaaaguuuguguCAAUAAAgucauuaauuuuaaacau

Fig. 5

1-8
gagagggcccggacuaggggcggcgggcaccgcaggagcuccgcgcggcugcagcgcgggcgggagcgggg
acgcgaugucgccgccgccgccuccuugcgggccggggcugcgccuccggggcugagccgccgccagagcc
gacagccgagcagccgcugggcgcucccgcggcgcaggaggAUGGGCUGCGGCGGGAGCCGGGCGGAUGCC
AUCGAGCCCCGCUACUACGAGAGCUGGACCCGGGAGACAGAAUCCACCUGGCUCACCUACACCGACUCGGA
CGCGCCGCCCAGCGCCGCCGCSCCGGACAGCGGCCCCGAAGCGGGCGGCCUGCACUCGGGCUAAAAGAGAU
GCUAAGAGAAUGCCUGCAAAAGAAGUCACCAUUAAUGUAACAGAUAGCAUCCAACAGAUGGACAGAAGUCG
AAGAAUCACAAAGAACUGUGUCAACUAGcagagaguccaagcagaagggcagauggacuucuucagugucc
uucacggcacuggaucccaucaaagaaccuugaagaaguggcugccccuugcuggaccugaauucuacuga
gucccuggcaagacugucuuaccuggcagcaaacugcugccugauuuguugggaccuucugagccuucuac
uuaucauguaaauguauuggcacagugcuuacauauguuAAUAAAcugcaaaugugcaguucaguuugucu
cuuugcaacuccuguaauacggucugguguaaaaguagugaguuaaagcuacaggucaguuuaugaaacag
aaaaguaggaaugcauuucugggugaaagagucacaccuuagugcuauaacucuccugccaugauagug
uauucuguuucaggcaagcuuauucuuuccuucuuucauuuaaauauugucauuacaaaucuuaccaggu
ucacuuaaaagcuggcuuucauccaacucuaaacccacauauugaaaaaaucaagguacaggaaaacuccu
uguuauccuuguuuccuuagcuugguaugagacagaucggauccaguucccaugcaccaacccacugccc
auggcaugucuuugggaggugucugugaagcagucauaccugcuccucaucugccuggaaaguccuccuau
uccagugucccauguuggccuccaguccuuaaugucaccaugcuuguggccaaugcauccaaauaaggauac
cccucagggcucagcuagacauugcaauuuugcauagcuuuccaguucccuuugcuugucuucuugacugu
cuucccucucuaucggggucacuugcaauuguuaaucaaagauugaacacugcguaggagagggagaugau
ccagagacauguggcagcaggcauggcuucccuuggccucucuguacacugcccaggacugucauuuug
gcaucugcaaaggaaucacuuuagaaagccagcaccugguugaugcguauucauacugacauuagauugau
gugcacugcauuagaaaugagguagcugacacagaaaaggauguuuugauaggaauaauuuucuaguaug
ucuugaaacauguucaucuggaaguauuuccuccaaaguaauguagcaugauuuucaaggauuguuaac
augccugggauugggaaagauaggacuaaaguugugccaaacuauaucAAUAAAuccauguuuagcagaa
auaggcagccuauugguguuauguuuauguaacauaguccagagaacugacaugcaggucaaaagucagau
acgcaaccuccuuaucugcuaacucuguuauucuucaaacacaacgugggguagugucauuuuuccuuccuu
ccuuccauuggcagauuguauauuuauucacaaaacauuaaaugucccauccugugccagguacuaugcaga
uguugagggauuuggggucugguuagucgugacuaucuauccugaaucuaacagugacuucauaacuagga
gacugaauuagacccuuaagguauagugugugüugcaaaucacucugcaauggaaacuuuuauauucaggg
uaggüuugugucuuaaaacuaggüguuucuaaucaauguacaagacuuuaccauacacgcaacuauaguuuuu
cuaaaccuucaucauuuugugauucuuugagaaagggcuuuuaggaacuuuauguucuaaaaaauguuuuu
aacaauaauaagauaaaagaaaaaccugugauucauaugucccacuggcauuacucagcaggagccccca
gcugccaaagguuggcagugauccugcaaguucaagggcucuuucucccuggggaugugcuuuguggcuuc
ucuuuacagcuuuguucugcaucaguucacugcugcauguuguuggaauuuaucaccuuaagaaagugu
cucuguuuuauauagaaacacuuucucacuuacaggggagaaggaaaugcagggcacaugaucuggcccuc
cccagaacaaucuggauuucacggagacagcaaccagaaguuaaaccaugugacuaaaaaugcaucggcu
acuuuuucauguauguaugagacagaaacuaauccuuacuauccuauuaggauaccacuuuucauugcaaa
guuugugucAAUAAAgucauuaauuuuaaacau

Fig. 6

1-5-6-8 gagagggcccggacuaggggcggcgggcaccgcaggagcuccgcgcggcugcagcgcgggcgggagcggggac
gcgaugucgccgccgccgccuccuugcgggccggggcugcgccuccggggcugagccgccgccagagccgaca
gccgagcagccgcugggcgcucccgcggcgcaggaggAUGGGCUGCGGCGGGAGCCGGGCGGAUGCCAUCGAG
CCCCGCUACUACGAGAGCUGGACCCGGGAGACAGAAUCCACCUGGCUCACCUACACCGACUCGGACGCGCCGC
CCAGCGCCGCCGCSCCGGACAGCGGCCCCGAAGCGGGCGGCCUGCACUCGGUUCUGGAGGCUGAGAAGUCCAA
GAUCAAGGCACCAACAGAUUCAGUGUCUGAUGAAGGCUUGUUCUCUGCUUCAAAGAUGGCACCUCUUGCUGUG
UUCUCACAUGGCAUGCUGGAAGAUGGACUGCCCUCCAAUGGUGUGCCCCGAUCUACAGCCCCAGGUGGAAUAC
CCAACCCAGAGAAGAAGACGAACUGUGAGACCCAGUGCCCAAAUCCCCAGAGCCUCAGCUCAGGCCCUCUGAC
CCAGAAACAGAAUGGCCUUCAGACCACAGAGGCUAAAAGAGAUGCUAAGAGAAUGCCUGCAAAAGAAGUCACC
AUUAAUGUAACAGAUAGCAUCCAACAGAUGGACAGAAGUCGAAGAAUCACAAAGAACUGUGUCAACUAGcaga
gaguccaagcagaagggcagauggacuucuucagugu ccuucacggcacuggaucccaucaaagaaccuugaa
gaaguggcugcccuugcuggaccugaauucuacugagucccuggcaagacugucuuaccuggcagcaaacug
cugccugauuuguugggaccuucugagccuucacuuaucauguaaauguauuggcacagugcuuacauaugu
uAAUAAAcugcaaauguagcaguucaguuugucucuuugcaacuccuguaauacggucuggguaaaaguagug
aguuaaagcuacaggucaguuuaugaaacagaaaaguaggaaugcauuuucggggugaaagagucacaccuua
gugcuauaacucuccugcccaugauagug uauucuguuucaggcaagcuuauucuuuccuucuuucauuuuaa
auauugucauuacaaaucuuaccagguucacuuaaaagcuggcuuucauccaacucuaaacccacauauugaa
aaaaucaaggucaggaaaacucccuuguuauccuuguuuccuuagcugguaugagacagaucggauccaguu
ucccaugcaccaacccacugcccauggcaugucuuugggaggugucugugaagcagucauaccugcuccucau
cugccuggaaagucucccauuccagugcccauguuggccuccaguccuuaaugucaccaugcuuguggccaa
ugcauccaaauaaggauacccucagggcucagcuagacauugcaauuugcauagcuuccaguucccuuug
cuugucuucuugacuguucuucccucucuaucggggucacuugcaauuguuaaucaaagauugaacacugcgua
ggagagggagaugauccagagacauguggcagcaggcauggcuucccuuggccucucuguacacugccccag
gacugucauuuggcaucugcaaaggaaucacuuuagaaagccagcaccugguugauguguauucauacugac
auuagauugaugugcacugcauuagaaaugagguagcugacacagaaaaaggaauguuuugauaggaauaauuu
ucuaguaugucuugaaacauguucaucuggaaguauuuuccuccaaaguaauguagcaugauuuucaaggau
uguuaacaugccugggauugggaaagauaggacuaaaguugugccaaacuauaucAAUAAAuuccauguuuag
cagaaauaggcagccuauuggugu uauguuuauguaacauaguccagagaacugacaugcaggucaaaaguca
gauacgcaaccuccuuaucugcuaacucuguuauucuucaaacacaacgugggguagugucauuuuuccuuccu
uccuuccauuggcagauuguauauuuauucacaaaacauuaaauguccauccugugccaguacuaugcagau
guugagggauuggggucugguuagucgugacuaucuauccugaaucuaacagugacuucauaacuaggagac
ugaauuagacccuuaagguauagugugugu ugcaaaucacucugcaauggaaacuuuuauauucagguaggu
uugugucuuaaacuaggguucuaaucaauguacaagacuuuaccauacacgcaacuauaguuuuucuaaacc
uucaucauuugugauucuuugagaaagggcuuuuaggaacuuuauguucaaaaaauguuuuuaacaauaaua
agauaaaagaaaaaccugugauucauaugucc ccacuggcauuacucagcaggagcccccagcugccaaaggu
uggcagugauccugcaaguucaagggcucuuucucccuggggauguguuuuguggcuucucuuuacagcuuug
uuucugcaucaguucacugcugcauguuguuuggaauuuauccc uuaagaaagugucucuguuuuauauaga
aacacuuucucacuuacagggg agaaggaaaugcagggcacaugaucuggcccuccccagaacaaucggauu
ucacggagacagcaaccagaaguuaaaccaugugacuaaaaaugcaucggcuacuuuucauguauguauga
gacagaaacuaauccuuacuauccuauuaggauaccacuuuucauugcaaaguuugugucAAUAAAgucauua
auuuuaaacau

Fig. 7

1-4-5-6-8
gagagggcccggacuaggggcggcgggcaccgcaggagcuccgcgcggcugcagcgcgggcgggagcgggacgc
gaugucgccgccgccgccucccuugcgggccggggcugcgccuccggggcugagccgccgcagagccgacagccg
agcagccgcugggcgcucccgcggcgcaggaggAUGGGCUGCGGCGGGAGCCGGGCGGAUGCCAUCGAGCCCCGC
UACUACGAGAGCUGGACCCGGGAGACAGAAUCCACCUGGCUCACCUACACCGACUCGGACGCGCCGCCCAGCGCC
GCCGCSCCGGACAGCGGCCCCGAAGCGGGCGGCCUGCACUCGGGGUGCCUUGAGGAACAUUACCAUCUGACUGCC
CUACAGAAAGUUGGCCAUCCCAACCAUUGAUUUAAAAAGUUCUGGAGGCUGAGAAGUCCAAGAUCAAGGCACCAA
CAGAUUCAGUGUCUGAUGAAGGCUUGUUCUCUGCUUCAAAGAUGGCACCUCUUGCUGUGUUCUCACAUGGCAUGC
UGGAAGAUGGACUGCCCUCCAAUGGUGUGCCCCGAUCUACAGCCCCAGGUGGAAUACCCAACCCAGAGAAGAAGA
CGAACUGUGAGACCCAGUGCCCAAAUCCCCAGAGCCUCAGCUCAGGCCCUCUGACCCAGAAACAGAAUGGCCUUC
AGACCACAGAGGCUAAAAGAGAUGCUAAGAGAAUGCCUGCAAAAGAAGUCACCAUUAAUGUAACAGAUAGCAUCC
AACAGAUGGACAGAAGUCGAAGAAUCACAAAGAACUGUGUCAACUAGcagagaguccaagcagaagggcagaugg
acuucuucaguguccuucacggcacuggaucccaucaaagaaccuugaagaaguggcugccccuugcuggaccug
aauucacugagucccuggcaagacugucuuaccuggcagcaaacugcugccugauuuguugggaccuucugagc
cuucuacuuaucauguaaaauguauuggcacagugcuuacauauguuAAUAAAcugcaaaugugcaguucaguug
ucucuuugcaaccucuguaauacggucuggguguaaaaguagugaguuaaagcuacaggucaguuuaugaaacaga
aaaguaggaaugcauuuucuggguggaaagagucacaccuuagugcuauaacucuccugcccaugauaguguauuc
uguuucaggcaagcuuauucuuuccuucuuucauuuuaaauauugucauuacaaaucuuaccagguucacuuaaa
agcuggcuuucauccaacucuaaacccacauauugaaaaaaucaagguacaggaaaacuccuuguuauccuuguu
uccuuagcuugguaugagacagaucggauccaguuucccaugcaccaacccacugcccauggcaugucuuuggga
ggugucugugaagcagucauaccugcuccucaucugccuggaaaguccuccuauuccagguguccauguuggccuc
caguccuuaaugucaccaugcuuguggccaaugcauccaaauaaggauaccccucagggcucagcuagacauugc
aauuuugcauagcuuuccaguucccuuugcuugucuucugacugucuucccucucuaucggggucacuugcaau
uguuaaucaaagauugaacacugcguaggagagggagaugauccagagacauguggcagcaggcauggcuucccc
uuggccucucuguacacugccccaggacugucauuuggcaucugcaaaggaaucacuuuagaaagccagcaccu
gguugauguguauucauacugacauuagauugaugugcacugcauuagaaaugagguagcugacacagaaaaagg
auguuugauaggaauaauuuucuaguaugucuugaaacauguucaucuggaaguauuuccuccaaaguaaugu
agcaugauuuuucaaggauuguuaacaugccugggauugggaaagauaggacuaaaguuugugccaaacuauaucA
AUAAAuuccauguuuagcagaaauaggcagccuauuggaguguuauguuuauguaacauaguccagagaacugacau
gcaggucaaaagucagauacgcaaccuccuuaucugcuaacucuguuauucuucaaacacaacguggguaguguc
auuuuuccuuccuuccuuccauuggcagauuguauauuuauucacaaaacauuaaaauguccauccugugccaggu
acuaugcagauguugagggauuuggggucugguuagucgugacuaucuauccugaaucuaacagugacuucauaa
cuaggagacugaauuagacccuuaaggguauaguguguguguacaagacuuuaccauacacgcaacuauaguuuuucu
gguagguuugugucuuaaaacuaggugguucuaaaucaauguacaagacuuuaccauacacgcaacuauaguuuuucu
aaaccuucaucauuuugugauucuuugagaaagggcuuuuaggaacuuuauguucuaaaaaauguuuuuaacaau
aauaagauaaaagaaaaaccugugauucauauguccccacuggcauuacucagcaggagcccccagcugccaaag
guuggcagugauccugcaaguucaagggcucuuucuccuggggaugugcuuuguggcuucucuuuacagcuuug
uuucugcaucaguucacugcugcauguuguuuggaauuuaucaccuuaagaaaguguccucuguuuuauauagaaa
cacuuucucacuuacaggggagaaggaaaugcagggcacaugaucuggcccucccagaacaaucuggauuucac
ggagacagcaaccagaaguuaaaccaugugacuaaaaaugcaucuggcuacuuuucaugauguaugagacaga
aacuaauccuuacuauccuauuaggauaccacuuuucauugcaaaguuugugucAAUAAAgucauuaauuuuaaa
cau 1-5-6-7-8
gagagggcccggacuaggggcggcgggcaccgcaggagcuccgcgcggcugcagcgcgggcgggagcgggacgc
gaugucgccgccgccuccuugcgggccggggcugcgccuccggggcugagccgccgccagagccgacagccg
agcagccgcugggcgcuccgcggcgcaggaggAUGGGCUGCGGCGGGAGCCGGGCGGAUGCCAUCGAGCCCCGC
UACUACGAGAGCUGGACCCGGGAGACAGAAUCCACCUGGCUCACCUACACCGACUCGGACGCGCCGCCCAGCGCC
GCCGCSCCGGACAGCGGCCCCGAAGCGGGCGGCCUGCACUCGGUUCUGGAGGCUGAGAAGUCCAAGAUCAAGGCA
CCAACAGAUUCAGUGUCUGAUGAAGGCUUGUUCUCUGCUUCAAAGAUGGCACCUCUUGCUGUGUUCUCACAUGGC
AUGCUGGAAGAUGGACUGCCCUCCAAUGGUGUGCCCCGAUCUACAGCCCCAGGUGGAAUACCCAACCCAGAGAAG
AAGACGAACUGUGAGACCCAGUGCCCAAAUCCCCAGAGCCUCAGCUCAGGCCCUCUGACCCAGAAACAGAAUGGC
CUUCAGACCACAGAGGUUCUGCUGCCUUCCUAAUGUCUGAUCUUCUAUCUGAAGUUCAAGUUGAAAAGCAACAAC
UCCUUUUGGCACUCGAUACAAACUCCCAGGGCUAAAAGAGAUGCUAAGAGAAUGCCUGCAAAAGAAGUCACCAUU
AAUGUAACAGAUAGCAUCCAACAGAUGGACAGAAGUCGAAGAAUCACAAAGAACUGUGUCAACUAGcagagaguc
caagcagaagggcagauggacuucuucagugccuucacggcacuggaucccaucaaagaaccuugaagaagugg
cugccccuugcuggaccugaauucuacugaguccuggcaagacugucuuaccuggcagcaaacugcugccugau
uuguugggaccuucugagccuucuacuuaucauguaaauguauuggcacagugcuuacauauguuAAUAAAcugc
aaaugugcaguucaguuugucucuuugcaacuccuguaauacggucugguguaaaaguagugaguuaaagcuaca
ggucaguuuaugaaacagaaaaguaggaaugcauuuucugggugaagagucacaccuuagugcuauaacucucc
ugcccaugauagugauucuguuucaggcaagcuuauucuuuccuucuuucauuuuaaauauugucauuacaaau
cuuaccagguucacuuaaaagcuggcuuucauccaacucuaaaccacauauugaaaaaaucaaggucacaggaaa
acuccuuguuauccuuguuccuuagcuugguaugagacagaucggauccaguuucccaugcaccaacccacugc
ccauggcaugucuuugggaggugucugugaagcagucauaccugcuccucaucugccuggaaagucccuccuauuc
caguguccauguuggccuccaguccuuaauguCaccaugcuuguggccaaugcauccaaauaaggauaccccuca
gggcucagcuagacauugcaauuuugcauagcuuucaguuccuuugcuugcuucuugacugucuucccucuc
uaucgggucacuugcaauuguuaaucaaagauugaacacugcguaggagagggagaugauccagagacaugugg
cagcaggcauggcuuccccuuggccucucuguacacugcccaggacugucauuuugcaucugcaaaggaauca
cuuuagaaagccagcaccugguugauguguauucauacugacauuagauugauguCcacugcauuagaaaugagg
uagcugacacagaaaaggaugUuuugauaggaauaauuuucuaguaugucuugaaacauguucaucuggaagua
uuuuccuccaaaguaauguagCaugauuuuucaaggauuguuaacaugccugggauugggaaagauaggacuaaa
guugugccaaacuauaucAAUAAAuuccauguuuagcagaaauaggcagccuauggCuguuauguuuauguaaca
uaguccagagaacugacaugcaggucaaaagucagauacgcaaccuccuuaucugcuaacucuguuauucuucaa
acacaacgugggguagugucauuuuuccuuccuuccuuccauuggcagauuguauauuuauucacaaaacauuaaa
uguccauccugugccagguacuaugcagauguugagggauuugggucugguuagucgugacuaucuauccugaa
ucuaacagugacuucauaacuaggagacugaauuagacccuuaagguauagugugugUugcaaaucacucugcaa
uggaaacuuuuauauucagggUagguuuguguCuuaaacuagguguucuaaucaauguacaagacuuuaccauac
acgcaacuauaguuuucuaaaccuucaucauuuugugauucuuugagaaagggcuuuuaggaacuuuauguucuu
aaaaaauguuuuuaacaauaauaagauaaaagaaaaaaccugugauucauauguccccacuggcauuacucagcag
gagccccagcugccaaagguuggcagugauccugcaaguucaagggcucuuucuccegguggaugugcuuugug
gcuucucuuuacagcuuuguuucugcaucaguucacugcugcaugUuguuggaauUUaucaccuuaagaaagug
ucucuguuuuauauagaaacacuuucucacuuacaggggagaaggaaaugcagggcacaugaucuggcccucccc
agaacaaucuggauuucacggagacagcaaccagaaguuaaaccaugugacuaaaaaugcaucuggcuacuuuuu
cauguauguaugagacagaaacuaauccuuacuauccuauuaggauaccacuuuucauugcaaaguuuguguCAA
UAAAgucauuaauuuuaaacau

Fig. 9

1-2-6-8 gagagggcccggacuagggcggcgggcaccgcaggagcuccgcgcggcugcagcgcgggcgggagcgggacgc
gaugucgccgccgccgccuccuugcgggccggggcugcgccuccggggcugagccgccgccagagccgacagccg
agcagccgcugggcgcucccgcggcgcaggaggAUGGGCUGCGGCGGGAGCCGGGCGGAUGCCAUCGAGCCCCGC
UACUACGAGAGCUGGACCCGGGAGACAGAAUCCACCUGGCUCACCUACACCGACUCGGACGCGCCGCCCAGCGCC
GCCGCSCCGGACAGCGGCCCCGAAGCGGGCGGCCUGCACUCGGCCCAUUACCCUCUUGCCUUUGCACUUGCCUGG
AGAGACAACAGUUUAGGGGCUCUGCUGGUUCAAGAAGGACUGUGCAGGUAGCAUGGCCACACACCAUGUACAGGC
AUGCUGGAAGAUGGACUGCCCUCCAAUGGUGUGCCCCGAUCUACAGCCCCAGGUGGAAUACCCAACCCAGAGAAG
AAGACGAACUGUGAGACCCAGUGCCCAAAUCCCCAGAGCCUCAGCUCAGGCCCUCUGACCCAGAAACAGAAUGGC
CUUCAGACCACAGAGGCUAAAAGAGAUGCUAAGAGAAUGCCUGCAAAAGAAGUCACCAUUAAUGUAACAGAUAGC
AUCCAACAGAUGGACAGAAGUCGAAGAAUCACAAAGAACUGUGUCAACUAGcagagaguccaagcagaagggcag
auggacuucuucagugaccuucacggcacuggaucccaucaagaaccuugaagaaguggcugcccuugcugga
ccugaauucuacugaguccccuggcaagacugucuuaccuggcagcaaacugcugccugauuuguugggaccuucu
gagccuucuacuuaucauguaaauguauuggcacagugcuuacauaugullAAUAAAcugcaaaugugcaguucag
uuugucucuuugcaacuccuguaauacggucugguguaaaaguagugaguuaaagcuacaggucaguuuaugaaa
cagaaaaguaggaaugcauuuucggggugaaagagucacaccuuagugcuauaacucuccugcccaugauagugu
auucuguuucaggcaagcuuauucuuucccuucuuucauuuaaauauugucauuacaaaucuuaccagguucacu
uaaaagcuggcuuucauccaacucuaaacccacauauugaaaaaaucaagguacaggaaaacuccuuguuauccu
uguuuccuuagcuuggauagacagaucggauccaguuuccćaugcaccaaccacugcccauggcaugucuuu
gggaggugucugugaagcagucauaccugcuccucaucugccuggaaaguccuccuauuccagugaccauguugg
ccuccaguccuuaaugucaccaugcuuguggccaaugcauccaaauaaggauacccucagggcucagcuagaca
uugcaauuuugcauagcuuuccaguucccuuugcuugucuuucugacugucuucccucucuaucggggucacuug
caauuguuaaucaaagauugaacacugcguaggagagggagaugauccagagacauguggcagcaggcauggcuu
cccuuggccucucuguacacugccccaggacugucauuuuggcaucugcaaaggaaucacuuuagaaagccagc
accgguugaugguguauucauacugacauuagauugaugugcacugcauuagaaaugagguagcugacacagaaa
aaggauguuuugauaggaauaauuuucuaguaugucuugaaacauguucaucuggaaguauuuuccuccaaagua
auguagcaugauuuucaaggauuguuaacaugccugggauugggaaagauaggacuaaaguugugccaaacuau
aucAAUAAAuuccauguuuagcagaaauaggcagccuauggugulauguuuauguaacauagaccagagaacug
acaugcaggucaaaagucagauacgcaaccuccuuaucugcuaacucuguuauucuucaaacacaacguggguag
ugucauuuuccuuccuuccuuccauggcagauuguauauuuauucacaaaacauuaaauguccauccgugcc
agguacuaugcagauguugagggauuggggucugguuagucgugacuaucuauccugaaucuaacagugacuuc
auaacuaggagacugaauuagacccuuaagguauagugugugugugcaaaucacucugcaauggaaacuuuuauau
ucagggaugguuugugucuuaaacuaggguguucuaaucaauguacaagacuuuaccauacacgcaacuauaguuu
uucuaaaccuucaucauuuugugauucuuugagaaagggcuuuuaggaacuuuauguucuaaaaaauguuuuuaa
caauaauaagauaaagaaaaaccugugauucauauguccccacuggcauuacucagcaggagccccccagcugcc
aaagguuggcagugauccugcaaguucaagggcucuuucucccuggggaugugcuuuguggcuucucuuuacagc
uuuguuucugcaucaguucacugcugcauguuguuuggaauuuaucaccuuaagaagugucucuguuuauaua
gaaacacuucucuacuuacaggggagaaggaaaugcagggcacaugaucggcccucccagaacaaucggauu
ucacggagacagcaaccagaaguuaaaccaugugacuaaaaaugcaucuggcuacuuuucauguaguaugaga
cagaaacuaauccuuacuauccuauuaggauaccacuuuucauugcaaaguuugugucAAUAAAgucauuaauuu
uaaacau

Fig. 10

1-2-5-6-8
gagagggcccggacuaggggcggcgggcaccgcaggagcuccgcgcggcugcagcgcgggcgggagcggggacgcga
ugucgccgccgccgccuccuugcgggccggggcugcgccuccggggcugagccgccgccagagccgacagccgagca
gccgcugggcgcucccgcggcgcaggaggAUGGGCUGCGGCGGGAGCCGGGCGGAUGCCAUCGAGCCCCGCUACUAC
GAGAGCUGGACCCGGGAGACAGAAUCCACCUGGCUCACCUACACCGACUCGGACGCGCCGCCCAGCGCCGCCGCSCC
GGACAGCGGCCCCGAAGCGGGCGGCCUGCACUCGGCCCAUUACCCUCUUGCCUUUGCACUUGCCUGGAGAGACAACA
GUUUAGGGGCUCUGCUGGUUCAAGAAGGACUGUGCAGGUAGCAUGGCCACACACCAUGUACAGUUCUGGAGGCUGAG
AAGUCCAAGAUCAAGGCACCAACAGAUUCAGUGUCUGAUGAAGGCUUGUUCUCUGCUUCAAAGAUGGCACCUCUUGC
UGUGUUCUCACAUGGCAUGCUGGAAGAUGGACUGCCCUCCAAUGGUGUGCCCCGAUCUACAGCCCCAGGUGGAAUAC
CCAACCCAGAGAAGAAGACGAACUGUGAGACCCAGUGCCCAAAUCCCCAGAGCCUCAGCUCAGGCCCUCUGACCCAG
AAACAGAAUGGCCUUCAGACCACAGAGGCUAAAAGAGAUGCUAAGAGAAUGCCUGCAAAAGAAGUCACCAUUAAUGU
AACAGAUAGCAUCCAACAGAUGGACAGAAGUCGAAGAAUCACAAAGAACUGUGUCAACUAGcagagaguccaagcag
aagggcagauggacuucuucagugaccuucacggcacuggaucccaucaaagaaccuugaagaaguggcugcccccuu
gcuggaccugaauucuacugaguccuggcaagacugucuuaccuggcagcaaacugcugccugauugcuugggacc
uucugagccuucuacuuaucauguaaauguauuggcacagugcuuacauauguuAAUAAAcugcaaaugugcaguuc
aguuugucucuuugcaacuccuguaauacggucugguguaaaaguagugaguuaaagcuacaggucaguuuaugaaa
cagaaaaguaggaaugcauuucugggugaagagucacaccuuagugcuauaacucuccugcccaugauaguguau
ucuguuucaggcaagcuuauucuuccuucuuucauuuaaauaugcauuacaaaucuuaccagguucacuuaaa
agcuggcuuucaucuaaacccacauauugaaaaaaucaaggucacaggaaaacuccuuguuauccuuguuuc
cuuagcuuggauugagacagaucggauccaguuucccaugcaccaacccacugcccauggcaugucuuugggaggug
ucugugaagcagucauaccugcuccucaucugccuggaaagucuccuauuccagugucccauguuggccuccagucc
uuaaugucaccaugcuuguggccaaugcauccaaauaaggauaccccucagggcucagcuagacauugcaauuugc
auagcuuuccaguucccuuugcuugucuuucugacugucuucccucucuaucggggucacuugcaauuguuaaucaa
agauugaacacugcguaggagagggagaugauccagagacauguggcagcaggcauggcuucccuuggccucucug
uacacugcccaggacugucauuuugcaucugcaaaggaaucacuuagaaagccagcaccugguugauguguauu
cauacugacauuagauugaugugcacugcauuagaaaugagguagcugacacagaaaaggauguuuugauaggaau
aauuuucuaguaugucuugaaacauguucaucggaaguauuuccuccaaaguaauguagcaugauuuuucaagga
uuguuaacaugccugggauugggaaagauaggacuaaaguugugccaaacuauaucAAUAAAuuccauguuuagcag
aaauaggcagccuauuggguguuauguuuauguaacauaguccagagaacugacaugcaggucaaaagucagauacgc
aaccuccuuaucugcuaacucuguuauucuucaaacacaacgugggguagugucauuuuuccuuccuuccuuccauug
gcagauuguauauuuauucacaaaacauuaaaugaccauccugugccagguacuaugcagauguugagggauuggg
gucugguuagucgugacuaucuauccugaaucuaacagugacuucauaacuaggagacugaauuagaccccuuaaggu
auagugugguugcaaaucacucugcaauggaaacuuuuauauucaggguagguuuguguculuaaacuaggguguuucu
aaucaauguacaagacuuuaccauacacgcaacuauaguuuuucuaaaccuucaucauuugugauucuuugagaaa
gggcuuuuaggaacuuuauguucuaaaaaauguuuuaacaauaauaagauaaaagaaaaaccugugauucauaugu
ccccacuggcauuacucagcaggagcccccagcugccaaagguuggcagugauccugcaaguucaagggcucuuucu
cccugggaugugcuuugugggcuucucuuuacagcuuuguuucugcaucaguucacugcugcauguuguuuggaauu
uauccccuuaagaagugucucuguuuuauauagaaacacuuucucacuuacaggggagaaggaaaugcagggcaca
ugaucuggcccucccagaacaaucggauuucacggagacagcaaccagaaguuaaaccaugugacaaaaaugca
ucuggcuacuuuuucauguauguaugagacagaaacuaauccuuacuauccuauuaggauaccacuuuucauugcaa
aguuugugucAAUAAAgucauuaauuuuaaacau

Fig. 11

1-2-3-6-8
gagagggcccggacuaggggcggcgggcaccgcaggagcuccgcgcggcugcagcgcgggcgggagcggggacgcga
ugucgccgccgccgccuccuugcgggccggggcugcgccuccggggcugagccgccgcagagccgacagccgagca
gccgcugggcgcucccgcggcgcaggaggAUGGGCUGCGGCGGGAGCCGGGCGGAUGCCAUCGAGCCCCGCUACUAC
GAGAGCUGGACCCGGGAGACAGAAUCCACCUGGCUCACCACCGACUCGGACGCGCCGCCCAGCGCCGCCGCSCC
GGACAGCGGCCCCGAAGCGGGCGGCCUGCACUCGGCCCAUUACCCUCUUGCCUUUGCACUUGCCUGGAGAGACAACA
GUUUAGGGGCUCUGCUGGUUCAAGAAGGACUGUGCAGGUAGCAUGGCCACACACCAUGUACAGGUUCUGGUGCUUAG
GAGUGGACAUCUUUGGGACCGAGGGUUAUUCUGCCUUCCUACCAUGUCACCAGAGUUGUGCUAAUACACAGAGAGCU
UCAGGGGAUGAGAUCUGCCAUUCAUUGAGCACCUUCUGUGCGGCAGACAGUGUUAGGCAUGCUGGAAGAUGGACUGC
CCUCCAAUGGUGUGCCCCGAUCUACAGCCCCAGGUGGAAUACCCAACCCAGAGAAGAAGACGAACUGUGAGACCCAG
UGCCCAAAUCCCCAGAGCCUCAGCUCAGGCCCUCUGACCCAGAAACAGAAUGGCCUUCAGACCACAGAGGCUAAAAG
AGAUGCUAAGAGAAUGCCUGCAAAAGAAGUCACCAUUAAUGUAACAGAUAGCAUCCAACAGAUGGACAGAAGUCGAA
GAAUCACAAAGAACUGUGUCAACUAGcagagaguccaagcagaagggcagauggacuucuucagugaccuucacggc
acuggaucccaucaaagaaccuugaagaaguggcugcccuugcuggaccugaauucuacugagucccuggcaagac
ugucuuaccuggcagcaaacugcugccugauuuguugggaccuucugagccuucuacuuaucaugaaaauguauugg
cacagugcuuacauauguuAAUAAAcugcaaaugugcaguucaguuugucucuuugcaacuccuguaauacggucug
guguaaaaguagugaguuaaagcuacaggucaguuuaugaaacagaaaaguaggaaugcauuuucggggugaaagag
ucacaccuuagugcuauaacucuccugcccaugauaguguauucuguuucaggcaagcuuauucuuuccuucuuuca
uuuuaaauauugucauuacaaaucuuaccagguucacuuaaaagcuggcuuucauccaacucuaaacccacauauug
aaaaaaucaagguacaggaaaacuccuuguuauccuuguuuccuuagcuggguaugagacagaucggauccaguuuc
ccaugcaccaacccacugcccauggcaugucuuugggaggugucugugaagcagucauaccugcuccucaucugccu
ggaaagucccuccuauccagugucccauguuggccuccaguccuuaaugucaccaugcuuguggccaaugcauccaaa
uaaggauacccucagggcucagcuagacauugcaauuuugcauagcuuuccaguucccuuugcuugucuucuugac
ugucuuccucucuaucggggucacuugcaauuguuaaucaaagauugaacacugcguaggagagggagaugauccca
gagacauguggcagcaggcauggcuuccccuuggccucucuguacacugcccaggacugucauuuuggcaucuga
aaggaaucacuuuagaaagccgcaccuggugugguauuucauacugacauuagauugaugugcacugcauuaga
aaugagguagcugacacagaaaaaggaugguuugauaggaauaauuuucuaguaugucuugaaacauguucaucugg
aaguauuuuccuccaaaguaauguagcaugauuuuucaaggauuguuaacaugccugggauugggaaagauaggacu
aaaguugugccaaacuauaucAAUAAAuuccauguuuagcagaaauaggcagccuauggugguuauguuuauguaac
auaguccagagaacugacaugcaggucaaaagucagauacgcaaccuccuuaucugcuaacucuguuauucuucaaa
cacaacgugggguagugucauuuuuccuuccuuccuuccauuggcagauuguauauuuauucacaaaacauuaaaugu
ccauccugugccagguacuaugcagauguugagggauuuggggucugguuagucgugacuaucuauccugaaucuaa
cagugacuucauaacuaggagacugaauuagacccuuaagguauagugugugugugcaaaucacucugcaauggaaac
uuuuauauucaggguaggguugugucuuaaacuagguguucuaaucaauguacaagacuuuaccauacacgcaacua
uaguuuucuaaaccuucaucauuugugauucuugagaaagggcuuuaggaacuuuauguucuaaaaaauguuu
uuaacaauaauaagauaaaagaaaaaccugugauucauauguccccacuggcauuacucagcaggagcccccagcug
ccaaagguuggcagugauccugcaaguucaagggcucuuucucccuggggaugugcuuugggcuucucuuuacagc
uuuguuucugcaucaguucacugcugcauguguuuggaauuuaucaccuuaagaaagugucucuguuuauauaga
aacacuuucucacuuacaggggagaaggaaaugcagggcacaugaucuggccccucccagaacaaucuggauuucac
ggagacagcaaccagaaguuaaaccaugugacuaaaaaugcaucuggcuacuuuucauguauguaugagacagaaa
cuaauccuuacuauccauuaggauaccacuuuucauugcaaaguuugugucAAUAAAgucauuaauuuuaaacau

Fig. 12

1-6-8
MGCGGSRADAIEPRYYESWTRETESTWLTYTDSDAPPSAAAPDSGPEAGGLHS
GMLEDGLPSNGVPRSTAPGGIPNPEKKTNCETQCPNPQSLSSGPLTQKQNGLQ
TTEAKRDAKRMPAKEVTINVTDSIQQMDRSRRITKNCVN 1-8
MGCGGSRADAIEPRYYESWTRETESTWLTYTDSDAPPSAAAPDSGPEAGGLHS
G 1-5-6-8
MGCGGSRADAIEPRYYESWTRETESTWLTYTDSDAPPSAAAPDSGPEAGGLHS
VLEAEKSKIKAPTDSVSDEGLFSASKMAPLAVFSHGMLEDGLPSNGVPRSTAP
GGIPNPEKKTNCETQCPNPQSLSSGPLTQKQNGLQTTEAKRDAKRMPAKEVTI
NVTDSIQQMDRSRRITKNCVN 1-4-5-6-8
MGCGGSRADAIEPRYYESWTRETESTWLTYTDSDAPPSAAAPDSGPEAGGLHS
GCLEEHYHLTALQKVGHPNH 1-5-6-7-8
MGCGGSRADAIEPRYYESWTRETESTWLTYTDSDAPPSAAAPDSGPEAGGLHS
VLEAEKSKIKAPTDSVSDEGLFSASKMAPLAVFSHGMLEDGLPSNGVPRSTAP
GGIPNPEKKTNCETQCPNPQSLSSGPLTQKQNGLQTTEVLLPS 1-2-6-8, 1-2-5-6-8 and 1-2-3-6-8
MGCGGSRADAIEPRYYESWTRETESTWLTYTDSDAPPSAAAPDSGPEAGGLHS
AHYPLAFALAWRDNSLGALLVQEGLCR

BAALC EXPRESSION AS A DIAGNOSTIC MARKER FOR ACUTE LEUKEMIA

This application claims priority to U.S. Provisional Application Ser. No. 60/348,210, filed Nov. 9, 2001, which is incorporated herein in its entirety.

This invention was made, at least in part, with government support under National Institutes of Health Grant No. 5P30CA016058. The U.S. government has certain rights in the invention.

BACKGROUND

Leukemias comprise approximately 2% of adult cancers and are a heterogeneous group. There are two broad categories of leukemias. Acute leukemias arise when there is a block in the normal differentiation of cells to mature blood cells that results in large accumulations of immature cells or blasts in the blood. Examples of such cancers are acute myelogenous leukemia (AML; other names are acute myeloid leukemia and acute nonlymphocytic leukemia) and acute lymphoblastic leukemia (ALL). In chronic leukemia, on the other hand, there is unregulated proliferation of cells that have differentiated to mature blood cells. Examples of such cancers are chronic lymphocytic leukemia (CLL) and chronic myelogenous leukemia (CML). CML has a chronic phase which then progresses to a phase called blast crisis where immature, blast cells are present in the blood. Both acute and chronic leukemias involve the myeloid cells of the bone marrow, including white cells, red cells, megakaryocytes and cells of the lymphoid lineage.

The cytogenetics of many leukemias are characterized by balanced chromosomal translocations that give rise to gene rearrangements. In acute myeloid leukemia (AML) for example, about 55% of adult de novo cases have clonal cytogenetic abnormalities, many of which are specific translocations. However, in the remaining cases, no visible cytogenetic abnormalities are found, although genetic changes are detected methods other than cytogenetics. In adult acute lymphoblastic leukemia (ALL), the proportion of patients with no cytogenetic abnormality is about 31%.

Tumors of the central nervous system (CNS) comprise primary brain tumors, primary intraspinal tumors, and tumors that metastasize to the CNS. Brain tumors comprise astrocytomas, glioblastomas, medulloblastomas, and others. An extracranial pediatric tumor, neuroblastoma, arises in pluripotent neural crest cells of the sympathetic nervous system.

Prostate cancer is an epithelial cell cancer of men. Most are adenocarcinomas. Tumorigenesis progresses from normal to hyperplasiic prostate to well and poorly differentiated carcinoma.

Many cancers, including leukemias, CNS and prostate cancers suffer from the problem of late detection in patients. Also, even when such cancers are detected in a patient, it is often difficult to predict lifespan of, or to determine the optimal therapy for, the particular cancer in the particular patient. However, cancers are genetic diseases that are associated with changes in cellular DNA (i.e., genetic changes). Because occurrence of such DNA changes precedes the appearance of phenotypic changes characteristic of cancer cells, it is advantageous to use detection of such early genetic changes as an aid to cancer diagnosis. Also, because a single cancer type, as identified phenotypically or pathologically, may include cancers that can be subgrouped based on classification of genetic changes therein, detection of these genetic changes may provide improved patient prognosis and selection of more efficacious therapy, based on the subgroupings.

Although the specific genetic changes associated with some cancers are known, in other cancers the associated genetic changes are not known. Even if the genetic changes are not known, it may be possible to identify additional molecular changes resulting from the genetic changes contributing to cancer. For example, a genetic change in a cancer cell may result in changes in gene expression (i.e., transcription and/or translation) of multiple genes in a cancer cell. A gene which is not normally expressed in a particular cell type may come to be expressed in cancer cells, or a gene that is expressed at low levels in normal cells may come to be expressed at high levels in cancer cells. Such gene expression changes may be diagnostically and prognostically useful alone or may be used together with already identified cancer-associated genetic and gene expression changes in multivariate analysis for purposes of prognosis and selection of effective anticancer therapy.

Therefore, it would be advantageous to identify and characterize genetic changes and gene expression changes present in cancer cells, particularly in leukemias, CNS and prostate cancers, that can be used to more effectively diagnose a specific cancer, predict its outcome in a patient, and aid in selecting an efficacious therapy.

SUMMARY OF THE INVENTION

A new gene, BAALC (Brain and Acute Leukemia, Cytoplasmic) has been identified that has eight exons, and expresses eight alternatively-spliced transcripts and six protein isoforms. The BAALC gene, while normally expressed in central nervous system (CNS) tissues, adrenal gland, thyroid and spleen, is overexpressed in subsets of leukemias, in certain CNS cancers, and in prostate cancer.

Thus, the present invention provides oligonucleotides and polynucleotides sequences identical or complementary to sequences within BAALC exons or transcripts. The oligonucleotides are used as primers and probes for detecting BAALC expression and overexpression in a biological sample obtained from a patient.

The present invention also provides polyclonal and monoclonal antibodies that specifically bind to one or more BAALC protein isoforms, as well as peptide immunogens for preparing the antibodies. The antibodies are used for detecting expression and overexpression of BAALC proteins or polypeptides in a biological sample obtained from a patient.

The present invention also provides methods of characterizing certain leukemias in a patient. One such leukemia is acute myelogenous leukemia (AML). The method comprises assaying a biological sample obtained from a patient for the presence of one or more BAALC transcripts or protein isoforms, wherein overexpressed levels of BAALC transcripts or protein isoforms indicate an aggressive form of AML. Another such leukemia is chronic myelogenous leukemia (CML). This method comprises assaying a biological sample obtained from a patient for the presence of overexpressed levels of BAALC transcripts or protein isoforms wherein overexpressed levels in the CML cells indicates the cells have entered the stage of blast crisis.

The present invention also provides methods of diagnosing and characterizing prostate tumors. The method comprises assaying a biological sample obtained from a patient for the presence of overexpressed levels of BAALC transcripts or protein.

The present invention also provides a kit for characterizing AML, CML or prostate cancer wherein the kit comprises primers containing sequences identical or complementary to sequences within specific BAALC exons. The kit may also comprise a probe containing a sequence complementary to a sequence contained within a polymerase chain reaction (PCR) product obtained using the primers.

BRIEF DESCRIPTION OF THE FIGURES

FIG. 2 shows the DNA sequences of the eight exons of the human gene. Exons 1, 2, 3, 4, 5, 6, 7 and 8 are designated as SEQ ID NO:1, SEQ ID NO:2, SEQ ID NO:3, SEQ ID NO:4, SEQ ID NO:5, SEQ ID NO:6, SEQ ID NO:7 and SEQ ID NO:8, respectively. Lower case indicates untranslated regions. Upper case indicates translated regions. AATAAA sequences indicated by upper case letters indicates putative polyadenylation sites.

FIGS. 5-12 show RNA sequences of BAALC alternatively spliced transcripts 1-6-8 (SEQ ID NO:9), 1-8 (SEQ ID NO:10), 1-5-6-8 (SEQ ID NO:11), 1-4-5-6-8 (SEQ ID NO:12), 1-5-6-7-8 (SEQ ID NO:13), 1-2-6-8 (SEQ ID NO:14), 1-2-5-6-8 (SEQ ID NO:15), and 1-2-3-6-8 (SEQ ID NO:16), respectively. These are the sequences of the transcripts shown schematically in FIG. 1B. In the sequences, lower case indicates untranslated regions. Continuous stretches of upper case letters indicates translated regions. After the translated regions, upper case AAUAAA indicates putative polyadenylation sites. Bolded letters indicate the beginning of an exon sequence (see FIG. 2).

FIG. 15 shows amino acid sequences of the BAALC protein isoforms encoded by the RNA transcripts shown in FIG. 1B and FIGS. 5-12. BAALC proteins 1-6-8 (SEQ ID NO:17), 1-8 (SEQ ID NO:18), 1-5-6-8 (SEQ ID NO:19), 1-4-5-6-8 (SEQ ID NO:20), 1-5-6-7-8 (SEQ ID NO:21), as well as the same protein (SEQ ID NO:22) encoded by transcripts 1-2-6-8, 1-2-5-6-8 and 1-2-3-6-8 are shown.

DETAILED DESCRIPTION OF THE INVENTION

Definitions

Figure 1:
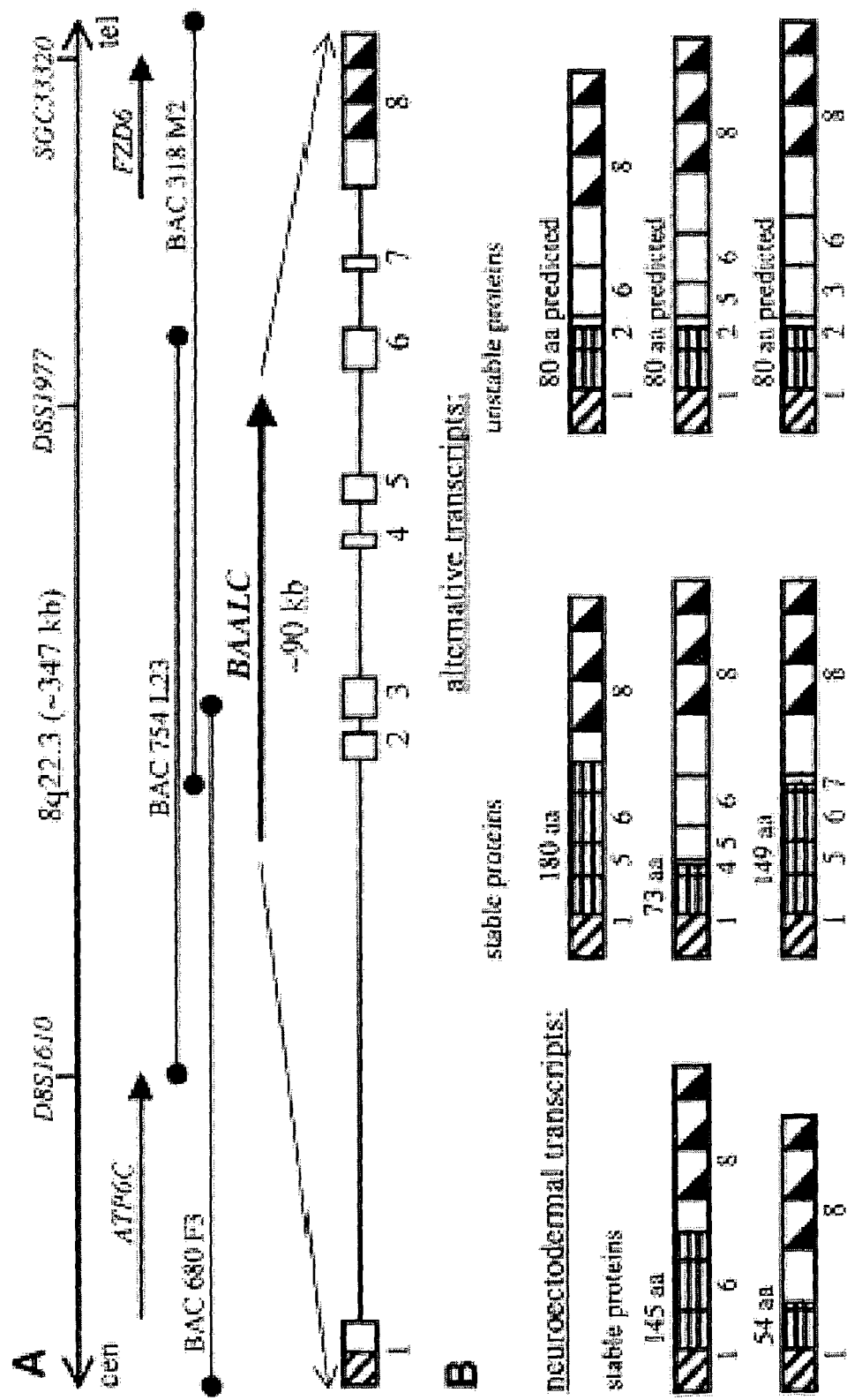
FIG. 1 shows the genomic organization and transcripts of the human BAALC gene. (A) BAALC is located between ATP6C proximal and FZD6 distal in human chromosome 8q22.3 and covers 90 kb of genomic sequence. The region in the three BAC clones shown were assembled as shown. BAALC has eight exons, depicted by boxes, with exon 8 containing three polyadenylation signals (triangles) in the 3' untranslated region (UTR) leading to three differently sized transcripts (FIG. 4A). Exon 1 contains the ATG start codon and a 5' UTR (diagonally striped). (B) The two transcripts 1-6-8 and 1-8 are detected in neuroectoderm tissues, and six more transcripts produced by alternative splicing are detected mainly in leukemias. The extent of the resulting coding regions are horizontally striped, and the protein sizes are indicated above.

Herein, "biological sample" means a sample of cells from a patient. These cells may be part of a tissue or organ sample obtained, for example, by biopsy, or they may be individual cells, for example, bone marrow cells, blood cells or even cells grown in culture. Preferably, such cells are cells obtained from peripheral blood. The cells from the blood that are assayed can be any or all cells present in the blood. Preferably, the cells assayed are blood-forming cells. More preferably, the cells are leukocytes. Such cells are commonly obtained by drawing a blood sample from a patient and then using standard techniques to purify or partially purify the cells from the blood. For example, a cellular fraction can be prepared as a "buffy coat" (i.e., leukocyte-enriched blood portion) by centrifuging whole blood for a short time at low speed (e.g., 10 min at 800 times gravity) at room temperature. Red blood cells sediment most rapidly and are present as the bottom-most fraction in the centrifuge tube. The buffy coat, containing the leukocytes, is present as a thin creamy white colored layer on top of the red blood cells. The plasma portion of the blood forms a layer above the buffy coat. Fractions from blood can also be isolated in a variety of other ways. One method is by taking a fraction or fractions from a gradient used in centrifugation to enrich for a specific size or density of cells.

The biological samples may be of normal cells, or may be of tumor cells, the tumor cells being benign or malignant. Generally, an assay that uses cells from such biological samples, herein, will be used to determine the presence of BAALC transcripts or proteins, or levels of BAALC transcripts or proteins. When such an assay is performed, the "test sample" will generally be a sample for which the presence or level of BAALC is unknown and is being tested to provide, for example, an indication of the aggressiveness of the cells. In such an assay, a "control sample" will preferably also be used. The control sample can be from normal (i.e., non-tumorigenic or non-neoplastic) tissue from the same patient from which the test sample is taken or can be from another person known or thought not to have the tumor that is present or thought to be present in the patient from whom the test sample is taken. Preferably, the control sample comprises the same type of cells that comprise the test sample. For example, if the test sample comprises leukocytes, it is preferable that the control sample is also a leukocyte sample.

The biological samples can be obtained from patients at various times. For example, a sample may be obtained from an individual who is suspected of having a tumor or cancer. Assay of such sample using the methods described below can indicate whether the individual has a tumor or cancer or can provide characterization of the tumor or cancer cells. Samples may also be obtained from an individual known to have a tumor or cancer (i.e., the sample is taken after the patient has already been diagnosed). Assay of such sample using the described methods may have prognostic value to the individual. Multiple samples can also be taken from the same individual, for example, at different times after diagnosis. Assay of such samples can indicate whether the cancer or tumor is growing or spreading. Such assays on multiple samples are especially informative in the case where it is desired to determine the effect of a chemotherapeutic or other therapeutic agent or agents on the growth and progression of the tumor or cancer in the individual.

The test samples are preferably obtained from patients who are known to have or suspected of having a tumor or cancer. Methods for diagnosis of particular tumors or cancers in patients are well known in the art of medicine, oncology and hematology.

Herein, "assaying," when used in reference to biological samples, preferably the cells in biological samples, refers to assessment or measurement of the presence and/or levels or concentrations of BAALC gene expression (transcripts or protein isoforms) in the samples. This assessment is done by detecting and/or measuring the levels of RNA transcribed from the BAALC gene or proteins which are translated from the RNA transcripts. As will be described subsequently, multiple transcripts, called alternative transcripts in the art, may be present when the BAALC gene is transcribed. Such alternative transcripts come from different combinations of exons encoded by the BAALC gene (see FIG. 2). Some or all of these transcripts are translated to produced BAALC proteins. The BAALC proteins that are obtained from translation of different alternative transcripts, may be somewhat different (in size and/or sequence) from one another depending on the combination of exons existing in the particular alternative transcript or on how the exon sequences in the transcripts are translated. Such different proteins are known in the art as protein "isoforms."

Assaying these samples, with respect to BAALC expression, may involve detection or quantification of one or more specific alternative transcripts or protein isoforms. For example, one may be interested in determining the presence, level or concentration of one specific alternative transcript or protein isoform. Alternatively, assaying the samples may involve detection or levels of BAALC transcripts or proteins as a whole. For example, in determining the level or concentration of BAALC transcripts, the sum of the levels of all of the different alternative transcripts or protein isoforms may be used.

With regard to elevated levels or elevated concentrations of one or more BAALC alternative transcripts or protein isoforms, "elevated" means an increase in the amount of the transcript or isoform in the test sample as compared to the control sample. "Elevated in the test sample as compared to the control sample" describes a situation where the presence of BAALC transcripts or proteins is detected in the test sample and the amount, level or concentration of the BAALC transcripts or proteins in the test sample is greater than in the control sample. This means, in the control sample, that BAALC transcripts or proteins are either not detected, or that BAALC transcripts or proteins are detected, but are not present in amounts, levels or concentrations as high as are present in the test sample.

Therefore, to ascertain whether the test sample contains "overexpressed" levels of BAALC, a comparison of the levels in the test sample to the levels in one or more control samples is performed. Levels in a control sample or samples can be represented by a single value or range of values. Preferably, an average of the BAALC levels in more than one control sample is used for comparison with the BAALC levels in the test sample. More preferably, an average of the BAALC levels from a number of control samples sufficient to provide a statistically significant comparison with BAALC levels present in the test sample is used. The control sample levels of BAALC may be determined at the same time at which BAALC levels in the test sample is determined. The BAALC levels in the control samples may also be predetermined, meaning that the levels have been determined before the time at which BAALC levels in the test samples are determined. In the case where BAALC levels in control samples are predetermined, the values are preferably normalized or standardized such that they can be legitimately compared with values for BAALC levels in test samples that are determined later.

With reference to overexpressed, increased or elevated levels of BAALC transcripts or proteins in the test sample, the amount of the increase can be of various magnitudes. The increase may be relatively large. For example, a large increase could be a 100% or more increase in BAALC expression in the test sample as compared to the control sample. However, the increase may be relatively small. For example, the increase may be less than 100%, less than 50%, or even less than a 10% increase of the transcript or protein in the test sample as compared to the control sample. Preferably, whatever the degree or magnitude of the increase, such increase is statistically significant. Methods for determining whether an increase is statistically significant are well known in the art of statistics and probability.

Comparison of the test sample to the control sample for the presence and/or levels of BAALC expression is used to characterized the tumor or cancer, i.e., to determine the "aggressiveness" of the tumor or cancer. A level of BAALC transcripts or proteins in the test sample that is higher than the level in the control sample indicates presence of an aggressive tumor or cancer. The extent or degree of the increase between the level of BAALC transcripts or proteins in the test sample and the control sample correlates with degree of aggressiveness of the tumor or cancer. Aggressiveness refers to the nature of tumor cell growth a patient. For example, an aggressive cancer has a higher probability of producing an unfavorable outcome in a patient than a cancer that is less aggressive. "Unfavorable outcome" normally refers to the probability that a patient will have a relatively short lifespan due to the aggressive nature of the cancer. Patients with a less aggressive cancer or cancer that is not aggressive are expected to have a longer lifespan than a patient with an aggressive form of the cancer.

In addition to predicting outcome in a patient, determination of BAALC overexpression, and tumor or cancer aggressiveness, is used for selecting an appropriate therapy for the patient with the tumor or cancer. In addition, determination of BAALC overexpression is used for determining if such a therapy is used and when it should be used to treat the patient.

Cloning of BAALC

The present invention provides a new gene, BAALC (Brain and Acute Leukemia, Cytoplasmic), expression of which is diagnostic for certain cancers and prognostic for patients with certain cancers. To clone the gene, a cDNA-RDA (cDNA representational difference analysis) study was performed by using mRNA from AML cells of a patient without cytogenetic abnormalities as the driver and mRNA from AML+8 (trisomy 8) cells of a patient as the tester. cDNA-RDA analysis was performed according to protocols provided by D. G. Schatz (Yale Univ., New Haven, Conn.) and M. J. O'Neill (Princeton University Princeton) with some modifications. Briefly, 20 mg of total RNA (pooled from AML+8 from three patients for the tester and from cytogenetically normal AML from four patients for the driver) was poly(A)-selected and transcribed into cDNA by using Dynabeads Oligo $dT_{25}$ (Dynal, Great Neck, N.Y.) and Superscript II reverse transcriptase (Invitrogen). The resulting cDNA was DpnII-digested (New England Biolabs), R-adapters were added with T4 ligase (New England Biolabs), and tester and driver representations were amplified by using Expand High-Fidelity DNA polymerase (Roche Diagnostics). R-adapters were removed by DpnII digest. This step concluded the processing of the driver. For the tester, J-adapters were added by ligation and, the first round of subtractive hybridization was performed at a ratio of 100:1 (driver:tester). Two rounds of PCR with an intermediate mung-bean nuclease digest (New England Biolabs) were performed for difference product 1 (DP1). For a second round of subtractive hybridization, the J-adapters were replaced by N-adapters, and the ratio was increased to 800:1. DP2 was cloned into the BamHI site of pZERO-1 (Invitrogen). Inserts were PCR-amplified by using M13 universal primers and sequenced on an ABI 377 sequencer (Applied Biosystems). Sequences were used in BLAST searches against GenBank.

The sequencing, as above, of 209 RDA clones detected a total of 27 genes, 5 ESTs, and 5 unknown sequences. One frequently detected sequence was EST clone AA400649, belonging to Uni-Gene cluster Hs.169395 in chromosome 8q22.3. This gene was named BAALC for brain and acute leukemia, cytoplasmic.

RDA clone sequences representing partial cDNA clones from BAALC were used to design PCR primers, which were labeled and used in reverse transcription (RT)-PCR using a subset of the human bacterial artificial chromosome (BAC) library RPC-11 as template. Four positive BAC clones, RP11-754L23, RP11-626K19, RP11-701N2, and RP11-773L13 were found. Primer walking, cDNA clone sequencing, and RT-PCR allowed assemblage of the BAALC gene (GenBank accession no. AF363578, which also contains the genomic sequence of BAALC), which is fully contained in BAC clone RP11-754L23 (on human chromosome 8) (FIG. 1). All remaining gaps in BAC clones 680F3 and 318M2 (GenBank AC025936 and AC025370) were closed by primer walking. BAALC covers 90 kb of genomic sequence. Exon 1 is located 72 kb distal to the 3'-end (D8S1610) of the ATP6C gene, and exon 8 (D8S1977) is 68 kb proximal to the 5'-end of the FZD6 gene. The DNA sequences of exons 1-8 are shown in FIG. 2. Using a similar strategy, mouse Baalc was also cloned.

BAALC is Conserved in Mammals

Figure 3:
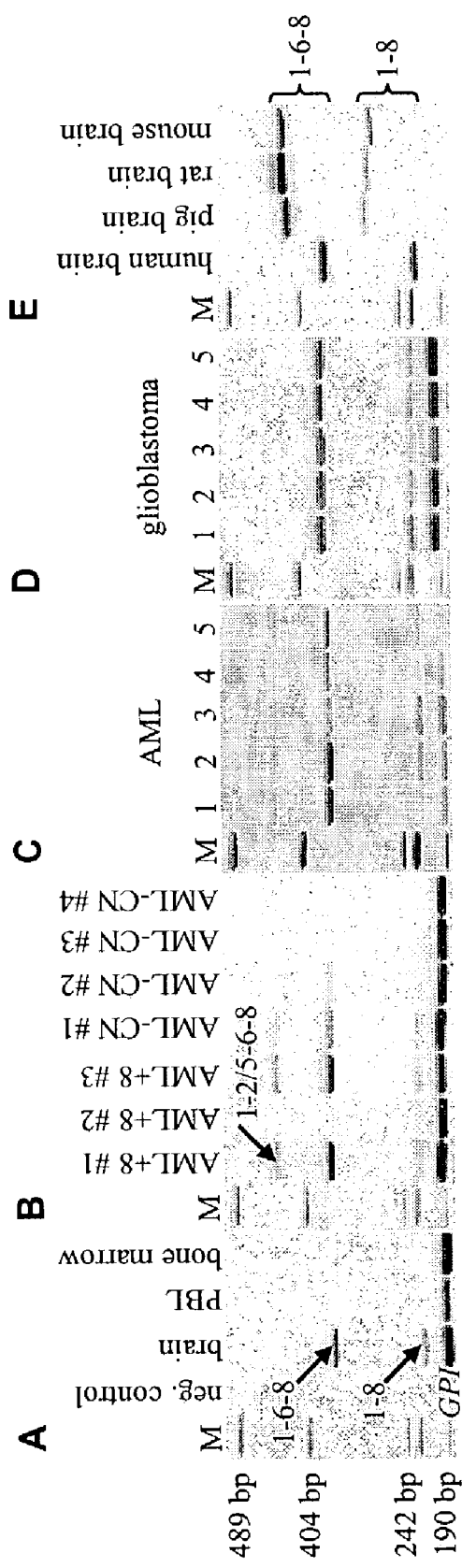
FIG. 3 shows comparative reverse transcription polymerase chain reaction (RT-PCR) results using primers in exons 1 and 8 of human BAALC in biological samples from brain, peripheral blood leukocytes (PBL), bone marrow (BM), 12 cases with AML, and 5 glioblastoma tumors with GPI serving as an internal control. M, size marker. (A) Exon 6 was alternatively spliced in brain and leads to transcripts 1-6-8 and 1-8. Transcript 1-6-8 was more highly expressed than transcript 1-8 in brain. No BAALC expression was detected in PBL, but faint expression occurred in BM. (B) The three cases of AML with +8 (trisomy for chromosome 8) and four cases of AML with normal karyotype (AML-CN) used in the cDNA-RDA experiment were studied individually by RT-PCR. The samples with AML+8, nos. 1 and 3, had very high levels of transcript 1-6-8, whereas the samples with AML-CN, nos. 1 and 2, had low levels of the transcripts. Moreover, two alternative transcripts, 1-2-6-8 and 1-5-6-8, were observed in the AML samples that were absent in brain. (C) Samples from five cases containing AML had alternative transcripts when BAALC was overexpressed. (D) Although the five glioblastoma tumor samples had transcripts 1-6-8 and 1-8, which were highly expressed, they were distinguished by their lack of expression of the alternative transcripts. (E) Conservation of BAALC splicing of transcripts 1-6-8 and 1-8 in brain samples from four mammalian species shown by RT-PCR with primers in exons 1 and 8.

Database searches for BAALC orthologs in other species detected ESTs from mouse (UniGene Mm.44234 and Mm.85430) and rat (Rn.19969 and Rn.57689). In addition, three domestic pig ESTs (BF190130, BF192691, and BF193189) when assembled, contained the complete orthologous ORF for isoform 1-6-8 (see below). The putative 145-amino acid protein was 92% conserved compared with the human. Deposited mouse ESTs predicted that the mouse expressed orthologous transcripts to human BAALC 1-6-8 and 1-8 (see below). The predicted protein isoform 1-6-8 was 89% conserved compared with the human. RT-PCR was performed on brain RNA from human, domestic pig, rat, and mouse and confirmed the expression of both orthologous transcripts 1-6-8 and 1-8 in all species (FIG. 3E). Rat isoform 1-6-8 was highly similar (98%) to the mouse and was also 89% conserved compared with the human. Moreover, pig, mouse, and rat isoforms 1-8 were all 95% conserved compared with human (GenBank accession nos. AF371319-

Figure 4:
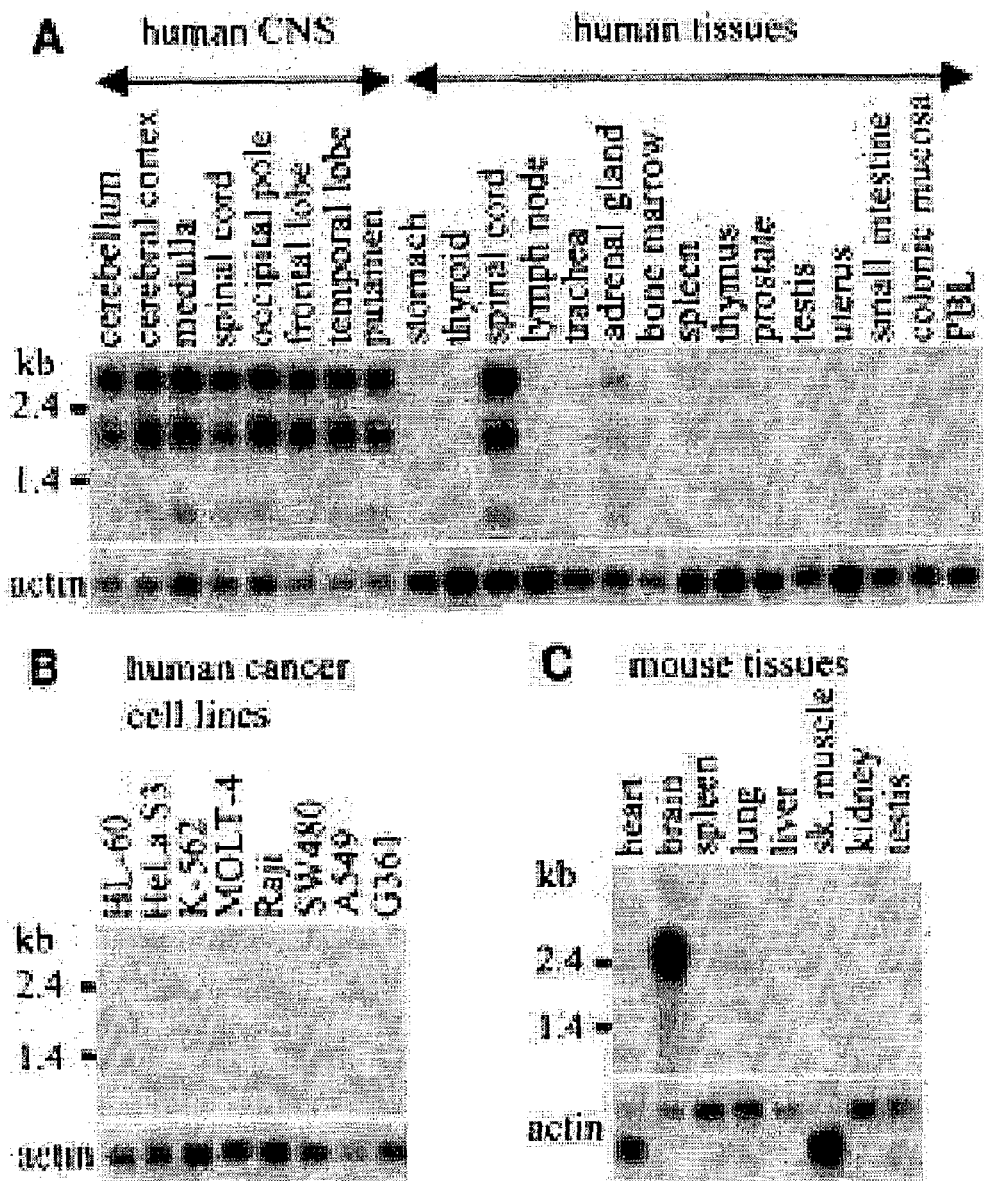
FIG. 4 shows the issue-expression pattern of BAALC. (A) Northern blots probed with human transcript 1-6-8. High expression of BAALC was restricted to neural tissues, and low expression was seen in the neuroectoderm-derived tissues adrenal gland, thyroid, and spleen. Note undetectable levels of BAALC in samples from BM, PBL, and lymph nodes, as well as in eight human cancer cell line samples (B). BAALC was expressed as three differently sized transcripts of about 1, 2, and 3 kb, because of the alternative usage of the three poly(A) signals in exon 8. (C) A mouse Northern blot probed with BAALC transcript 1-6-8 from mouse displayed a major 2.7-kb transcript exclusively in brain, indicating the same neuroectoderm-specific expression as in human, with a clear preference for the second poly(A) signal.

AF371326). A mouse multitissue Northern blot showed clear preference for the second polyadenylation signal, with high expression of a 2.7-kb transcript in brain (FIG. 4C). Finally, the mouse Baalc gene locus was mapped with the T31 radiation hybrid panel to proximal mouse chromosome 15. The data had the highest anchor logarithm of odds (lod) score of 15.6 to D15Mit112, then lod score 14.4 to D15Mit6, and finally lod score 11.5 to D15Mit22. The best-fit location was between D15Mit112 proximal and D15Mit85 distal.

BAALC Expression is Specific for Neuroectoderm-Derived Tissues

The expression pattern of BAALC in human and mouse was investigated. Most ESTs from BAALC (Uni-Gene Hs.169395) were from central nervous system (CNS)-derived cDNA libraries, and exon 6 was found to be alternatively spliced in brain RNA (FIG. 3A). Thus, the gene was expressed in two transcripts, transcript 1-6-8 (2827 bp) and transcript 1-8 (2660 bp) with predicted ORFs of 145- and 54-amino acids, respectively (FIG. 1B).

By comparative RT-PCR, bone marrow (BM) showed barely detectable, and peripheral blood leukocytes (PBL) showed no expression of BAALC (FIG. 3A). BAALC expression in BM was confined to the CD34-positive progenitor cells.

The tissue specificity of BAALC was examined using multitissue Northern (MTN) blots were assayed by using transcript 1-6-8 as a probe (FIG. 4A). Human BAALC transcript 1-6-8 and mouse Baalc transcript 1-6-8 were random primer-labeled (Roche Diagnostics) and used to probe species-specific multi-tissue Northern blots (CLONTECH). All blots were probed with human β-actin cDNA as a control.

The results of this study showed that BAALC expression was specific for neuroectoderm-derived tissues. BAALC showed high expression in all CNS tissues, including the spinal cord. Moderate levels of BAALC expression were found in adrenal gland and weak levels in thyroid and spleen, which are in part neuroectoderm-derived. In other tissues, notably BM, PBL, and lymph nodes, no detectable levels of BAALC were recorded (FIG. 4A). Furthermore, an MTN blot containing eight human cancer cell lines tested completely negative for BAALC. In addition, an MTN blot containing eight human cancer cell lines (promyelocytic leukemia HL-60, cervix adenocarcinoma HeLa S3, chronic myelogenous leukemia K-562, lymphoblastic leukemia MOLT-4, Burkitt's lymphoma Raji, colorectal adenocarcinoma SW480, lung carcinoma A549, and melanoma G361), tested completely negative for BAALC (FIG. 4B). All cell lines were obtained from American Type Culture Collection. These Northern blot experiments showed the expression of two major transcripts of 2 kb and 3 kb with a third minor transcript of about 1 kb, indicating alternative usage of the three observed polyadenylation signals in exon 8, but without affecting the putative ORFs.

Alternative BAALC Transcripts and Protein Isoforms

As described above, alternatively spliced transcripts 1-6-8 and 1-8 are encoded by BAALC. Six additional transcripts, 1-5-6-8, 1-4-5-6-8, 1-5-6-7-8, 1-2-6-8, 1-2-5-6-8 and 1-2-3-6-8 also exist and are most often seen in certain tumor or cancer cells (see Example 1 below). These transcripts arise from alternative splicing and comprise combinations of the exons shown in FIG. 2. These transcripts are shown schematically in FIG. 1B and the sequences of the transcripts are shown in FIGS. 5-12.

Figure 13:
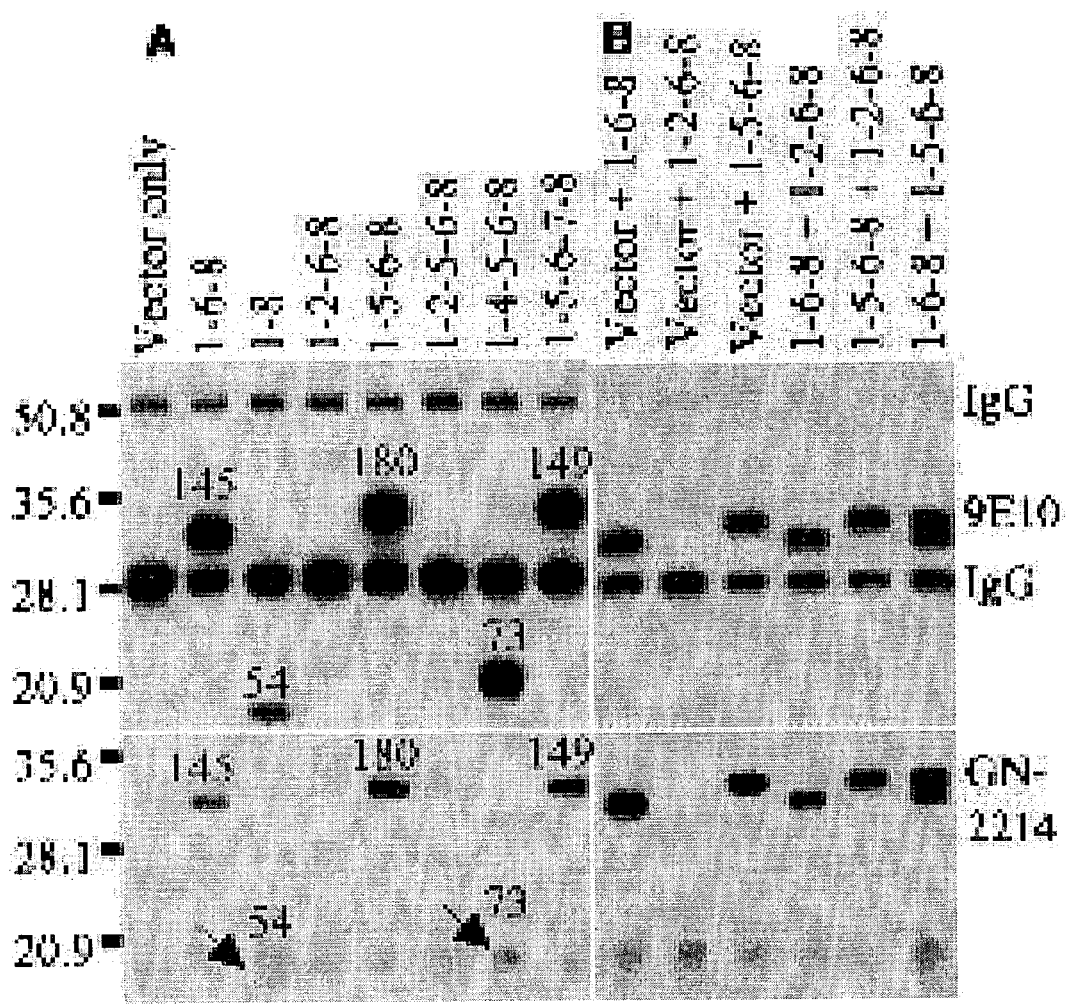
FIG. 13 shows expression of BAALC protein isoforms. (A) Immunoprecipitation-Western blot analysis of isoforms 1-6-8 and 1-8, and the five alternative isoforms 1-2-6-8, 1-5-6-8, 1-2-5-6-8, 1-4-5-6-8, and 1-5-6-7-8 cloned into pcDNA3-5×Myc and transfected into 293 cells. BAALC protein detection was with anti-Myc mouse antibody 9E10 against the N-terminal Myc tag (Upper) or with anti-BAALC antibody GN2214, which is specific for amino acids encoded by exon 1 (Lower). The neuroectodermal transcripts, 1-6-8 and 1-8, produced the expected protein isoforms of 145- and 54-amino acids, respectively. Also as expected, transcripts 1-5-6-8, 1-4-5-6-8 and 1-5-6-7-8 produced the protein isoforms of 180-, 73- and 149-amino acids, respectively. Arrows indicate the small 54- and 73-amino acid isoforms. All isoforms contain an additional 63 amino acids from the N-terminal Myc tag. The secondary anti-mouse IgG antibody detected the IgG heavy and light chains from 9E10 (used for immunoprecipitation) on the Upper blot, which are not seen with the secondary anti-rabbit IgG antibody used on the Lower blot. (B) Coexpression in 293 cells of neuroectodermal isoform 1-6-8, stable isoform 1-5-6-8, and unstable isoform 1-2-6-8 with vector and with one another as indicated above the lanes. The last lane depicts coexpression of both stable isoforms. The results are confirmed with both 9E10 (Upper) and GN2214 (Lower).
Figure 14:
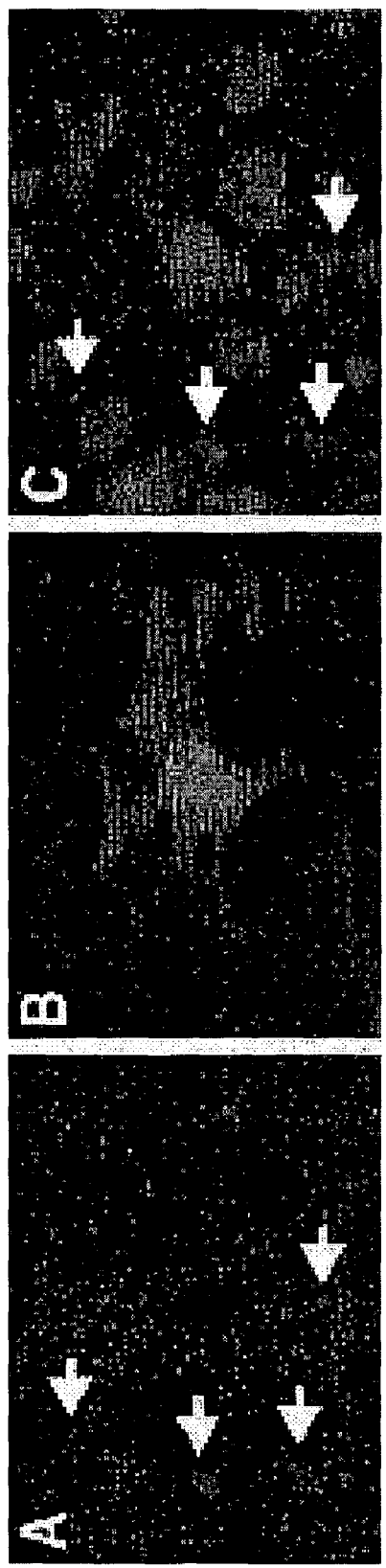
FIG. 14 shows subcellular localization of BAALC protein. (A) Subcellular localization of human BAALC is shown after transfection of Myc-tagged isoform 1-6-8 into NIH/3T3 cells and staining with 9E10 and rhodamine-conjugated secondary antibody. (B) pcDNA3-green fluorescent protein served as a transfection control. (C) Triple-filter image. Nuclei were stained with 4',6-diamidino-2-phenylindole (DAPI). BAALC occurred as a few large inclusions (arrows) in the peripheral parts of the cytoplasm.

Translation of the 8 different transcripts of BAALC indicated 6 different protein isoforms. The amino acid sequences of proteins encoded by each of the alternatively spliced transcripts are shown in FIG. 15. All have the same first 53 amino acids encoded by exon 1, but the remaining coding sequences are different. The use of exon 2 in 3 of the transcripts indicated the same 80-amino acid protein was encoded, as the sequence of exon 2 comprises a termination codon. The coding sequences of all transcripts, except 1-2-3-6-8, were cloned into an expression vector that added 63 amino acids, containing 5 Myc epitopes, to the N terminus of all isoforms. After the clones were expressed in 293 cells, the resulting proteins were immunopreciptiated with anti-Myc antibody and assayed for BAALC expression by Western blot analysis. Protein expression for isoforms 1-6-8 and 1-8, and for the 3 isoforms 1-5-6-8, 1-4-5-6-8, and 1-5-6-7-8 were detected (FIG. 13A). To study the intracellular localization of the proteins, NIH/3T3 cells were transfected with expression constructs from all five transcripts noted above. Using fluorescence microscopy, all isoforms were localized to the cytoplasm, where they appeared as a few large inclusions in the cellular periphery (FIG. 14A-C).

BAALC Expression and Overexpression in Cancers

Methods are provided to determine the level of BAALC gene expression in a biological sample. One method determines the amount of RNA transcribed from the BAALC gene. Another method determines the amount of BAALC protein.

Isolation of RNA from Patient Cell Samples

To determine the amount of BAALC RNA in a sample, RNA is first isolated from the tissue or cells comprising the biological sample. The biological sample is preferably a peripheral blood sample as was described earlier. A variety of methods of RNA isolation from cells and/or tissues is well known to those skilled in the art. Any of such methods can be used. One such method uses the Trizol® reagent from Gibco BRL. Such methods isolate total cellular RNA. Other methods isolate polyadenylated RNA. Methods that provide either type of RNA can be used.

RT-PCR

Reverse transcriptase reactions coupled to polymerase chain reactions (RT-PCR) is one method to assay for the presence of an RNA in a pool of total RNA from a tissue or cell. Detection of a particular RNA is dependent on primers used in the PCR reaction.

RT

The initial step in RT-PCR is a reverse transcription step. Procedures for reverse transcription are well known to those skilled in the art and a variety of procedures can be used. Either total RNA or polyadenylated mRNA can be used as the template for synthesis of cDNA by the reverse transcriptase enzyme.

In one embodiment, oligo(dT) is used as the primer in the reverse transcription reaction. Oligo(dT) hybridizes to the poly(A) tails of mRNAs during first strand cDNA synthesis. Since all mRNAs normally have a poly(A) tail, first strand cDNA is made from all mRNAs present in the reaction (i.e., there is no specificity). In another embodiment, specific primers are used in place of oligo(dT) and specific RNAs are reverse transcribed into DNA. The specific primers preferably are complementary to a region near the 3' end of the RNA in order that full length or nearly full length cDNA is produced. Primer selection is preferably made using the guidelines described below for selection of PCR primers. A number of different primers can be used with good results. For reverse transcription of BAALC RNA, two different primers are preferably alternatively used. The first primer is called ES99 and has the sequence 5'-CATCTGTTGGATGCTATCTG-3' (SEQ ID NO:23). The second primer is called ES10 and has the sequence 5'-TGGACTCTCTGCTAGTTGAC-3' (SEQ ID NO:24). For reverse transcription of the housekeeping gene, glucose phosphate isomerase (GPI) the primer preferably is called GPI Exon3R and has the sequence 5'-TCGGTGTAGT-TGATCTTCTC-3' (SEQ ID NO:25).

Preferably, the reverse transcriptase enzyme used in the reaction is stable at temperatures above 60° C., for example, SuperScript II RT (Gibco BRL). However, MMLV reverse transcriptase can also be used. In one embodiment, the reverse transcriptase reaction mixture contains 10 mM Tris (pH 8.3), 40 mM KCl, 1.5 mM MgCl$_2$, 1 mM dithiothreitol, 200 μM each of dATP, dCTP, dTTP and dGTP, 200 ng of the primer, 10 U of AMV reverse transcriptase from Boehringer Mannheim Biochemicals, and 20 units of RNASIN from Promega.

The disaccharide, trehalose, can be added to the reverse transcriptase reaction. Trehalose is a disaccharide that has been shown to stabilize several enzymes including RT at temperatures as high as 60° C. (Mizuno, et al., Nucleic Acids Res. 27:1345-1349, 1999). Trehalose addition allows the use of high temperatures in the reverse transcription reaction (e.g., as high as 60° C.). Therefore, trehalose can be added to the reverse transcriptase reaction such that it is present in a final concentration of between 20 to 30%. Preferably, the reverse transcriptase reaction is then performed at a temperature between 35 to 75° C., more preferably at a temperature from between 50 to 75° C., most preferably at a temperature of 60° C.

PCR

Once the reverse transcriptase reaction is carried out, the cDNA produced is amplified by PCR. In one embodiment, the entire RT-PCR reaction is carried out on a standard thermal cycler according to the methods described in the GeneAmp RNA PCR kit obtained from Perkin-Elmer/Cetus, for example. A 0.5 pg sample of total RNA from the cells is used to produce the first strand cDNA. The amplification cycle protocol is as follows: 95° C. for 2 minutes, 95° C. for 1 minute, 56° C. for 1 minute, and 72° C. for 2 minutes, through 35 cycles.

In another embodiment, a standard PCR reaction contains a buffer containing 10 mM Tris-HCl (pH 8.3), 50 mM KCl, and 6.0 mM MgCl$_2$, 200 uM each of dATP, dCTP, dTTP and dGTP, two primers of concentration 0.5 uM each, 7.5 ng/ul concentration of template cDNA and 2.5 units of Taq DNA Polymerase enzyme. Variations of these conditions can be used and are well known to those skilled in the art.

The PCR reaction is preferably performed under high stringency conditions. Herein, "high stringency PCR conditions" refers to conditions that do not allow base-pairing mismatches to occur during hybridization of primer to template. Such conditions are equivalent to or comparable to denaturation for 1 minute at 95° C. in a solution comprising 10 mM Tris-HCl (pH 8.3), 50 mM KCl, and 6.0 mM MgCl$_2$, followed by annealing in the same solution at about 62° C. for 5 seconds.

The products of the PCR reaction can be detected in various ways. One way is by agarose gel electrophoresis which involves separating the DNA in the PCR reaction by size in electrophoresis. The agarose gel is then stained with dyes that bind to DNA and fluoresce when illuminated by light of various wavelengths. Preferably the dye used is ethidium bromide and the illumination uses an ultraviolet light.

Primer Selection

One primer is located at each end of the region to be amplified. Such primers will normally be between 10 to 30 nucleotides in length and have a preferred length from between 18 to 22 nucleotides. The smallest sequence that can be amplified is approximately 50 nucleotides in length (e.g., a forward and reverse primer, both of 20 nucleotides in length, whose location in the sequences is separated by at least 10 nucleotides). Much longer sequences can be amplified. Preferably, the length of sequence amplified is between 75 and 250 nucleotides in length.

One primer is called the "forward primer" and is located at the left end of the region to be amplified. The forward primer is identical in sequence to a region in the top strand of the DNA (when a double-stranded DNA is pictured using the convention where the top strand is shown with polarity in the 5' to 3' direction). The sequence of the forward primer is such that it hybridizes to the strand of the DNA which is complementary to the top strand of DNA.

The other primer is called the "reverse primer" and is located at the right end of the region to be amplified. The sequence of the reverse primer is such that it is complementary in sequence to a region in the top strand of the DNA. The reverse primer hybridizes to the top strand of the DNA PCR primers should also be chosen subject to a number of other conditions. PCR primers should be long enough (preferably 10 to 30 nucleotides in length) to minimize hybridization to greater than one region in the template. Primers with long runs of a single base should be avoided, if possible. Primers should preferably have a percent G+C content of between 40 and 60%. If possible, the percent G+C content of the 3' end of the primer should be higher than the percent G+C content of the 5' end of the primer. Primers should not contain sequences that can hybridize to another sequence within the primer (i.e., palindromes). Two primers used in the same PCR reaction should not be able to hybridize to one another. Although PCR primers are preferably chosen subject to the recommendations above, it is not necessary that the primers conform to these conditions. Other primers may work, but have a lower chance of yielding good results.

PCR primers that can be used to amplify DNA within a given sequence are preferably chosen using one of a number of computer programs that are available. Such programs choose primers that are optimum for amplification of a given sequence (i.e., such programs choose primers subject to the conditions stated above, plus other conditions that may maximize the functionality of PCR primers). One computer program is the Genetics Computer Group (GCG recently became Accelrys) analysis package which has a routine for selection of PCR primers. There are also several web sites that can be used to select optimal PCR primers to amplify an input sequence. One such web site is alces.med.umn.edu/rawprimer.html. Another such web site is www-genome.wi.mit.edu/cgi-in/primer/primer3_www.cgi.

Forward and reverse primers can be selected from a variety of regions of the BAALC gene. Actually, a very large number of primers can be designed using the sequence of the BAALC gene and such probes successfully used. Preferably, for PCR amplification of BAALC, the forward primer is designed using a sequence within exon 6 of BAALC and the reverse primer is designed using a sequence within exon 8 of BAALC. Both the forward and reverse primers can also be designed using sequences within exon 8.

Three different sets of primers are preferably used alternatively for BAALC. Primer set 1 produces a 173 base pair amplification product. The set 1 primers are the forward primer (ES6) 5'-ACCCAGAGAAGAAGACGAAC-3' (SEQ ID NO:26) and the reverse primer (ES99) 5'-CATCTGTTG-GATGCTATCTG-3' (SEQ ID NO:23). Primer set 2 produces a 101 base pair amplification product. The set 2 primers are the forward primer (ES9) 5'-AGAAACAGAATGGCCT-TCAG-3' (SEQ ID NO:27), and the reverse primer (ES99) 5'-CATCTGTTGGATGCTATCTG-3' (SEQ ID NO:23).

Primer set 3 produces a 75 base pair amplification product. The set 3 primers are the forward primer (BAALC 6F) 5'-GCCCTCTGACCCAGAAACAG-3' (SEQ ID NO:28), and the reverse primer (BAALC 8R) 5'-CTTTTGCAGGCATTCTCTTAGCA-3' (SEQ ID NO:29).

The GPI primers preferably used are the forward primer (GPI Exon1F) 5'-TCTTCGATGCCAACAAGGAC-3' (SEQ ID NO:30), and the reverse primer (Hsa E2R) 5'-GCATCACGTCCTCCGTCAC-3' (SEQ ID NO:31).

Real-Time PCR

The PCR procedure can also be done in such a way that the amount of PCR products can be quantified. Such "quantitative PCR" procedures normally involve comparisons of the amount of PCR product produced in different PCR reactions. A number of such quantitative PCR procedures, and variations thereof, are well known to those skilled in the art. One inherent property of such procedures, however, is the ability to determine relative amounts of a sequence of interest within the template that is amplified in the PCR reaction.

One particularly preferred method of quantitative PCR used to quantify copy numbers of sequences within the PCR template is a modification of the standard PCR called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). In one type of real-time PCR, the reaction mixture also contains a reagent whose incorporation into a PCR product can be quantified and whose quantification is indicative of copy number of that sequence in the template. One such reagent is a fluorescent dye, called SYBR Green I (Molecular Probes, Inc.; Eugene, Oreg.) that preferentially binds double-stranded DNA and whose fluorescence is greatly enhanced by binding of double-stranded DNA. When a PCR reaction is performed in the presence of SYBR Green I, resulting DNA products bind SYBR Green I and fluoresce. The fluorescence is detected and quantified by the fluorimeter. Such technique is particularly useful for quantification of the amount of template in a PCR reaction.

A preferred variation of real-time PCR is TaqMan® (Applied Biosystems) PCR. The basis for this method is to continuously measure PCR product accumulation using a dual-labeled flourogenic oligonucleotide probe called a TaqMan® probe. The "probe" is added to and used in the PCR reaction in addition to the two primers. This probe is composed of a short (ca. 20-30 bases) oligodeoxynucleotide sequence that hybridizes to one of the strands that are made during the PCR reaction. That is, the oligonucleotide probe sequence is homologous to an internal target sequence present in the PCR amplicon. The probe is labeled or tagged with two different flourescent dyes. On the 5' terminus is a "reporter dye" and on the 3' terminus is a "quenching dye." One reporter dye that is used is called 6-carboxy fluorescein (FAM). One quenching dye that is used is called 6-carboxy tetramethyl-rhodamine (TAMRA). When the probe is intact, energy transfer occurs between the two fluorochromes and emission from the reporter is quenched by the quencher, resulting in low, background fluorescence. During the extension phase of PCR, the probe is cleaved by the 5' nuclease activity of Taq polymerase, thereby releasing the reporter from the oligonucleotide-quencher and producing an increase in reporter emission intensity. During the entire amplification process the light emission increases exponentially.

Although a variety of different probes can be used, the preferred probes are as follows: the probe used with the BAALC set 1 and 2 PCR primers is TaQExonD with the sequence 5'-CAGGCATTCTCTTAGCATCTCTTTT-3' (SEQ ID NO:32). The probe used with the BAALC set 3 PCR primers is 5'-CTCTTTTAGCCTCTGTGGTCTGAAGGCCAT-3' (SEQ ID NO:33). The probe used with the previously described probes for amplification of GPI (GPI Exon1F and Has E2R) has the sequence 5'-TTCAGCTTGACCCTCAACACCAAC-3' (SEQ ID NO:34).

The instrument used to detect the fluorescence is preferably an ABI Prism 7700, which uses fiber optic systems that connect to each well in a 96-well PCR tray format. The laser light source excites each well and a CCD camera measures the fluorescence spectrum and intensity from each well to generate real-time data during PCR amplification. The ABI 7700 Prism software examines the fluorescence intensity of reporter and quencher dyes and calculates the increase in normalized reporter emission intensity over the course of the amplification. The results are then plotted versus time, represented by cycle number, to produce a continuous measure of PCR amplification. To provide precise quantification of initial target in each PCR reaction, the amplification plot is examined at a point during the early log phase of product accumulation. This is accomplished by assigning a fluorescence threshold above background and determining the time point at which each sample's amplification plot reaches the threshold (defined as the threshold cycle number or CT). Differences in threshold cycle number are used to quantify the relative amount of PCR target contained within each tube as described in the Examples which follow below.

Northern Blotting

In addition to RT-PCR, other procedures can be used to detect RNA that is transcribed from the BAALC gene. One such method is known as Northern blot hybridization. In this method, RNA is isolated from tissues or cells and separated by size using gel electrophoresis. The RNAs in the gel are then transferred to a membrane. After transfer of the RNA to the membrane, a nucleotide probe is labeled and hybridized to the RNA on the membrane. Hybridization of a DNA probe to RNA on the membrane is detected by autoradiography or chemiluminescence.

A variation of Northern blotting, is called slot blotting or dot blotting. In this technique, the isolated RNA is applied directly to a membrane. The nucleotide probe is then labeled and hybridized to the RNA on the membrane. Hybridization is detected by autoradiography or chemiluminescence.

Probes of many different lengths and sequences can be designed and used in Northern blotting experiments to detect BAALC transcripts.

Antibodies

Another method for detecting and quantifying overexpression of BAALC uses antibodies immunuospecific for one or more isoforms of the BAALC protein to detect the protein in extracts or fixed cells, for example. Hereinafter, unless specifically indicated otherwise, "BAALC protein" refers not to a single protein, but to multiple BAALC proteins that are represented by the different isoforms (see FIG. 15). The present invention provides antibodies that are immunospecific for the BAALC protein. As used herein, the term "immunospecific" means the antibodies have greater affinity for the BAALC protein than for other proteins. Preferably, the affinity of the antibodies for BAALC protein is many fold greater than their affinity for any other proteins. Most preferably, the BAALC antibodies do not have affinity for any proteins other than BAALC protein.

The term "antibody" encompasses monoclonal antibodies, polyclonal antibodies, multispecific antibodies (e.g., bispecific antibodies), and antibody fragments, so long as they exhibit the desired biological activity or specificity. "Antibody fragments" comprise a portion of a full length antibody, generally the antigen binding or variable region thereof. Examples of antibody fragments include Fab, Fab', F(ab')$_2$, and Fv fragments.

Antibodies raised against BAALC are produced by immunizing a host animal with a BAALC protein or an antigenic fragment thereof. Suitable host animals for injection of the protein immunogen include, but are not limited to, rabbits, mice, rats, goats, and guinea pigs. Various adjuvants may be used to increase the immunological response of the immunogen or antigen (i.e., the BAALC protein or peptide) in the host animal. The adjuvant used depends, at least in part, on the host species. For example, guinea pig albumin is commonly used as a carrier for immunizations in guinea pigs. Such animals produce heterogeneous populations of antibody molecules, which are referred to as polyclonal antibodies and which may be derived from the sera of the immunized animals. Such sera may be used directly, or the specific antibodies desired can be purified from the sera, using methods well known to those of skill in the art.

Antibodies are also prepared using an oligopeptide having a sequence which is identical to a portion of the amino acid sequence of a BAALC protein isoform. Preferably the oligopeptide has an amino acid sequence of at least five amino acids, and more preferably, at least 10 amino acids that are identical to a portion of the amino acid sequence of a BAALC protein. Preferably, the peptides used are either GN2214, having an amino acid sequence of DAIEPRYYESWTRETEST (SEQ ID NO:35), or GN2216, having an amino acid sequence of DSIQQMDRSRRITK (SEQ ID NO:36). SEQ ID NO:35 is found in all 6 of the BAALC protein isoforms shown in FIG. 15. SEQ ID NO:36 is found in 2 of the BAALC protein isoforms shown in FIG. 15, namely the 1-6-8 and 1-5-6-8 isoforms. Such peptides are conventionally fused with those of another protein such as keyhole limpet hemocyanin and antibody is produced against the chimeric molecule. Such peptides can be determined using software programs, for example the MacVector program, to determine hydrophilicity and hydrophobicity and ascertain regions of the protein that are likely to be present at the surface of the molecule.

The term "monoclonal antibody" as used herein, refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site, also called epitope. Furthermore, in contrast to conventional (polyclonal) antibody preparations, which typically include different antibodies directed against different determinants (epitopes), each monoclonal antibody is directed against a single determinant on the antigen.

The monoclonal antibodies to be used in accordance with the present invention may be made by the hybridoma method, first described by Kohler and Milstein (Nature 256:495-497, 1975), in which case the hybridoma cell lines that are obtained secrete the monoclonal antibodies during growth. As is known in the art, hybridomas that secrete monoclonal antibodies are made by injecting mice with the desired antigen. The antigens frequently are peptide antigens which are chosen using similar procedures as described above for selection of peptide antigens for making polyclonal antibodies. Although many different peptide antigens from BAALC likely give good results, a preferred peptide antigen for making monoclonal antibodies has the amino acid sequence RADAIEPRYYESWTRETESTWLTYT (SEQ ID NO:37). SEQ ID NO:37 is found in all 6 of the BAALC protein isoforms shown in FIG. 15. After the antigens have been injected into the mice, spleen cells are taken from the immunized mice and are fused to myeloma cells. Clones of fusion cells are then obtained and are screened for production of anti-BAALC antibodies.

Various immunoassays may be used for screening to identify antibodies having the desired specificity. These include protocols which involve competitive binding or immunoradiometric assays and typically involve the measurement of complex formation between the respective BAALC protein and the antibody.

In order to grow the hybridoma cell lines and obtain the secreted antibodies, the hybridoma cell lines may be grown in cell culture and culture medium containing the monoclonal antibodies collected. Alternatively, the hybridoma cell lines may be injected into, and grown within, the peritoneal cavity of live animals, preferably mice. As the hybridoma cell lines grow within the peritoneal cavity of the animal, the monoclonal antibodies are secreted. This peritoneal fluid, called "ascites," is collected using a syringe to obtain the monoclonal antibodies. Such antibodies may be of any immunoglobulin class including IgG, IgM, IgE, Iga, IgD and any class thereof.

Antibody preparations may be isolated or purified. An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step Antibodies immunospecific for BAALC are useful for identifying tissues or cells that express BAALC proteins. The diagnostic/prognostic methods comprise the steps of contacting tissues or cells with such antibody and assaying for the formation of a complex between the antibodies and a BAALC protein in the samples. Preferably the cells are permeabilized. Interactions between antibodies and a protein or peptide in the sample are detected by radiometric, colorimetric, or fluorometric means. Detection of the antigen-antibody complex may be accomplished by addition of a secondary antibody that is coupled to a detectable tag, such as for example, an enzyme, fluorophore, or chromophore. Preferably, the detection method employs an enzyme-linked immunosorbent assay (ELISA), Western immunoblot procedure and/or immunoprecipitation.

Western Blots

Protein or cell-free extracts are made from tissues or cells. In one method, cells are lysed in 500 ul ice-cold Lysis Buffer (50 mM Tris pH 7.5; 1% Triton X-100; 100 mM NaCl; 50 mM NaF; 200 uM Na$_3$VO$_4$; 10 ug/ml pepstatin and leupeptin) (all chemicals from Sigma Chemical Co., St. Louis, Mo.) for approximately 30 min at 4° C. The cell lysate suspension is then microcentrifuged at 4° C. (14,000 RPM for 10 min). The supernatant is removed and stored at −80° C. Proteins are separated using SDS-polyacrylamide gel electrophoresis (SDS-PAGE) through a 6%-7.5% acrylamide gel at 100V. The samples are transferred to an Immobilon-P membrane (Millipore, Bedford, Mass.). Blots are blocked in phosphate buffered saline (PBS: 138 mM NaCl, 15 mM $Na_2HPO_4$, 1.5 mM KCl, and 2.5 mM $KH_2PO_4$), containing 5% non-fat dehydrated milk and 0.1% Tween-20 (Sigma Chemical Co., St. Louis, Mo.) overnight at 4° C. Blots are incubated for 90-120 min at room temperature in PBS with primary anti-BAALC antibody and then washed three times in PBS with 0.1% Tween-20. Blots are then incubated with secondary antibody conjugated to horseradish peroxidase (1:4000 dilution) (Sigma Chemical Co., St. Louis, Mo.) for 1 hour at room temperature and washed again as described above. Signal is visualized by incubating with Super Signal chemiluminescent substrate (Pierce, Rockford, Ill.) and exposing the membrane to Kodak scientific imaging film (Kodak, Rochester, N.Y.).

EXAMPLES

Further details of the invention can be found in the following examples, which further define the scope of the invention and serve to illustrate but not to limit the present invention.

Example 1

Alternative Splicing of BAALC in Acute Myeloid Leukemia Samples

Blasts from BM or peripheral blood (PB) were collected from patients with AML. Total RNA was isolated using Trizol (Invitrogen). Total RNA from AML cells from these patients was reverse-transcribed with avian myeloblastosis virus reverse transcriptase (Roche Diagnostics) using oligo(dT) as primer. The reverse transcriptase reaction mixture contained 10 mM Tris (pH 8.3), 40 mM KCl, 1.5 mM $MgCl_2$, 1 mM dithiothreitol, 200 µM each of dATP, dCTP, dTTP and dGTP, 200 ng of the primer, 10 U of AMV reverse transcriptase from Boehringer Mannheim Biochemicals, and 20 units of RNA-SIN from Promega. The reverse transcriptase reaction was then performed at a temperature of 60° C.

PCR was then performed using the cDNA from the reverse transcriptase reaction as template. Primer sequences from exons 1 and 8 of human BAALC were used. The primer from exon 1 was ES100, 5'-GTGCGGTACCAAGCTTCCGCG-GCGCAGGAGGATG-3' (SEQ ID NO:38), The primer from exon 8 was ES102, 5'-CGGGGTACCGTTGACACAGT-TCTTTGTGATTC-3' (SEQ ID NO:39). Both BAALC and the housekeeping gene GPI (glucose phosphate isomerase) were coamplified in the same tube. The primer sequences for GPI were the forward primer (GPI Exon1F) 5'-TCTTCGAT-GCCAACAAGGAC-3' (SEQ ID NO:30) and the reverse primer (Hsa E2R) 5'-GCATCACGTCCTCCGTCAC-3' (SEQ ID NO:31). The PCR reaction contained 10 mM Tris-HCl (pH 8.3), 50 mM KCl, and 6.0 mM $MgCl_2$, 200 uM each of dATP, dCTP, dTTP and dGTP, the two primers of concentration 0.5 uM each, 7.5 ng/ul concentration of template cDNA and 2.5units of Taq DNA Polymerase enzyme. The amplification cycle protocol was as follows: 95° C. for 2 minutes, 95° C. for 1 minute, 56° C. for 1 minute, and 72° C. for 2 minutes, through 35 cycles. The products of the PCR reaction were then separated by agarose gel electrophoresis and the gel was stained with ethidium bromide, illuminated with ultraviolet light, and photographed.

The results (FIG. 3B) showed that transcripts were detected in the AML samples that were not seen previously in the CNS. The PCR fragments were cloned and sequenced using standard techniques showed the presence of 5 new exons that were numbered 2-5 and 7, which led to 6 additional alternatively spliced transcripts (FIG. 1B). Including the transcripts 1-6-8 and 1-8, there were 8 alternatively spliced transcripts (FIG. 1B and FIGS. 5-12) in the blasts of patients with acute leukemia who were expressing high levels of BAALC.

Additional studies showed that 5 of 27 diverse patients with AML contained elevated or overexpressed BAALC transcript levels as compared to GPI (e.g., see lanes 1 and 2 in FIG. 3C). Certain of the AML samples expressed very high levels of BAALC. FIG. 3B shows this to be true for AML+8 nos. 1 and 3.

Example 2

BAALC Overexpression in Normal Cells and Various Cancer Samples, Including Glioblastoma Samples Real-time PCR (TaqMan®, Applied Biosystems) was used to quantify the relative levels of BAALC transcripts in various tissues and cancers using total RNA isolated from the cells using Trizol (Invitrogen). Initially, RNA samples from several organs including BM, PBL, brain and fetal brain, plus different human tumor samples were analyzed. Additionally, RNA samples from 10 normal human tissues, 10 colorectal cancer-normal colonic mucosa-matched sample pairs, 3 esophageal cancer-normal esophagus-matched sample pairs, 3 lung tumor samples, 5 glioblastoma samples, 2 thyroid carcinoma-normal thyroid-matched sample pairs, 1 thyroid carcinoma sample, and 3 testicular and 3 mammary tumor samples were analyzed for expression of BAALC.

Reverse transcription was performed using the total RNA isolated from the cells. Separate primers for reverse transcription were used to synthesize cDNA for both BAALC and for GPI. For BAALC, two primers were alternatively used: (ES99) 5'-CATCTGTTGGATGCTATCTG-3' (SEQ ID NO:23) or (ES10) 5'-TGGACTCTCTGCTAGTTGAC-3' (SEQ ID NO:24). Both ES99 and ES10 were derived from sequences within exon 8 of BAALC. For GPI, the primer (GPI Exon3R) was 5'-TCGGTGTAGTTGATCTTCTC-3' (SEQ ID NO:25).

Real-time PCR was then performed with both the BAALC and GPI housekeeping gene coamplified in the same tube. The TaqMan® real-time PCR system (Applied Biosystems) was used. Separate primers and probes were used for both BAALC and for GPI.

Three different sets of primers were alternatively used for BAALC. Primer set 1 produced a 173 base pair amplification product. The set 1 primers were the forward primer (ES6) 5'-ACCCAGAGAAGAAGACGAAC-3' (SEQ ID NO:26) and the reverse primer (ES99) 5'-CATCTGTTGGATGC-TATCTG-3'. ES6 was derived from sequences within exon 6 of BAALC. The BAALC probe (TaQExonD) used with set 1 primers was 5'-CAGGCATTCTCTTAGCATCTCTTTT-3' (SEQ ID NO:32). Primer set 2 produced a 101 base pair amplification product. The set 2 primers were the forward primer (ES9) 5'-AGAAACAGAATGGCCTTCAG-3' (SEQ ID NO:27), and the reverse primer (ES99) 5'-CATCTGTTG-GATGCTATCTG-3' (SEQ ID NO:23). ES9 was derived from sequences within exon 6 of BAALC. The BAALC probe (TaQExonD) used with set 2 primers was 5'-CAGGCAT-TCTCTTAGCATCTCTTTT-3' (SEQ ID NO:32). Primer set 3 produced a 75 base pair amplification product. The set 3 primers were the forward primer (BAALC 6F) 5'-GC-CCTCTGACCCAGAAACAG-3' (SEQ ID NO:28), and the reverse primer (BAALC 8R) 5'-CTTTTGCAGGCAT- TCTCTTAGCA-3' (SEQ ID NO:29). BAALC 6F was derived from sequences within exon 6 of BAALC. BAALC 8R was derived from sequences within exon 8 of BAALC. The BAALC probe used with set 3 primers was 5'-CTCTTT-TAGCCTCTGTGGTCTGAAGGCCAT-3' (SEQ ID NO:33).

The GPI primers and probes were the forward primer (GPI Exon1F) 5'-TCTTCGATGCCAACAAGGAC-3' (SEQ ID NO:30), and the reverse primer (Hsa E2R) 5'-GCAT-CACGTCCTCCGTCAC-3' (SEQ ID NO:31). The GPI probe used with the GPI primers was 5'-TTCAGCTTGACCCT-CAACACCAAC-3' (SEQ ID NO:34). The analysis was performed using triplicate samples.

To determine the relative levels of expression of BAALC among the samples, the comparative $C_T$ method was used (Applied Biosystems). Briefly, the threshold cycles ($C_T$) for BAALC and Glucose-phosphate isomerase (GPI) were determined, and the cycle number difference ($\Delta C_T$=GPI−BAALC) was calculated for each replicate. If BAALC failed to reach the software-set threshold, the sample was considered below detection limit. If GPI amplification failed, the sample was omitted from the analysis. Finally, relative BAALC expression was calculated using the mean of $\Delta C_T$ from the three replicates, that is $MC_T = \mu(\Delta C_T) = (\Sigma \Delta C_T)/3$, normalizing BAALC expression to GPI expression.

Aside from the AML samples (Example 1) already scored as overexpressing BAALC, only glioblastoma tumor samples showed comparable levels of BAALC expression. All five glioblastoma samples strongly expressed BAALC in the range of 0.74-3.71 $MC_T$, but only transcripts 1-6-8 and 1-8 (FIG. 3D), distinguishing them from the acute leukemia samples (FIG. 3C).

A cut off of $MC_T \geq 0.75$ was used to score leukemia samples as overexpressors. The $MC_T$ for normal tissues, including brain, fetal brain, spleen, and several normal BM samples were well below this threshold and in the range of −12.4 to −0.14 $MC_T$. Because low expression in five BM samples was obtained (−10.57 to −7.2 $MC_T$), CD34-positive progenitor cells of two healthy donors were twice immunomagnetically enriched. The >95% pure CD34-positive hematopoietic progenitor populations expressed BAALC in the range of −4.2 to −2.0 $MC_T$, whereas the CD34-negative fractions were below the detection limit.

Example 3

BAALC Overexpression in Leukemia Samples

Real-time PCR (TaqMan®, Applied Biosystems) was used to quantify the relative levels of BAALC transcripts in different leukemia samples, using total RNA isolated from the cells in real-time PCR, as described in Example 2. Blasts from BM or peripheral blood from 130 diverse AML patients, 31 ALL patients, 4 Burkitt's lymphoma (BL) patients, 5 chronic myelogenous leukemia (CML) patients, 5 chronic lymphocytic leukemia (CLL) patients, plus the 7 leukemia cell lines HL-60, KG-1, KG-1a, MC-1010, K-562, D1.1, and RS4;11, were analyzed. Pretreatment BM aspirate or peripheral blood samples from patients with the different leukemias were collected after prior consent. CD34-positive progenitor cells were enriched twice from normal BM aspirates by immunomagnetic separation, using MiniMACS columns (Miltenyi Biotec, Auburn, Calif.). Cell lines were obtained from the American Type Culture Collection. Total RNA was isolated using Trizol (Invitrogen).

Cases with MCT≧0.75 were classified as BAALC overexpressors. In AML, 37/130 (28%), and in ALL, 20/31 (65%) were classified as BAALC overexpressors (0.75 to 8.59 $MC_T$), but none of the BL, CML, and CLL samples, or leukemia cell lines scored as overexpressors (below detection limit to 0.46 $MC_T$).

Example 4

BAALC Overexpression in AML Samples

Real-time PCR (TaqMan®, Applied Biosystems) was used to quantify the relative levels of BAALC transcripts in samples from patients with AML, using total RNA isolated from the cells in real-time PCR, as described in Example 2. One hundred two samples from adult patients with de novo AML from which peripheral blood samples were available and centrally reviewed clinical data were statistically analyzed. The samples were obtained from the Cancer and Leukemia Group B (CALGB) Leukemia Tissue Bank (see Proc. Natl. Acad. Sci. 98:13901-13906, 2001) and were cancers with evaluable cytogenetics enrolled in a prospective cytogenetic companion study, CALGB 8461. These patients had peripheral blood samples with >50% blasts. Cases with AML with $MC_T \geq 0.75$ were classified as BAALC overexpressors. Event-free survival was measured from the on-study date until date of treatment failure, relapse, or death, censoring only for patients alive and in continuous complete remission.

Of 102 patient samples analyzed by real-time PCR, 29 (28%) were BAALC overexpressors. The distribution of BAALC overexpression differed significantly among AML French-American-British subtypes (P<0.0001). It was overexpressed in all 5 cases of M0, in 12/28 M1, 7/28 M2, and 3/4 M4Eo samples, but in no M3 (0/6), and only in 1/14 M4 and 1/17 M5 samples. The association with cytogenetic subtype was also nonrandom (P=0.0001). BAALC overexpression was seen in 2/2 inv(3)/t(3;3), 6/8 core binding factor leukemia samples, and 3/4 isolated trisomy 8 samples, but in 0/6 samples of t(15;17) and only 1/9 samples of t(11q23). Of 63 (19%) patients, 12 with normal karyotypes overexpressed BAALC. Overexpression of BAALC was an adverse prognostic factor. Among the 29 BAALC overexpressing patients, the median of event-free survival was 0.4 years compared with 1.2 years for the 73 patients that did not overexpress BAALC (P=0.006).

Example 5

BAALC Overexpression in AML Samples with Normal Cytogenetics

Real-time PCR (TaqMan®, Applied Biosystems) was used to quantify the relative levels of BAALC transcripts in AML samples with normal cytogenetics, using total RNA isolated from the cells in real-time PCR, as described in Example 2.

Patients evaluated were adults, diagnosed with de novo AML, enrolled in CALGB treatment protocol 9621 (see Proc. Natl. Acad. Sci. 98:13901-13906, 2001), and enrolled in a prospective cytogenetic companion study, CALGB 8461, with normal cytogenetics, more than 50% peripheral blasts, and sufficient RNA. All patients gave informed consent for treatment and blood samples. Patients received induction chemotherapy consisting of cytarabine, daunorubicin, and etoposide with or without the multi-drug resistance protein modulator, PSC-833. For patients with normal cytogenetics, this was followed by autologous peripheral blood stem cell transplantation (PBSCT). Maintenance therapy consisted of low-dose interleukin 2 interrupted with intermediate dose pulsing of interleukin 2.

Morphology according to the French-American-British (FAB) classification and karyotypes were centrally reviewed by CALGB. The FLT3 genotype was determined in 50 of the 51 AML patients. In addition, 35 of the 51 samples were analyzed for the partial tandem duplication (PTD) of the MLL gene.

Mononuclear cells from pretreatment blood samples were enriched by Ficoll-Hypaque gradient and frozen in liquid nitrogen. Control blood samples were obtained from 10 healthy, adult volunteers. Total RNA was extracted using Trizol (Invitrogen), and comparative real-time RT-PCR (TaqMan®) was performed in triplicate as previously described in Example 2 above. Briefly, the threshold cycles (CT) for BAALC and Glucose-phosphate isomerase (GPI) were determined, and the cycle number difference ($\Delta CT=GPI-BAALC$) was calculated for each replicate. Relative BAALC expression was calculated using the mean of $\Delta CT$ from the three replicates, that is $\mu(\Delta CT)=(\Sigma\Delta CT)/3$, and expressed as $2^{\mu(\Delta CT)}$. BAALC expression among 10 healthy donors ranged from 0 to 0.0042 with a mean of $0.00072\pm0.00151$ standard deviation (SD). A threshold level of 0.00525 (mean+3×SD) was used to dichotomize AML samples: samples were considered non-overexpressing for BAALC if $2^{\mu(\Delta CT)}$ was $\leq 0.00525$ ($MCT \leq -7.57$); samples were considered overexpressing for BAALC if $2^{\mu(\Delta CT)}$ was $>0.00525$ ($MC_T > -7.57$).

Samples from fifty-one adult patients were evaluated for BAALC overexpression by real-time RT-PCR. Samples from 7 patients (14%) were BAALC non-overexpressors (range of expression: 0-0.0034), and samples from 44 patients (86%) were BAALC overexpressors with expression ranging from 0.0057 to 8.2630. No significant differences were seen when comparing overexpressing and non-overexpressing patients with respect to age, white blood count (WBC), percentage of blasts, multiple other clinical features including treatment received, frequency of the MLL PTD and the FLT3 genotype (Table 1). Clinical features at presentation were compared using Fisher's Exact test or the Wilcoxon rank-sum test. Inferential tests yielding a p-value <0.05 were considered to be significant. All BAALC non-overexpressing patients had a wild-type (WT) $FLT3^{WT/WT}$ genotype (n=7), whereas a FLT3 internal tandem duplication (ITD) was present in 20 of the 43 BAALC overexpressing patients. Frequency of FAB subtypes M4/M5 versus other FAB subtypes was significantly lower in BAALC overexpressing patients (30%) compared to BAALC non-overexpressing patients (86%; P=0.009).

TABLE 1

Clinical characteristics at presentation for the BAALC non-overexpressing and BAALC overexpressing AML patients and impact of BAALC expression on clinical outcome.

| | BAALC non-overexpressors n = 7 | BAALC overexpressors n = 44 | p-value |
|---|---|---|---|
| Age (years) | | | |
| Median (Range) | 43 (23, 53) | 42 (20, 59) | 0.98 |
| Hemoglobin (g/dL) | | | |
| Median (Range) | 8.9 (6.4, 11.8) | 9.4 (4.6, 12.9) | 0.77 |
| Platelets (x 10⁹/L) | | | |
| Median (Range) | 50 (12, 144) | 54 (8, 235) | 0.74 |
| WBC (x 10⁹/L) | | | |
| Median (Range) | 45.5 (17.2, 146) | 42.7 (3.7, 295) | 0.97 |
| % Peripheral Blasts | | | |
| Median (Range) | 73 (51, 77) | 80 (52, 97) | 0.10 |
| % Bone marrow Blasts | | | |
| Median (Range) | 80 (58, 88) | 70 (38, 90) | 0.19 |
| FAB classification | | | |
| M0 | 0 (0%) | 1 (2%) | |
| M1 | 1 (14%) | 14 (33%) | |
| M2 | 0 (0%) | 15 (35%) | |
| M4 | 2 (29%) | 10 (23%) | |
| M5 | 4 (57%) | 3 (7%) | |
| AML unclassifiable | | 1 | |
| Gum Hypertrophy | 3 (43%) | 7 (16%) | 0.13 |
| Lymphadenopathy | 0 (0%) | 6 (14%) | 0.58 |
| Skin Infiltrates | 0 (0%) | 6 (14%) | 0.58 |
| Hepatomegaly | 1 (14%) | 3 (7%) | 0.46 |
| Splenomegaly | 0 (0%) | 5 (12%) | 1.00 |
| MLL PTD (35 cases analyzed) | | | |
| present | 0 (0%) | 1 (3%) | |
| absent | 6 (100%) | 28 (97%) | 1.00 |
| FLT3 genotype (50 cases analyzed) | | | |
| FLT3$^{WT/WT}$ | 7 (100%) | 23 (53%) | |
| FLT3$^{ITD/WT}$ | 0 (0%) | 12 (28%) | |
| FLT3$^{ITD/-}$ | 0 (0%) | 8 (19%) | 0.11 |
| Complete Remission | 7 (100%) | 35 (80%) | 0.33 |
| Disease-free Survival | | | |
| Median (years) | * | 0.7 | 0.009 |
| % Alive at 2 years (95% CI) | 100% | 39% (23%, 56%) | |
| Overall Survival | | | |
| Median (years) | * | 1.0 | 0.006 |
| % Alive at 2 years (95% CI) | 100% | 39% (24%, 53%) | |

*Not estimable, all patients censored for the outcome;
CI: confidence interval

Figure 16:
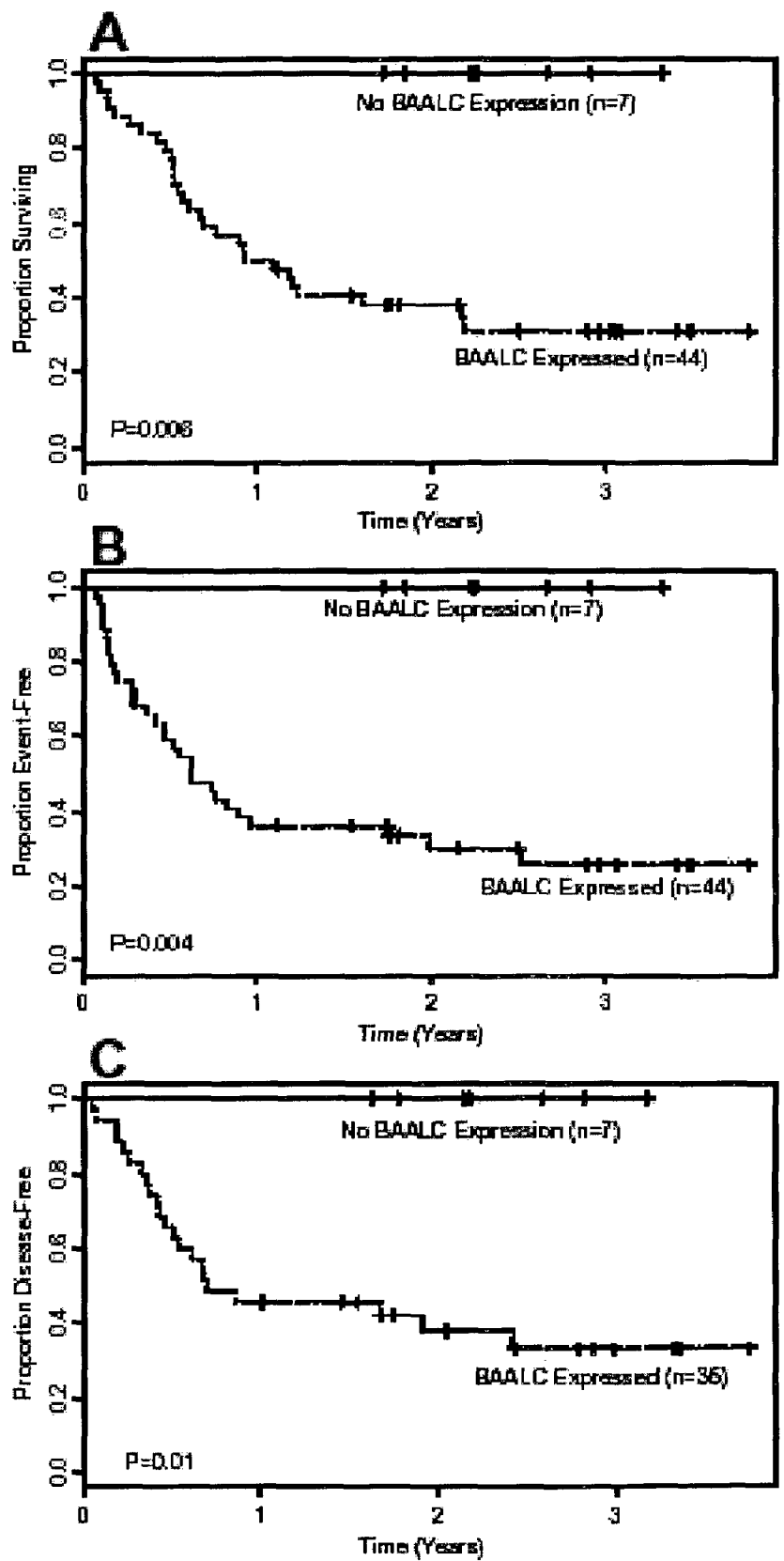
FIG. 16 shows the clinical outcome of adult de novo AML patients below 60 years of age from whom PB samples with more than 50% peripheral blasts, and centrally reviewed clinical data were available. Biological samples from 7 out of 51 patients (14%) either did not contain detectable BAALC transcripts or contained normal (i.e., not overexpressed) levels of BAALC transcripts. Biological samples from 44 out of 51 patients (86%) contained elevated (i.e., overexpressed) levels of BAALC transcripts, defined as having higher BAALC expression levels than found in any of 10 PB samples from normal individuals (i.e., patients not having leukemia). Panels A, B and C are Kaplan-Meier curves. The log-rank test was performed to determine whether there was a significant difference between the survival curves. (A) The median overall survival was 1.0 year (38% alive at 2 years) among the 44 positive patients compared with all 7 negative patients (100%) being alive at 2 years (censored for the outcome; P=0.006). (B) The median event-free survival for the 44 positive cases was 0.6 years (30% event-free at 2 years) compared with all 7 negative patients (100%) being event-free at 2 years (censored for the outcome; P=0.004). (C) The median disease-free survival for 35 positive cases (9 patients did not achieve complete remission) was 0.7 years (38% disease-free at 2 years) compared with all 7 negative patients (100%) being disease-free at 2 years (censored for the outcome; P=0.01).

Using these data, patient survival was calculated. There was a significant inverse correlation between BAALC overexpression and patient survival. Overall survival (OS) was measured from on-study date until date of death, regardless of cause of death, censoring for patients alive. With at least two years of follow-up, among the 44 BAALC overexpressing patients (overexpressors) the median overall survival was 1.0 year (38% alive at 2 years) compared with all 7 BAALC non-overexpressing patients (100%) being alive at 2 years (censored for the outcome; P=0.006; FIG. 16A). Event-free survival (EFS) was defined for those achieving complete remission (CR) as the time from on-study until relapse or death regardless of cause, censoring for those alive at last follow-up. If a patient did not achieve CR, but expired within 2 months of the on-study date, then EFS was defined as the time from on-study until death regardless of cause. Otherwise, EFS was set at 2 months. The median event-free survival for the 44 overexpressing cases was 0.6 years (30% event-free at 2 years) compared with all 7 non-overexpressing patients (100%) being event-free at 2 years (censored for the outcome; P=0.004; FIG. 16B). Disease-free survival (DFS) was defined only for patients achieving complete remission (CR) and was measured from the documented date of CR until date of relapse or death, regardless of cause, censoring for patients alive and in continuous CR. The median disease-free survival for 35 overexpressing cases (9 patients did not achieve complete remission) was 0.7 years (38% disease-free at 2 years) compared with all 7 non-overexpressing patients (100%) being disease-free at 2 years (censored for the outcome; P=0.01; FIG. 16C). OS, EFS and DFS were analyzed using the Kaplan-Meier method and the log-rank test was used to compare differences between survival curves.

The impact of other prognostic factors on OS and DFS was evaluated. Percentage of circulating blasts was significantly related to outcome (OS: P=0.01; DFS: P=0.02). Additionally, OS and DFS varied significantly across FLT3 genotype (OS: P=0.009; DFS: P=0.002). Because BAALC non-overexpressing patients were all censored for outcome, Cox proportional hazards models could not be used to adjust simultaneously for multiple independent prognostic factors. Therefore, restriction was used as a means of investigating the prognostic impact of BAALC expression, since confounding cannot occur if the prognostic factors do not vary across the two groups.

In an analysis restricted to patients with <77% circulating blasts (i.e. including all BAALC non-overexpressing patients), BAALC overexpressing patients had a significantly worse outcome than BAALC non-overexpressing patients [alive at 2 years (95% confidence intervals, CI): 53% (30%, 75%) vs 100%, P=0.038; disease-free at 2 years (95% CI): 56% (32%, 81%) vs 100%, P=0.0497]. In an analysis restricted to patients with the $FLT3^{WT/WT}$ genotype, the 7 BAALC non-overexpressing patients remained alive and disease-free, whereas the 23 BAALC overexpressing patients showed a significantly inferior outcome [alive at 2 years (95% CI): 52% (32%, 73%), P=0.01; disease-free at 2 years (95% CI): 53% (29%, 77%), P=0.03]. Thus BAALC expression identifies high-risk patients within the prognostically favorable $FLT3^{WT/WT}$ genotype group that fail to achieve long-term survival. Since FAB subtype differed significantly between BAALC overexpressing and BAALC non-overexpressing patients, an analysis restricted to patients with FAB subtypes M4/M5 was conducted. BAALC overexpressing patients showed a significantly inferior outcome [alive at 2 years: 31% (95% CI: 6%, 56%), P=0.01; disease-free at 2 years: 36% (95% CI: 8%, 65%), P=0.02] compared to BAALC non-overexpressing patients, indicating that the prognostic importance of BAALC expression is not accounted for by FAB subtype.

Example 6

BAALC Overexpression in CML Samples

Real-time PCR (TaqMan®, Applied Biosystems) was used to quantify the relative levels of BAALC transcripts in CML, using total RNA isolated from the cells in real-time PCR, as described in Example 2. Samples of leukocytes were obtained from eight patients with chronic phase CML. Samples of leukocytes were also obtained from eight patients with CML in blast crisis. Six out of the eight patients in blast crisis had BAALC levels that were statistically significantly higher than BAALC levels in the eight patients in the chronic phase of CML.

Example 7

Generation of Polyclonal Antibodies Specific for BAALC

Polyclonal antibodies immunoreactive for BAALC were made by injection of peptide antigens into rabbits using standard techniques well known in the art. One peptide antigen, DAIEPRYYESWTRETEST (SEQ ID NO:35), was used to make the polyclonal antibody GN2214. Another peptide antigen, DSIQQMDRSRRITK (SEQ ID NO:36), was used to make the polyclonal antibody GN2216. Approximately 10 mg of each peptide was synthesized using standard methods. Each peptide was conjugated to either KLH or BSA (2-3 mg) and the conjugate was purified using gel filtration. The conjugated peptides were injected subcutaneously into rabbits. The initial injection (day 0) was in complete Freund's adjuvant and all subsequent immunizations (days 14, 28, 42, 56 and 70) were given in incomplete Freund's adjuvant. Sera was collected on days 49, 63 and 77. Antibodies were purified from the sera using standard methods.

Example 8

Histochemical Analysis of Prostate Cancer

Immunohistochemistry was performed on human prostate cancer tissue sections using the anti-human BAALC-specific antibody, GN2214, generated as described in Example 7 above. Formalin-fixed, paraffin-embedded tissue blocks were used as the tissue source. Control tissue was also available and processed as was the tumor tissue. Five-micron sections were from the paraffin-embedded tumor specimens and mounted on polylysine-coated slides. The sections were deparaffinized in xylene and hydrated through alcohols to saline. Slides were incubated with GN2214 at various dilutions, overnight at 4° C. and then subsequently washed in phosphate-buffered saline (PBS). The slides were then incubated with goat anti-rabbit antibody which was conjugated to fluorescein and also washed in PBS. The slides were visualized under a fluorescence microscope. More intense staining was observed in tissue samples from the majority of prostate cancers as compared to control, non-cancerous tissue.

Example 9

Generation of a Monoclonal Antibody Specific for BAALC Proteins

A monoclonal antibody is made using standard hybridoma techniques that are well known in the art. Briefly, the peptide RADAIEPRYYESWTRETESTWLTYT (SEQ ID NO:37) was injected into BALB/c mice with complete Freund's adjuvant. Two weeks later, a second immunization with the peptide in incomplete Freund's adjuvant is given. Five days before fusion, a third immunization with the peptide, absent adjuvant is given. Mice are sacrificed and the spleens are dissected. Spleen cells are dispersed and then fused to SP2/0 cells using 50% PEG. Fused cells are selected in medium containing HAT. Individual clones are expanded and supernatant is tested for antibodies reactive with BAALC protein.

What is claimed is:

1. A method for characterizing acute myelogenous leukemia (AML) in a patient with AML, comprising assaying for overexpression of one or more BAALC transcripts in cells obtained from the patient,
    wherein the BAALC transcripts are selected from the group consisting of transcripts identified as 1-8, 1-6-8, 1-5-6-8, 1-4-5-6-8, 1-5-6-7-8, 1-2-6-8, 1-2-5-6-8, and 1-2-3-6-8; and
    wherein overexpression of one or more of the BAALC transcripts in cells of the patient indicates that the patient has an aggressive form of AML.

2. The method of claim 1 wherein overexpression of one or more of the BAALC transcripts in the patient's cells is assayed using a reverse-transcriptase polymerase chain reaction (RT-PCR).

3. The method of claim 2 wherein the RT-PCR employs a primer set selected from the group consisting of:
    i) a forward primer having a sequence that is identical to a sequence in the sense strand of exon 6 of the BAALC gene and a reverse primer having a sequence that is complementary to a sequence in the sense strand of exon 8 of the BAALC gene, ii) a forward primer having a sequence that is identical to a sequence in the sense strand of exon 8 of the BAALC gene and a reverse primer that is complementary to a sequence in the sense strand of exon 8 of the BAALC gene, and iii) a forward primer having a sequence that is identical to a sequence in the sense strand of exon 1 of the BAALC gene and a reverse primer that is complementary to a sequence in the sense strand of exon 1 of the BAALC gene.

4. The method of claim 2 wherein the RT-PCR is real-time RT-PCR.

5. The method of claim 4 wherein the real-time RT-PCR employs a probe that is complementary to a sequence within the product of the real-time RT-PCR, and wherein the probe has a reporter dye on end thereof and a quencher dye on another end thereof.

6. The method of claim 1 wherein the cells are blood cells of the patient.

7. The method of claim 1 wherein the AML patient has normal cytogenetics.

8. A method for characterizing chronic myelogenous leukemia (CML) in a patient with CML, comprising assaying for overexpression of one or more BAALC transcripts in cells obtained from the patient, wherein the BAALC transcripts are selected from the group consisting of transcripts identified as 1-8, 1-6-8, 1-5-6-8, 1-4-5-6-8, 1-5-6-7-8, 1-2-6-8, 1-2-5-6-8, and 1-2-3-6-8; and wherein overexpression of one or more of the BAALC transcripts in cells of the patient indicates that the patient is in blast crises.

9. The method of claim 8 wherein the assay comprises determining the levels of one or more of the BAALC transcripts in leukocytes obtained from the patient.

10. The method of claim 2 wherein the RT-PCR employs a primer set selected from the group consisting of:
   i) a forward primer whose sequence comprises SEQ ID NO. 26 and a reverse primer whose sequence comprises SEQ ID NO. 23;
   ii) a forward primer whose sequence comprises SEQ ID NO. 27 and a reverse primer whose sequence comprises SEQ ID NO. 23; and
   iii) a forward primer whose sequence comprises SEQ ID NO. 28 and a reverse primer whose sequence comprises SEQ ID NO. 29.

11. The method of claim 5 wherein the probe is selected from the group consisting of SEQ ID NO:32 and SEQ ID NO:33.

* * * * *

UNITED STATES PATENT AND TRADEMARK OFFICE
CERTIFICATE OF CORRECTION

| | | |
|---|---|---|
| PATENT NO. | : 7,455,995 B2 | Page 1 of 1 |
| APPLICATION NO. | : 10/293239 | |
| DATED | : November 25, 2008 | |
| INVENTOR(S) | : Tanner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1267 days.

Signed and Sealed this
Eleventh Day of January, 2011

David J. Kappos
*Director of the United States Patent and Trademark Office*

SEQUENCE LISTING

<160> NUMBER OF SEQ ID NOS: 39

<210> SEQ ID NO 1
<211> LENGTH: 343
<212> TYPE: DNA
<213> ORGANISM: Homo sapiens

<400> SEQUENCE: 1

```
gagagggccc ggactagggg cggcgggcac cgcaggagct ccgcgcggct gcagcgcggg      60
cgggagcggg gacgcgatgt cgccgccgcc gcctccttgc gggccggggc tgcgcctccg     120
gggctgagcc gccgccagag ccgacagccg agcagccgct gggcgctccc gcggcgcagg     180
aggatgggct gcggcgggag ccgggcggat gccatcgagc cccgctacta cgagagctgg     240
acccgggaga cagaatccac ctggctcacc tacaccgact cggacgcgcc gcccagcgcc     300
gccgcgccgg acagcggccc cgaagcgggc ggcctgcact cgg                       343
```

<210> SEQ ID NO 2
<211> LENGTH: 105
<212> TYPE: DNA
<213> ORGANISM: Homo sapiens

<400> SEQUENCE: 2

```
cccattaccc tcttgccttt gcacttgcct ggagagacaa cagtttaggg gctctgctgg      60
ttcaagaagg actgtgcagg tagcatggcc acacaccatg tacag                     105
```

<210> SEQ ID NO 3
<211> LENGTH: 147
<212> TYPE: DNA
<213> ORGANISM: Homo sapiens

<400> SEQUENCE: 3

```
gttctggtgc ttaggagtgg acatctttgg gaccgagggt tattctgcct tcctaccatg      60
tcaccagagt tgtgctaata cacagagagc ttcaggggat gagatctgcc attcattgag     120
caccttctgt gcggcagaca gtgttag                                         147
```

<210> SEQ ID NO 4
<211> LENGTH: 71
<212> TYPE: DNA
<213> ORGANISM: Homo sapiens

<400> SEQUENCE: 4

```
ggtgccttga ggaacattac catctgactg ccctacagaa agttgggcat cccaaccatt      60
gatttaaaaa g                                                           71
```

<210> SEQ ID NO 5
<211> LENGTH: 105
<212> TYPE: DNA
<213> ORGANISM: Homo sapiens

<400> SEQUENCE: 5

```
ttctggaggc tgagaagtcc aagatcaagg caccaacaga ttcagtgtct gatgaaggct      60
tgttctctgc ttcaaagatg gcacctcttg ctgtgttctc acatg                     105
```

<210> SEQ ID NO 6
<211> LENGTH: 167
<212> TYPE: DNA
<213> ORGANISM: Homo sapiens

<400> SEQUENCE: 6

```
gcatgctgga agatggactg ccctccaatg gtgtgccccg atctacagcc ccaggtggaa    60
tacccaaccc agagaagaag acgaactgtg agacccagtg cccaaatccc cagagcctca   120
gctcaggccc tctgacccag aaacagaatg gccttcagac cacagag                167
```

<210> SEQ ID NO 7
<211> LENGTH: 90
<212> TYPE: DNA
<213> ORGANISM: Homo sapiens

<400> SEQUENCE: 7

```
gttctgctgc cttcctaatg tctgatcttc tatctgaagt tcaagttgaa aagcaacaac    60
tccttttggc actcgataca aactcccagg                                    90
```

<210> SEQ ID NO 8
<211> LENGTH: 2317
<212> TYPE: DNA
<213> ORGANISM: Homo sapiens

<400> SEQUENCE: 8

```
gctaaaagag atgctaagag aatgcctgca aagaagtca ccattaatgt aacagatagc     60
atccaacaga tggacagaag tcgaagaatc acaaagaact gtgtcaacta gcagagagtc   120
caagcagaag ggcagatgga cttcttcagt gtccttcacg gcactggatc ccatcaaaga   180
accttgaaga agtggctgcc ccttgctgga cctgaattct actgagtccc tgcaagact    240
gtcttacctg gcagcaaact gctgcctgat tgttgggac cttctgagcc ttctacttat    300
catgtaaatg tattggcaca gtgcttacat atgttaataa actgcaaatg tgcagttcag   360
tttgtctctt tgcaactcct gtaatacggt ctggtgtaaa agtagtgagt taaagctaca   420
ggtcagttta tgaaacagaa aagtaggaat gcattttctg ggtgaaagag tcacacctta   480
gtgctataac tctcctgccc atgatagtgt attctgtttc aggcaagctt attctttcct   540
tctttcattt taaatattgt cattacaaat cttaccaggt tcacttaaaa gctggctttc   600
atccaactct aaacccacat attgaaaaaa tcaaggtaca ggaaaactcc ttgttatcct   660
tgtttcctta gctggtatg agacagatcg gatccagttt cccatgcacc aacccactgc    720
ccatggcatg tctttgggag gtgtctgtga agcagtcata cctgctcctc atctgcctgg   780
aaagtcctcc tattccagtg tccatgttgg cctccagtcc ttaatgtcac catgcttgtg   840
gccaatgcat ccaaataagg ataccctca gggctcagct agacattgca attttgcata    900
gctttccagt tccctttgct tgtcttcttg actgtcttcc ctctctatcg ggtcacttg    960
caattgttaa tcaaagattg aacactgcgt aggagaggga gatgatccag agacatgtgg  1020
cagcaggcat ggcttcccct tggcctctct gtacactgcc ccaggactgt cattttggca  1080
tctgcaaagg aatcacttta gaaagccagc acctggttga tgtgtattca tactgacatt  1140
agattgatgt gcactgcatt agaaatgagg tagctgacac agaaaaagga tgttttgata  1200
ggaataattt tctagtatgt cttgaaacat gttcatctgg aagtattttc ctccaaagta  1260
atgtagcatg attttcaag gattgttaac atgcctggga ttgggaaaga taggactaaa   1320
gttgtgccaa actatatcaa taaattccat gtttagcaga aataggcagc ctattggtgt  1380
tatgtttatg taacatagtc cagagaactg acatgcaggt caaaagtcag atacgcaacc  1440
tccttatctg ctaactctgt tattcttcaa acacaacgtg ggtagtgtca tttttccttc  1500
```

-continued

```
cttccttcca ttggcagatt gtatatttat tcacaaaaca ttaaatgtcc atcctgtgcc      1560
aggtactatg cagatgttga gggatttggg gtctggttag tcgtgactat ctatcctgaa      1620
tctaacagtg acttcataac taggagactg aattagaccc ttaaggtata gtgtgtgttg      1680
caaatcactc tgcaatggaa acttttatat tcagggtagg tttgtgtctt aaactaggtg      1740
ttctaatcaa tgtacaagac tttaccatac acgcaactat agttttttcta aaccttcatc     1800 attttgtgat tctttgagaa agggctttta ggaactttat gttctaaaaa atgttttaa       1860 caataataag ataaaagaaa aacctgtgat tcatatgtcc ccactggcat tactcagcag      1920
gagcccccag ctgccaaagg ttggcagtga tcctgcaagt tcaagggctc tttctccctg      1980
gggatgtgct ttgtggcttc tctttacagc tttgtttctg catcagttca ctgctgcatg      2040
ttgtttggaa tttatcacct taagaaagtg tctctgtttt atatagaaac actttctcac      2100
ttacagggga gaaggaaatg cagggcacat gatctggccc tccccagaac aatctggatt      2160
tcacggagac agcaaccaga agttaaacca tgtgactaaa aatgcatctg gctacttttt      2220
catgtatgta tgagacagaa actaatcctt actatcctat taggatacca ctttttcattg     2280 caaagtttgt gtcaataaag tcattaattt taaacat                               2317
```

<210> SEQ ID NO 9
<211> LENGTH: 2826
<212> TYPE: RNA
<213> ORGANISM: Homo sapiens

<400> SEQUENCE: 9

```
gagagggccc ggacuagggg cggcgggcac cgcaggagcu ccgcgcggcu gcagcgcggg       60
cgggagcggg gacgcgaugu cgccgccgcc gccuccuugc gggccggggc ugcgccuccg      120
gggcugagcc gccgccagag ccgacagccg agcagccgcu gggcgcuccc gcggcgcagg      180
aggaugggcu gcggcgggag ccgggcggau gccaucgagc cccgcuacua cgagagcugg      240
acccgggaga cagaauccac cuggcucacc uacaccgacu cggacgcgcc gcccagcgcc      300
gccgcgccgg acagcggccc cgaagcgggc ggccugcacu cgggcaugcu ggaagaugga      360
cugcccucca augugugcc ccgaucuaca gcccaggug gaauacccaa cccagagaag        420
aagacgaacu gugagaccca gugcccaaau ccccagagcc ucagcucagg cccucugacc      480
cagaaacaga augccuuca gaccacagag gcuaaaagag augcuaagag aaugccugca      540
aaagaaguca ccauuaaugu aacagauagc auccaacaga uggacagaag ucgaagaauc      600
acaaagaacu gugucaacua gcagagaguc caagcagaag ggcagaugga cuucuucagu      660
guccuucacg gcacuggauc ccaucaaaga accuugaaga aguggcugcc ccuugcugga      720
ccugaauucu acugaguccc uggcaagacu gucuuaccug gcagcaaacu gcugccugau      780 uuguuggac cuucugagcc uucuacuuau cauguaaaug uauuggcaca gugcuuacau      840 auguaauaa acugcaaaug ugcaguucag uuugucucuu ugcaacuccu guaauacggu      900
cugguguaaa aguagugagu uaaagcuaca ggucaguuua ugaaacagaa aguaggaau       960 gcauuuucug ggugaaagag ucacaccuua ugcucuauaac ucuccugccc augauagugu    1020
auucuguuuc aggcaagcuu auucuuuccu ucuuucauuu uaaauauugu cauuacaaau    1080
cuuaccaggu ucacuaaaa gcuggcuuuc auccaacucu aaacccacau auugaaaaaa    1140
ucaagguaca ggaaaacucc uuguuauccu uguuccuua gcuggguaug agacagaucg      1200
gauccaguuu cccaugcacc aacccacugc ccauggcaug ucuuuggag ugucucuguga   1260 agcagucaua ccugcuccuc aucugccugg aaagccucuc uauuccagug uccauguugg   1320
```

-continued

| | |
|---|---|
| ccuccagucc uuaaugucac caugcuugug gccaaugcau ccaaauaagg auacccucuca | 1380 |
| gggcucagcu agacauugca auuuugcaua gcuuccagu ucccuuugcu ugucuucuug | 1440 |
| acugucuucc cucucuaucg gggucacuug caauuuuaau caaagauuga acacugcgua | 1500 |
| ggagagggag augauccaga gacauguggc agcaggcaug gcuucccuu ggccucucug | 1560 |
| uacacugccc caggacuguc auuuuggcau cugcaaagga aucacuuuag aaagccagca | 1620 |
| ccugguugau guguauucau acgacauua gauugaugug cacugcauua gaaaugaggu | 1680 |
| agcugacaca gaaaaggau guuugauag gaauaauuuu cuaguaugu uugaaacaug | 1740 |
| uucaucugga aguauuuucc uccaaaguaa uguagcauga uuuucaagg auuguuaaca | 1800 |
| ugccugggau ugggaaagau aggacuaaag uugugccaaa cuauaucaau aaauuccaug | 1860 |
| uuuagcagaa auaggcagcc uauuggguguu auguuuaugu aacauagucc agagaacuga | 1920 |
| caugcagguc aaaagucaga uacgcaaccu ccuuaucugc uaacucuguu auucuucaaa | 1980 |
| cacaacuggg guagugucau uuuccuucc uuccuuccau uggcagauug uauauuuauu | 2040 |
| cacaaaacau uaaaugucca uccugugcca gguacauugc agauguugag ggauuugggg | 2100 |
| ucugguuagu cgugacuauc uauccugaau cuaacaguga cuucauaacu aggagacuga | 2160 |
| auuagacccu uaagguauag ugugugguugc aaaucacucu gcaauggaaa cuuuuauauu | 2220 |
| cagggauaggu uugugucuua aacuaggugu ucuaaucaau guacaagacu uuaccauaca | 2280 |
| cgcaacuaua guuuucuaa accuucauca uuuugugau cuuugagaaa gggcuuuuag | 2340 |
| gaacuuuaug uucuaaaaaa uguuuuuaac aauaauaaga uaaagaaaa accugugauu | 2400 |
| cauaugucc cacuggcauu acucagcagg agcccccagc ugccaaaggu uggcagugau | 2460 |
| ccugcaaguu caagggcucu uucucccugg ggaugugcuu uguggcuucu cuuuacagcu | 2520 |
| uuguuucugc aucaguucac ugcugcaugu uguuggaau uuaucaccuu aagaaagugu | 2580 |
| cucuguuuua uauagaaaca cuuucucacu uacaggggag aaggaaaugc agggcacaug | 2640 |
| aucuggcccu ccccagaaca aucuggauuu cacggagaca gcaaccagaa guuaaaccau | 2700 |
| gugacuaaaa augcaucugg cuacuuuuuc auguauguau gagacagaaa cuaauccuua | 2760 |
| cuauccuauu aggauaccac uuuucauugc aaaguuugug ucaauaaagu cauuaauuuu | 2820 |
| aaacau | 2826 |

<210> SEQ ID NO 10
<211> LENGTH: 2660
<212> TYPE: RNA
<213> ORGANISM: Homo sapiens

<400> SEQUENCE: 10

| | |
|---|---|
| gagagggccc ggacuagggg cggcgggcac cgcaggagcu ccgcgcggcu gcagcgcggg | 60 |
| cgggagcggg gacgcgaugu cgccgccgcc gccuccuugc gggccggggc ugcgccuccg | 120 |
| gggcugagcc gccgccagag ccgacagccg agcagccgcu gggcgcuccc gcggcgcagg | 180 |
| aggaugggcu gcggcgggag ccgggcggau gccaucgagc cccgcuacua cgagagcugg | 240 |
| acccgggaga cagaauccac cuggcucacc uacaccgacu cggacgcgcc gcccagcgcc | 300 |
| gccgcsccgg acagcggccc cgaagcgggc ggccugcacu cgggcuaaaa gagaugcuaa | 360 |
| gagaaugccu gcaaaagaag ucaccauuaa uguaacagau agcauccaac agauggacag | 420 |
| aagucgaaga aucacaaaga acugucaa cuagcagaga guccaagcag aagggcagau | 480 |
| ggacuucuuc agugucuuc acggcacugg aucccaucaa agaaccuuga agaaguggcu | 540 |

```
gccccuugcu ggaccugaau ucuacugagu cccuggcaag acugucuuac cuggcagcaa       600
acugcugccu gauuuguugg gaccuucuga gccuucuacu uaucauguaa auguauuggc       660
acagugcuua cauauguuaa uaaacugcaa augugcaguu caguuugucu cuuugcaacu       720
ccuguaauac ggucuggugu aaaaguagug aguuaaagcu acaggucagu uaugaaaca        780 gaaaaguagg aaugcauuuu cugggugaaa gagucacacc uuagugcuau aacucuccug       840
cccaugauag uguauucugu ucaggcaag  cuuauucuuu ccuucuuuca uuuuaaauau       900
ugucauuaca aaucuuacca gguucacuua aaagcuggcu ucauccaac  ucuaaaccca       960 cauauugaaa aaaucaaggu acaggaaaac uccuuguuau ccuguuuccu uuagcuuggu      1020
augagacaga ucggauccag uuucccaugc accaacccac ugcccauggc augucuuugg      1080
gaggugucug ugaagcaguc auaccugcuc cucaucugcc uggaaaaguc uccuauucca      1140
guguccaugu uggccuccag uccuuaaugu caccaugcuu guggccaaug cauccaaaua      1200
aggauacccc ucagggcuca gcuagacauu gcauuuugc  auagcuuucc aguucccuuu      1260
gcuugucuuc uugacugucu ucccucucua ucggggucac uugcaauugu aaucaaaga       1320 uugaacacug cguaggagag ggagaugauc cagagacaug uggcagcagg cauggcuucc      1380
ccuuggccuc ucuguacacu gccccaggac ugucauuuug gcaucugcaa aggaaucacu      1440
uuagaaagcc agcaccuggu ugauguguau ucauacugac auuagauuga ugugcacugc      1500
auuagaaaug agguagcuga cacagaaaaa ggauguuuug uaggaauaa  uuuucuagua      1560 ugucuugaaa cauguucauc uggaaguauu uccuccaaa  guaauguagc augauuuuuc      1620
aaggauuguu aacaugccug ggauugggaa agauaggacu aaaguugugc caaacuauau      1680
caauaaauuc caugu uuagc agaaauaggc agccuauugg uguuauguuu auguaacaua      1740
guccagagaa cugacaugca ggucaaaagu cagauacgca accuccuuau cugcuaacuc      1800
uguuauucuu caaacacaac gugggu agugu ucauuuuucc uuccuuccuu ccauuggcag      1860
auuguauauu uauucacaaa acauuaaaug uccaccugu  gccagguacu augcagaugu      1920
ugagggauuu gggg gucuggu uagucgugac uaucuauccu gaaucuaaca gugacuucau      1980
aacuaggaga cugaauuaga cccuuaaggu auagugugug uugcaaauca cucugcaaug      2040
gaaacuuuua uauucaggu  agguuugugu cuuaaacuag guguucuaau caauguacaa      2100
gacuuuacca uacacgcaac uauaguuuuu cuaaaccuuc aucauuuugu gauucuuuga      2160
gaaagggcuu uuaggaacuu uauguucuaa aaaauguuuu uaacaauuau aagauaaaag      2220
aaaaaccugu gauucauaug uccccacugg cauuacucag caggagcccc cagcugccaa      2280
agguuggcag ugauccugca aguucaaggg cucuuucucc cuggggaugu gcuuugu ggc      2340 uucucuuuac agcuuuguuu cugcaucagu ucacugcugc auuguuuug  gaauuuauca      2400 ccuuaagaaa gugucucugu uuuauauaga aacacuuucu cacuuacagg ggagaaggaa      2460
augcagggca caugaucugg cccucccag  aacaaucugg auuucacgga gacagcaacc      2520
agaaguuaaa ccaugugacu aaaaaugcau cuggcuacuu uucauguau  guaugagaca      2580 gaaacuaauc cuuacuaucc uauuaggaua ccacuuuuca uugcaaaguu ugugucaaua      2640
aagucauuaa uuuuaaacau                                                 2660

<210> SEQ ID NO 11
<211> LENGTH: 2931
<212> TYPE: RNA
<213> ORGANISM: Homo sapiens

<400> SEQUENCE: 11
```

```
gagagggccc ggacuagggg cggcgggcac cgcaggagcu ccgcgcggcu gcagcgcggg      60
cgggagcggg gacgcgaugu cgccgccgcc gccuccuugc gggccggggc ugcgccuccg     120
gggcugagcc gccgccagag ccgacagccg agcagccgcu gggcgcuccc gcggcgcagg     180
aggaugggcu gcggcgggag ccgggcggau gccaucgagc cccgcuacua cgagagcugg     240
acccgggaga cagaauccac cuggcucacc uacaccgacu cggacgcgcc gcccagcgcc     300
gccgcsccgg acagcggccc cgaagcgggc ggccugcacu cgguucugga ggcugagaag     360
uccaagauca aggcaccaac agauucagug ucugaugaag gcuguucuc ugcuucaaag      420 auggcaccuc uugcugugu cucacauggc augcuggaag auggacugcc cuccaauggu      480
gugccccgau cuacagcccc aggugggaau acccaacccag agaagaagac gaacugugag     540
acccagugcc caaauccca gagccucagc ucaggcccuc ugacccagaa acagaauggc     600
cuucagacca cagaggcuaa aagagaugcu aagagaaugc cugcaaaaga agucaccauu     660
aauguaacag auagcaucca acagauggac agaagucgaa gaaucacaaa gaacuguguc     720
aacuagcaga gaguccaagc agaagggcag auggacuucu ucagugugccu ucacggcacu     780 ggaucccauc aaagaaccuu gaagaagugg cugcccuug cuggaccuga auucuacuga      840
gucccuggca agacugucuu accuggcagc aaacugcugc cugauuuguu gggaccuucu     900
gagccuucua cuuaucaugu aaauguauug gcacagugcu acauauguu aauaaacugc      960 aaaugugcag uucaguuugu cucuuugcaa cuccuguaau acggucuggu guaaaaguag    1020
ugaguuaaag cuacagguca guuuaugaaa cagaaaagua ggaaugcauu ucgggguga      1080 aagagucaca ccuuagugcu auaacucucc ugcccaugau aguguauucu guuucaggca    1140
agcuuauucu uuccuucuuu cauuuuaaau auugucauua caaaucuuac cagguucacu    1200
uaaaagcugg cuuucaucca acucuaaacc cacauauuga aaaaaucaag guacaggaaa    1260
acuccuuguu auccuguuu ccuuagcuug guaugagaca gaucggaucc aguuucccau     1320
gcaccaaccc acugcccaug gcaugucuuu gggaggguguc ugugaagcag ucauaccugc    1380
uccucaucug ccuggaaagu ccuccuauuc cagugccauu guuggccucc aguccuuaau     1440
gucaccaugc uuguggccaa ugcauccaaa uaaggauacc ccucagggcu cagcuagaca    1500
uugcaauuuu gcauagcuuu ccaguuccu ugcuugucu ucuugacugu cuucccucuc      1560 uaucggggguc acuugcaauu guuaaucaaa gauugaacac ugcguaggag agggagauga    1620
uccagagaca guguggcagca ggcauggcuu cccuuggcc ucucuguaca cugccccagg     1680
acugucauuu uggcaucugc aaaggaauca cuuuagaaag ccagcaccug guugaugugu    1740
auucauacug acauuagauu gaugugcacu gcauugaaaa ugaguagcu gacacagaaa     1800 aaggauguuu ugauaggaau aauuuucuag uaugucuuga aacauguuca ucuggaagua    1860
uuuuccucca aaguaaugua gcaugauuuu caaggauugu uuaacaugcc ugggauuggg    1920
aaagauagga cuaaaguugu gccaaacuau aucaauaaau uccauguuua gcagaaauag    1980
gcagccuauu ggguguaugu uuauguaaca uagccagag aacugacaug cagguacaaaa     2040 gucagauacg caaccuccuu aucugcuaac ucuguauuc uucaaacaca acguggguag     2100
ugucauuuuu ccuuccuucc uuccauuggc agauuguaua uuuauucaca aaacauuaaa    2160
uguccauccu gugccaggua cuaugcagau guugagggau uggggucug uuagucgug      2220 acuaucuauc cugaaucuaa cagugacuuc auaacuagga gacugaauua gacccuuaag    2280
guauagugug uguugcaaau cacucugcaa uggaaacuuu uauauucagg guagguuugu    2340
```

-continued

| | |
|---|---|
| gucuuaaacu aggvguucua aucaauguac aagacuuuac cauacacgca acuauaguuu | 2400 |
| uucuaaaccu ucaucauuuu gugauucuuu gagaaagggc uuuuaggaac uuuauguuca | 2460 |
| aaaaauguuu uuaacaauaa uaagauaaaa gaaaaaccug ugauucauau gucccccacug | 2520 |
| gcauuacuca gcaggagccc ccagcugcca aagguuggca gugauccugc aaguucaagg | 2580 |
| gcucuuucuc ccuggggaug ugcuuugugg cuucucuuua cagcuuuguu ucugcaucag | 2640 |
| uucacugcug cauguuguuu ggaauuuauc accuuaagaa agugucucug uuuuauauag | 2700 |
| aaacacuuuc ucacuuacag gggagaagga aaugcagggc acaugaucug gcccuccccca | 2760 |
| gaacaaucug gauuucacgg agacagcaac cagaaguuaa accaugugac uaaaaaugca | 2820 |
| ucuggcuacu uuuucaugua uguaugagac agaaacuaau ccuuacuauc cuauuaggau | 2880 |
| accacuuuuc auugcaaagu uuguguaau aaagucauua auuuuaaaca u | 2931 |

<210> SEQ ID NO 12
<211> LENGTH: 3003
<212> TYPE: RNA
<213> ORGANISM: Homo sapiens

<400> SEQUENCE: 12

| | |
|---|---|
| gagagggccc ggacuagggg cggcgggcac cgcaggagcu ccgcgcggcu gcagcgcggg | 60 |
| cgggagcggg gacgcgaugu cgccgccgcc gccuccuugc gggccggggc ugcgccuccg | 120 |
| gggcugagcc gccgccagag ccgacagccg agcagccgcu gggcgcuccc gcggcgcagg | 180 |
| aggaugggcu gcggcgggag ccgggcggau gccaucgagc cccgcuacua cgagagcugg | 240 |
| acccgggaga cagaauccac cuggcucacc uacaccgacu cggacgcgcc gcccagcgcc | 300 |
| gccgcsccgg acagcggccc cgaagcgggc ggccugcacu cggggugccu ugaggaacau | 360 |
| uaccaucuga cugcccuaca gaaaguuggg cauccccaacc auugauuuaa aaaguucugg | 420 |
| aggcugagaa guccaagauc aaggcaccaa cagauucagu gucugaugaa ggcuuguucu | 480 |
| cugcuucaaa gauggcaccu cuugcugugu ucucacaugg caugcuggaa gauggacugc | 540 |
| ccuccaaugg ugugccccga ucuacagccc cagguggaau acccaaccca gagaagaaga | 600 |
| cgaacuguga gacccagugc ccaaauccc agagccucag cucaggcccu cugacccaga | 660 |
| aacagaaugg ccuucagacc acagaggcua aagagaugc uaagagaaug ccugcaaaag | 720 |
| aagucaccau uaauguaaca gauagcaucc aacagaugga cagaagucga agaaucacaa | 780 |
| agaacugugu caacuagcag agaguccaag cagaagggca gauggacuuc uucagugucc | 840 |
| uucacggcac uggaucccau caaagaaccu ugaagaagug gcugcccuu gcuggaccug | 900 |
| aauucuacug aguccuggc aagacugucu uacuggcag caaacugcug ccugauuugu | 960 |
| ugggaccuuc ugagccuucu acuuaucaug uaaauguauu ggcacagugc uuacauaugu | 1020 |
| uaauaaacug caaaugugca guucagvuug ucucuuugca acuccuguaa uacggucugg | 1080 |
| uguaaaagua gugaguuaaa gcacaagguc aguuuaugaa acagaaaagu aggaaugcau | 1140 |
| uuucgggvug aaagagucac accuuagugc uauaacucuc cugcccauga uaguguauuc | 1200 |
| uguuucaggc aagcuuauuc uuuccuucuu ucauuuaaa uauugucauu acaaaucuua | 1260 |
| ccagguucac uuaaaagcug gcuuucaucc aacucuaaac ccacauauug aaaaaaucaa | 1320 |
| ggvacaggaa aacuccuugu uaccuuguu uccuuagcuu gguaugagac agaucggauc | 1380 |
| caguuucca ugcaccaacc cacugcccau ggcaugucuu ugggaggugu cugugaagca | 1440 |
| gucauaccug cuccucaucu gccggaaag uccuccuauu ccaguguccca uguuggccuc | 1500 |
| caguccuuaa ugucaccaug cuuguggcca augcauccaa auaaggauac ccccucagggc | 1560 |

```
ucagcuagac auugcaauuu ugcauagcuu uccaguuccc uuugcuuguc uucuugacug    1620
ucuucccucu cuaucggggu cacuugcaau uguuaaucaa agauugaaca cugcguagga    1680
gagggagaug auccagagac auguggcagc aggcauggcu uccccuuggc cucucuguac    1740
acugccccag acugucauu uggcaucug caaaggaauc acuuuagaaa gccagcaccu     1800
gguugaugug uauucauacu gacauuagau ugaugugcac ugcauuagaa augagguagc    1860
ugacacagaa aaaggauguu uugauaggaa uaauuucua guaugucuug aaacauguuc    1920
aucuggaagu auuuccucc aaaguaaugu agcaugauuu ucaaggauu guuaacaugc     1980
cugggauugg gaaagauagg acuaaaguug ugccaaacua uaucaauaaa uccauguuu     2040
agcagaaaua ggcagccuau ugguguuaug uuuauguaac auaguccaga gaacugacau    2100
gcaggucaaa agucagauac gcaaccuccu uaucugcuaa cucuguuauu cuucaaacac    2160
aacgugggua gugucauuuu ccuuccuuc cuuccauugg cagauuguau auuuauucac     2220
aaacauuaa auguccaucc ugugccaggu acuaugcaga guugaggga uuggggucu      2280
gguuagucgu gacuaucuau ccugaaucua acagugacuu cauaacuagg agacugaauu    2340
agacccuuaa gguauagugu uguugcaaa ucacucugca auggaaacuu uuauauucag    2400
gguagguuug ugucuaaaac uagguguucu aaucaaugua caagacuuua ccauacacgc    2460
aacuauaguu uuucuaaacc uucaucauuu ugugauucu ugagaaaggg cuuuuaggaa    2520
cuuuauguuc uaaaaaaugu uuuuaacaau aauaagauaa agaaaaaacc ugugauucau    2580
auguccccac uggcauuacu cagcaggagc ccccagcugc caaagguugg cagugauccu    2640
gcaaguucaa gggcucuuuc ucccugggga ugugcuuugu ggcuucucuu uacagcuuug    2700
uuucugcauc aguucacugc ugcauguguu uuggaauuua ucaccuuaag aaaggucucu    2760
uguuuuauau agaaacacuu ucucacuuac aggggagaag gaaaaugcagg gcacaugauc    2820
uggcccuccc cagaacaauc uggauuucac ggagacagca accagaaguu aaaccaugug    2880
acuaaaaaug caucuggcua cuuuuucaug uaucuaugag acagaaacua auccuuacua    2940
uccuauuagg auaccacuuu ucauugcaaa guuuguguca auaaagucau uaauuuuaaa    3000
cau                                                                 3003

<210> SEQ ID NO 13
<211> LENGTH: 3022
<212> TYPE: RNA
<213> ORGANISM: Homo sapiens

<400> SEQUENCE: 13
gagagggccc ggacuagggg cggcgggcac cgcaggagcu ccgcgcggcu gcagcgcggg      60
cgggagcggg gacgcgaugu cgccgccgcc gccuccuugc gggccggggc ugcgccuccg     120
ggcugagcc gccgccagag ccgacagccg agcagccgcu gggcgcuccc gcggcgcagg     180
aggaugggcu gcgcgggag ccgggcggau gccaucgagc cccgcuacua cgagagcugg     240
acccgggaga cagaauccac cuggcucacc uacaccgacu cggacgcgcc gcccagcgcc    300
gccgcsccgg acagcggccc cgaagcgggc ggccugcacu cgguucugga ggcugagaag    360
uccaagauca aggcaccaac agauucagug ucgaugaag gcuuguucuc ugcuucaaag     420
auggcaccuc uugcuguguu cucacauggc augcuggaag auggacugcc cuccaauggu    480
gugcccgau cuacgccccc agguggaaua cccaacccag agaagaagac gaacugugag    540
acccagugcc caaaucccca gagccucagc ucaggccccuc ugaccagaa acagaauggc    600
```

```
cuucagacca cagagguucu gcugccuucc uaaugucuga ucuucuaucu gaaguucaag    660
uugaaaagca acaacuccuu uuggcacucg auacaaacuc ccagggcuaa aagagaugcu    720
aagagaaugc cugcaaaaga agucaccauu aauguaacag auagcaucca acagauggac    780
agaagucgaa gaaucacaaa gaacuguguc aacuagcaga gaguccaagc agaagggcag    840
auggacuucu ucagguccu ucacggcacu ggaucccauc aaagaaccuu gaagaagugg     900 cugcccuug cuggaccuga auucuacuga gucccuggca agacugucuu accuggcagc     960
aaacugcugc cugauuuguu gggaccuucu gagccuucua cuuaucaugu aaauguauug   1020
gcacagugcu acauaugu aauaaacugc aaaugucag uucaguuugu ucuuugcaa       1080 cuccuguaau acgucuggu guaaaaguag ugaguuaaag cuacagguca guuuaugaaa    1140
cagaaaagua ggaaugcauu ucugggguga aagagcacca ccuuagugcu auaacucucc   1200
ugcccaugau aguauaucu guuucaggca agcuuauucu uccuucuuu cauuuuaaau     1260 auugucauua caaaucuuac cagguucacu uaaaaagcugg cuuucauca acucuaaaccc 1320 cacauauuga aaaaaucaag guacaggaaa acuccuuguu auccuuguu ccuuagcuug    1380 guaugagaca gaucggaucc aguuucccau gcaccaaccc acugcccaug gcaugucuuu   1440
gggagguguc ugugaagcag ucauaccugc uccucaucug ccuggaaagu ccuccuauuc   1500
cagaguccau guuggccucc aguccuuaau gucaccaugc uuguggccaa ugcauccaaa   1560
uaaggauacc cccagggcu cagcuagaca uugcaauuuu gcauagcuuu ccaguucccu    1620
uugcuugucu ucuugacugu cuccccucuc uaucgggguc acuugcaauu guuaaucaaa   1680
gauugaacac ugcguaggag agggagauga uccagagaca uguggcagca ggcauggcuu   1740 cccccuuggcc ucucuguaca cugccccagg acugucauuu uggcaucugc aaaggaauca  1800
cuuuagaaag ccagcaccug guugaugugu auucauacug acauuagauu gaugugcacu   1860
gcauugaaaa ugagguagcu gacacagaaa aaggauguuu ugauaggaau aauuuuucuag 1920 uaugucuuga aacauguuca ucuggaagua uuuuccucca aguaaugua gcaugauuu     1980 ucaaggauug uuaacaugcc ugggauuggg aaagauagga cuaaaguugu gccaaacuau   2040
aucaauaaau uccauguuua gcagaaauag gcagccuauu ggguguaugu uuauguaaca   2100 uagucagag aacugacaug caggucaaaa gucagauacg caacuccuu aucgcuaac     2160 ucuguauuc uucaaacaca acgugggguag ugucauuuuu ccuuccuuuc uuccauuggc   2220
agauuguaua uuuauucaca aaacauuaaa uguccaaccu guugccaggua cuaugcagau  2280 guugagggau uggggucug guuagucgug acuaucuauc cugaaucaa caguuggacuuc  2340 auaacuagga gacugaauua gacccuuaag guauagugug uguugcaaau cacucugcaa   2400
uggaaacuuu uauauucagg guagguuugu gucuaaacu agguguucua aucaauguac    2460
aagacuuuac cauacacgca acuauaguu uucaaaccu ucaucauuuu gugauucuuu    2520
gagaaagggc uuuuaggaac uuuauguucu aaaaaauguu uuaacaaua auaagauaaa    2580 agaaaaaccu gugauucaua ugucccacu ggcauuacuc agcaggagcc cccagcugcc    2640
aaagguuggc agugauccug caaguucaag ggcucuuucu cccuggggau gugcuuugu    2700 gcuucucuuu acagcuuugu uucugcauca guucacugcu gcauguuguu uggaauuuau   2760
caccuuaaga aagugucucu guuuuauaua gaaaacuuuu ucacuuaca ggggagaagg    2820 aaaugcaggg cacaugaucu ggcccucccc agaacaauuc ggauuucacg gagacagcaa   2880
ccagaaguua aaccaugugu cuaaaaaugc aucggcuac uuuucaugu auguaugaga     2940 cagaaacuaa uccuuacuau ccuauuagga uaccacuuuu cauugcaaag uuugugucaa   3000
```

```
uaaagucauu aauuuuaaac au                                     3022

<210> SEQ ID NO 14
<211> LENGTH: 2932
<212> TYPE: RNA
<213> ORGANISM: Homo sapiens

<400> SEQUENCE: 14
gagagggccc ggacuagggg cggcgggcac cgcaggagcu ccgcgcggcu gcagcgcggg     60
cgggagcggg gacgcgaugu cgccgccgcc gccuccuugc gggccggggc ugcgccuccg    120
gggcugagcc gccgccagag ccgacagccg agcagccgcu gggcgcuccc gcggcgcagg    180
aggaugggcu gcggcgggag ccgggcggau gccaucgagc cccgcuacua cgagagcugg    240
acccgggaga cagaauccac cuggcucacc uacaccgacu cggacgcgcc gcccagcgcc    300
gccgcsccgg acagcggccc cgaagcgggc ggccugcacu cggcccauua cccucuugcc    360
uuugcacuug ccuggagaga caacaguuua ggggcucugc ugguucaaga aggacugugc    420
agguagcaug gccacacacc auguacaggc augcuggaag auggacugcc uccaauggu     480 gugccccgau cuacagcccc agguggaaua cccaacccag agaagaagac gaacugugag    540
acccagugcc caauccccca gagccucagc ucaggcccuc ugaccagaa acagaauggc     600 cuucagacca cagaggcuaa aagagaugcu aagagaaugc cugcaaaaga agucaccauu    660
aauguaacag auagcaucca acagauggac agaagucgaa gaaucacaaa gaacugguc     720 aacuagcaga gaguccaagc agaagggcag augggacuuc ucagguguccu ucacggcacu    780 ggaucccauc aaagaaccuu gaagaagugg cugccccuug cuggaccuga auucuacuga    840
gucccuggca agacugucuu accuggcagc aaacugcugc cugauugu ugggaccuucu     900 gagccuucua cuuaucaugu aaauguauug gcacagugcu uacauauguu aauaaacugc    960
aaaugugcag uucaguuugu ucucuuugcaa uccuguaau acggucuggu guaaaaguag   1020
ugaguuaaag cuacaggu ca guuaugaaa cagaaaagua ggaaugcauu uucuggguga    1080
aagagucaca ccuuagugcu auaacucucc ugcccaugau aguguauucu guuucaggca    1140
agcuuauucu uccuucuuu cauuuuaaau auugucauua caaucuuac cagguucacu     1200 uaaaagcugg cuuucaucca acucuaaacc cacauauuga aaaaaucaag guacaggaaa    1260
acuccuuguu auccuuguuu ccuuagcuug guaugagaca gaucggaucc aguucccau     1320 gcaccacccc acugcccaug gcaugucuuu ggggaggugu ugugaagcag ucauaccugc    1380
uccucaucug ccuggaaagu ccuccuauuc cagugcccau guuggccucc aguccuuaau    1440
gucaccaugc uuguggccaa ugcauccaaa uaaggauacc ccucagggcu cagcuagaca    1500
uugcaauuuu gcauagcuuu ccaguucccu uugcuugucu ucugacugu cuccccucuc     1560 uaucggggu c acuugcaauu guuaaucaaa gauugaacac ugcguaggag agggagauga    1620
uccagagaca uguggcagca ggcauggcuu cccuuggcc ucucuguaca cugccccagg     1680
acugucauuu uggcaucugc aaaggaauca cuuuagaaag ccagcaccug guugaugugu    1740
auucauacug acauuagauu gaugugcacu gcauuagaaa ugagguagcu gacacagaaa    1800
aaggauguuu ugauaggaau aauuuucuag uaugucuuga aacauguuca ucuggaagua    1860
uuuuccucca aguaauguga gcaugauuuu ucaaggauug uuaacaugcc ugggauuggg    1920
aaagauagga cuaaaguugu gccaaacuau aucaauaaau uccauguuua gcagaaauag    1980
gcagccuauu ggguguuaugu uuauguaaca uagucccagag aacugacaug caggucaaaa   2040
```

```
gucagauacg caaccuccuu aucugcuaac ucuguuauuc uucaaacaca acgugggua    2100 ugucauuuuu ccuuccuucc uuccauuggc agauuguaua uuuauucaca aaacauuaaa    2160
uguccauccu gugccaggua cuaugcagau guugagggau uuggggucug guuagucgug    2220
acuaucuauc cugaaucuaa cagugacuuc auaacuagga gacugaauua gacccuuaag    2280
guauagugug uguugcaaau cacucugcaa uggaaacuuu uauauucagg guagguuugu    2340
gucuuaaacu agguguucua aucaaugua aagacuuuac cauacacgca acuauaguuu    2400
uucuaaaccu ucaucauuuu gugauucuuu gagaaagggc uuuuaggaac uuuauguucu    2460
aaaaaauguu uuuaacaaua auaagauaaa agaaaaaccu gugauucaua ugucccacu     2520 ggcauuacuc agcaggagcc cccagcugcc aaagguuggc agugauccug caaguucaag    2580
ggcucuuucu cccugggau gugcuuugug cuucucuuu acagcuuugu uucugcauca      2640
guucacugcu gcauguuguu uggaauuuau caccuuaaga aaguqucucu guuuuauaua    2700 gaaacacuuu cucacuuaca ggggagaagg aaaugcaggg cacugaucu ggcccucccc     2760 agaacaaucu ggauuucacg gagacagcaa ccagaaguua aaccauguga cuaaaaaugc    2820
aucuggcuac uuuucaugu auguaugaga cagaaacuaa uccuuacuau ccauuaagga     2880
uaccacuuuu cauugcaaag uuugugucaa uaaagucauu aauuuuaaac au           2932

<210> SEQ ID NO 15
<211> LENGTH: 3037
<212> TYPE: RNA
<213> ORGANISM: Homo sapiens

<400> SEQUENCE: 15
gagagggccc ggacuagggg cggcgggcac cgcaggagcu ccgcgcggcu gcagcgcggg     60
cgggagcggg gacgcgaugu cgccgccgcc gccuccuugc gggccggggc ugcgccuccg    120
gggcugagcc gccgccagag ccgacagccg agcagccgcu gggcgcuccc gcggcgcagg    180
aggaugggcu gcggcgggag ccgggcggau gccaucgagc cccgcuacua cgagagcugg    240
acccgggaga cagaauccac cuggcucacc uacaccgacu cggacgcgcc gcccagcgcc    300
gccgcsccgg acagcggccc cgaagcgggc ggccugcacu cggcccauua cccucuugcc    360
uuugcacuug ccuggagaga caacaguuua ggggcucugc ugguucaaga aggacugugc    420
agguagcaug gccacacacc auguacaguu cuggaggcug agaaguccaa gaucaaggca    480
ccaacagauu cagugucuga ugaaggcuug uucucugcuu caaagauggc accucuugcu    540
guguucucac auggcaugcu ggaagaugga cugcccucca auggugugcc ccgaucuaca    600
gccccaggug gaauacccaa cccagagaag aagacgaacu gugagaccca gugcccaaau    660
ccccagagcc ucagcucagg cccucugacc agaaacaga auggccuuca gaccacagag    720
gcuaaaagag augcuaagag aaugccugca aagaaguca ccauuaaugu aacagauagc    780
auccaacaga uggacagaag ucgaagaauc acaaagaacu guguaacua gcagagaguc    840 caagcagaag ggcagaugga cuucuucagu guccuucacg gcacuggauc ccaucaaaga    900
accuugaaga aguggcugcc ccuugcugga ccugaauucu acugagucc uggcaagacu     960 gucuuaccug gcagcaaacu gcugccugau uguugggac cuucugagcc uucuacuuau    1020
caugaaaaug uauuggcaca gugcuuacau auguuaauaa acugcaaaug ugcaguucag    1080
uuugucucuu ugcaacuccu guaauacggu cuggguaaa aguagugagu uaaagcuaca    1140
ggucaguuua ugaaacagaa aaguaggaau gcauuuucug gguaaagag ucacaccuua     1200 gugcuauaac ucuccugccc augauagugu auucuguuuc aggcaagcuu auucuuuccu    1260
```

| | |
|---|---|
| ucuuucauuu uaaauauugu cauuacaaau cuuaccaggu ucacuuaaaa gcuggcuuuc | 1320 |
| auccaacucu aaacccacau auugaaaaaa ucaagguaca ggaaaacucc uuguuauccu | 1380 |
| uguuuccuua gcuugguaug agacagaucg gauccaguuu cccaugcacc aacccacugc | 1440 |
| ccauggcaug ucuuugggag gugucuguga agcagucaua ccugcuccuc aucgccugg | 1500 |
| aaagccucc uauccagug uccauguugg ccuccaguc uuaaugucac caugcuugug | 1560 |
| gccaaugcau ccaaauaagg auaccccuca gggcucagcu agacauugca auuugcaua | 1620 |
| gcuuccagu ucccuuugcu ugucuucuug acugucuucc cucucuaucg ggucacuug | 1680 |
| caauuguuaa ucaaagauug aacacugcgu aggagaggga gaugauccag agacaugugg | 1740 |
| cagcaggcau ggcuuccccu uggccucucu guacacugcc ccaggacugu cauuuuggca | 1800 |
| ucugcaaagg aaucacuuua gaaagccagc accgguuga uguguauuca uacugacauu | 1860 |
| agauugaugu gcacugcauu agaaaugagg uagcugacac agaaaaagga guuuugaua | 1920 |
| ggaauaauuu ucuaguaugu cuugaaacau guucaucugg aaguauuuuc cuccaaagua | 1980 |
| auguagcaug auuuuucaag gauuguuaac augccuggga uugggaaaga uaggacuaaa | 2040 |
| guugugccaa acuauaucaa uaaauuccau guuuagcaga aauaggcagc cuauggugu | 2100 |
| uauguuuaug uaacauaguc cagagaacug acaugcaggu caaaagucag auacgcaacc | 2160 |
| uccuuaucug cuaacucugu uauucuucaa acacaacgug gguaguguca uuuuuccuuc | 2220 |
| cuuccuucca uuggcagauu guauauuuau ucacaaaaca uuaaaugucc auccugugcc | 2280 |
| agguacuaug cagauguuga gggauuuggg gucugguuag ucgugacuau cuauccugaa | 2340 |
| ucuaacagug acuucauaac uaggagacug aauuagaccc uuaagguaua gugugugu | 2400 |
| caaaucacuc ugcaauggaa acuuuuauau ucagggagg uuugugucuu aaacuaggug | 2460 |
| uucuaaucaa uguacaagac uuuaccauac acgcaacuau aguuuucua aaccuucauc | 2520 |
| auuuugugau ucuuugagaa agggcuuuua ggaacuuuau guucuaaaaa auguuuaaaa | 2580 |
| caauaauaag auaaaagaaa aaccugugau ucauaugucc ccacuggcau uacucagcag | 2640 |
| gagccccag cugccaaagg uuggcaguga ccugcaagu ucaagggcuc uuucuccccug | 2700 |
| gggaugugcu uugugggcuuc ucuuuacagc uuuguuucug caucaguuca cugcugcaug | 2760 |
| uuguuuggaa uuuaucaccu uaagaaagug ucucuguuuu auauagaaac acuuucucac | 2820 |
| uuacagggga gaaggaaaug cagggcacau gaucuggccc uccccagaac aaucuggauu | 2880 |
| ucacggagac agcaaccaga aguuaaacca ugugacuaaa aaugcaucug gcuacuuuuu | 2940 |
| cauguaugua ugagacagaa acuaauccuu acuauccau uaggauacca cuuuucauug | 3000 |
| caaaguuugu gucaauaaag ucauuaauuu uaaacau | 3037 |

<210> SEQ ID NO 16
<211> LENGTH: 3079
<212> TYPE: RNA
<213> ORGANISM: Homo sapiens

<400> SEQUENCE: 16

| | |
|---|---|
| gagagggccc ggacuagggg cggcgggcac cgcaggagcu ccgcgcggcu gcagcgcggg | 60 |
| cgggagcggg gacgcgaugu cgccgccgcc gccuccuugc gggccggggc ugcgccuccg | 120 |
| gggcugagcc gccgccagag ccgacagccg agcagccgcu gggcgcuccc gcggcgcagg | 180 |
| aggaugggcu gcggcgggag ccgggcggau gccaucgagc cccgcuacua cgagagcugg | 240 |
| acccggggaga cagaauccac cuggcucacc uacaccgacu cggacgcgcc gcccagcgcc | 300 |

```
gccgcgccgg acagcggccc cgaagcgggc ggccugcacu cggcccauua cccucuugcc    360
uuugcacuug ccuggagaga caacaguuua ggggcucugc ugguucaaga aggacugugc    420
agguagcaug gccacacacc auguacaggu ucuggugcuu aggaguggac aucuuuggga    480
ccgagggnua uucugccuuc cuaccaugnc accagaguug ugcuaauaca cagagagcuu    540
caggggauga gaucugccau ucauugagca ccuucgugc ggcagacagu guuaggcaug     600
cuggaagaug gacugcccuc caauggugug ccccgaucua cagccccagg uggaauaccc    660
aacccagaga agaagacgaa cugugagacc cagugcccaa auccccagag ccucagcuca    720
ggcccucuga cccagaaaca gaauggccuu cagaccacag aggcuaaaag agaugcuaag    780
agaaugccug caaagaagu caccauuaau guaacagaua gcauccaaca gauggacaga     840
agucgaagaa ucacaaagaa cugugucaac uagcagagag uccaagcaga agggcagaug    900
gacuucuuca guguccuuca cggcacugga ucccaucaaa gaaccuugaa gaaguggcug    960 cccuugcug gaccugaauu cuacugaguc ccuggcaaga cugucuuacc uggcagcaaa    1020
cugcugccug auuuguuggg accuucugag ccuucuacuu aucauguaaa uguauuggca    1080
cagugcuuac auauguuaau aaacugcaaa ugugcaguuc aguuugucuc uuugcaacuc    1140 cguaauacg gucggugua aaaguaguga guuaaagcua caggucaguu augaaacag      1200 aaaguagga augcauuuc uggugaaag agucacaccu uagugcuaua acucuccugc      1260
ccaugauagu guauucuguu ucaggcaagc uuauucuuuc cuucuuucau uuuaaauauu    1320
gucauuacaa aucuuaccag guucacuuaa aagcuggcuu ucauccaacu cuaaacccac    1380
auauugaaaa aaucaaggua caggaaaacu ccuuguuauc cuuguuuccu uagcuuggua    1440
ugagacagau cggauccagu uuccacauca ccaacccacu gcccauggca ugucuuuggg    1500
aggugucugu gaagcaguca uaccugcucc ucaucugccu ggaaaguccu ccuauuccag    1560
uguccauguu ggccuccagu ccuuaaaguc accaugcuug uggccaaugc auccaaauaa    1620
ggauaccccu caggggcucag cuagacauug caauuuugca uagcuuucca guucccuuug    1680
cuugucuucu ugacugucuu cccucucuau cggggucacu ugcaauuguu aaucaaagau    1740
ugaacacugc guaggagagg gagaugauce agagacaugu ggcagcaggc auggcuuccc    1800
cuuggccucu cuguacacug ccccaggacu gucauuuugg caucugcaaa ggaaucacuu    1860
uagaaagcca gcaccugguu gauguguauu cauacugaca uuagauugau gugcacugca    1920 uuagaauga gguagcugac acagaaaaag gauguuuuga uaggaauauau uuucuaguau    1980 gucuugaaac auguucaucu ggaaguauuu uccuccaaag uaauguagca ugauuuuuca    2040
aggauuguua acaugccugg gauugggaaa gauaggacua aaguugugcc aaacuauauc    2100
aauaaauucc auguuuagca gaaauaggca gccauugguu guuauguuua guaacauag    2160 uccagagaac ugacaugcag gucaaaaguc agauacgcaa ccuccuuauc ugcuaacucu    2220
guuauucuuc aaacacaacg ugggaguagugu cauuuuccu ccuuccuuc cauuggcaga    2280 uuguauauuu auucacaaaa cauuaaaugu ccauccugug ccagguacua ugcagauguu    2340
gagggauuug gggucugguu agucgugacu aucuauccug aaucaaacag ugacuucaua    2400
acuaggagac ugaauuagac ccuuaaggua uaguguguguu ugcaaaucac ucugcaaugg    2460
aaacuuuuau auucaggguu gguugugugc uuaaacuagg guucuaauc aauguacaag    2520 acuuuaccau acacgcaacu auaguuuuuc uaaaccuuca ucauuugug auucuuugag    2580 aaagggcuuu uaggaacuuu auguucaaaa aauguuuuuu aacaauaaua agauaaaaga    2640 aaaccugug auucauaugu ccccacuggc auuacucagc aggagccccc agcugccaaa    2700
```

| | | |
|---|---|---|
| gguuggcagu gauccugcaa guucaagggc ucuuucuccc ugggaugug cuuuguggcu | 2760 |
| ucucuuuaca gcuuuguuuc ugcaucaguu cacugcugca uguuguuugg aauuuaucac | 2820 |
| cuuaagaaag ugucucuguu uuauauagaa acacuuucuc acuuacaggg gagaaggaaa | 2880 |
| ugcagggcac augaucuggc ccuccccaga acaaucugga uucacggag acagcaacca | 2940 |
| gaaguuaaac caugugacua aaaaugcauc uggcuacuuu uucauguaug uaugagacag | 3000 |
| aaacuaaucc uuacuauccu auuaggauac cacuuucau ugcaaaguuu gugucaauaa | 3060 |
| agucauuaau uuuaaacau | 3079 |

<210> SEQ ID NO 17
<211> LENGTH: 145
<212> TYPE: PRT
<213> ORGANISM: Homo sapiens

<400> SEQUENCE: 17

```
Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Pro Pro Ser Ala Ala Ala Pro Asp Ser Gly Pro Glu Ala
        35                  40                  45

Gly Gly Leu His Ser Gly Met Leu Glu Asp Gly Leu Pro Ser Asn Gly
    50                  55                  60

Val Pro Arg Ser Thr Ala Pro Gly Gly Ile Pro Asn Pro Glu Lys Lys
65                  70                  75                  80

Thr Asn Cys Glu Thr Gln Cys Pro Asn Pro Gln Ser Leu Ser Ser Gly
                85                  90                  95

Pro Leu Thr Gln Lys Gln Asn Gly Leu Gln Thr Thr Glu Ala Lys Arg
            100                 105                 110

Asp Ala Lys Arg Met Pro Ala Lys Glu Val Thr Ile Asn Val Thr Asp
        115                 120                 125

Ser Ile Gln Gln Met Asp Arg Ser Arg Arg Ile Thr Lys Asn Cys Val
    130                 135                 140

Asn
145
```

<210> SEQ ID NO 18
<211> LENGTH: 54
<212> TYPE: PRT
<213> ORGANISM: Homo sapiens

<400> SEQUENCE: 18

```
Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Pro Pro Ser Ala Ala Ala Pro Asp Ser Gly Pro Glu Ala
        35                  40                  45

Gly Gly Leu His Ser Gly
    50
```

<210> SEQ ID NO 19
<211> LENGTH: 180
<212> TYPE: PRT
<213> ORGANISM: Homo sapiens -continued

```
<400> SEQUENCE: 19

Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Pro Pro Ser Ala Ala Pro Asp Ser Gly Pro Glu Ala
        35                  40                  45

Gly Gly Leu His Ser Val Leu Glu Ala Glu Lys Ser Lys Ile Lys Ala
    50                  55                  60

Pro Thr Asp Ser Val Ser Asp Glu Gly Leu Phe Ser Ala Ser Lys Met
65                  70                  75                  80

Ala Pro Leu Ala Val Phe Ser His Gly Met Leu Glu Asp Gly Leu Pro
                85                  90                  95

Ser Asn Gly Val Pro Arg Ser Thr Ala Pro Gly Gly Ile Pro Asn Pro
            100                 105                 110

Glu Lys Lys Thr Asn Cys Glu Thr Gln Cys Pro Asn Pro Gln Ser Leu
        115                 120                 125

Ser Ser Gly Pro Leu Thr Gln Lys Gln Asn Gly Leu Gln Thr Thr Glu
130                 135                 140

Ala Lys Arg Asp Ala Lys Arg Met Pro Ala Lys Glu Val Thr Ile Asn
145                 150                 155                 160

Val Thr Asp Ser Ile Gln Gln Met Asp Arg Ser Arg Ile Thr Lys
                165                 170                 175

Asn Cys Val Asn
            180

<210> SEQ ID NO 20
<211> LENGTH: 73
<212> TYPE: PRT
<213> ORGANISM: Homo sapiens

<400> SEQUENCE: 20

Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Pro Pro Ser Ala Ala Ala Pro Asp Ser Gly Pro Glu Ala
        35                  40                  45

Gly Gly Leu His Ser Gly Cys Leu Glu Glu His Tyr His Leu Thr Ala
    50                  55                  60

Leu Gln Lys Val Gly His Pro Asn His
65                  70

<210> SEQ ID NO 21
<211> LENGTH: 149
<212> TYPE: PRT
<213> ORGANISM: Homo sapiens

<400> SEQUENCE: 21

Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Pro Pro Ser Ala Ala Ala Pro Asp Ser Gly Pro Glu Ala
        35                  40                  45

Gly Gly Leu His Ser Val Leu Glu Ala Glu Lys Ser Lys Ile Lys Ala
```

```
                50                  55                  60
Pro Thr Asp Ser Val Ser Asp Glu Gly Leu Phe Ser Ala Ser Lys Met
 65                  70                  75                  80

Ala Pro Leu Ala Val Phe Ser His Gly Met Leu Glu Asp Gly Leu Pro
                 85                  90                  95

Ser Asn Gly Val Pro Arg Ser Thr Ala Pro Gly Gly Ile Pro Asn Pro
            100                 105                 110

Glu Lys Lys Thr Asn Cys Glu Thr Gln Cys Pro Asn Pro Gln Ser Leu
        115                 120                 125

Ser Ser Gly Pro Leu Thr Gln Lys Gln Asn Gly Leu Gln Thr Thr Glu
    130                 135                 140

Val Leu Leu Pro Ser
145

<210> SEQ ID NO 22
<211> LENGTH: 80
<212> TYPE: PRT
<213> ORGANISM: Homo sapiens

<400> SEQUENCE: 22

Met Gly Cys Gly Gly Ser Arg Ala Asp Ala Ile Glu Pro Arg Tyr Tyr
 1               5                  10                  15

Glu Ser Trp Thr Arg Glu Thr Glu Ser Thr Trp Leu Thr Tyr Thr Asp
                 20                  25                  30

Ser Asp Ala Pro Pro Ser Ala Ala Ala Pro Asp Ser Gly Pro Glu Ala
             35                  40                  45

Gly Gly Leu His Ser Ala His Tyr Pro Leu Ala Phe Ala Leu Ala Trp
     50                  55                  60

Arg Asp Asn Ser Leu Gly Ala Leu Leu Val Gln Glu Gly Leu Cys Arg
 65                  70                  75                  80

<210> SEQ ID NO 23
<211> LENGTH: 20
<212> TYPE: DNA
<213> ORGANISM: Homo sapiens

<400> SEQUENCE: 23
catctgttgg atgctatctg                                              20

<210> SEQ ID NO 24
<211> LENGTH: 20
<212> TYPE: DNA
<213> ORGANISM: Homo sapiens

<400> SEQUENCE: 24
tggactctct gctagttgac                                              20

<210> SEQ ID NO 25
<211> LENGTH: 20
<212> TYPE: DNA
<213> ORGANISM: Homo sapiens

<400> SEQUENCE: 25
tcggtgtagt tgatcttctc                                              20

<210> SEQ ID NO 26
<211> LENGTH: 20
<212> TYPE: DNA
<213> ORGANISM: Homo sapiens
```

```
<400> SEQUENCE: 26
acccagagaa gaagacgaac                                               20

<210> SEQ ID NO 27
<211> LENGTH: 20
<212> TYPE: DNA
<213> ORGANISM: Homo sapiens

<400> SEQUENCE: 27
agaaacagaa tggccttcag                                               20

<210> SEQ ID NO 28
<211> LENGTH: 20
<212> TYPE: DNA
<213> ORGANISM: Homo sapiens

<400> SEQUENCE: 28
gccctctgac ccagaaacag                                               20

<210> SEQ ID NO 29
<211> LENGTH: 23
<212> TYPE: DNA
<213> ORGANISM: Homo sapiens

<400> SEQUENCE: 29
cttttgcagg cattctctta gca                                           23

<210> SEQ ID NO 30
<211> LENGTH: 20
<212> TYPE: DNA
<213> ORGANISM: Homo sapiens

<400> SEQUENCE: 30
tcttcgatgc caacaaggac                                               20

<210> SEQ ID NO 31
<211> LENGTH: 19
<212> TYPE: DNA
<213> ORGANISM: Homo sapiens

<400> SEQUENCE: 31
gcatcacgtc ctccgtcac                                                19

<210> SEQ ID NO 32
<211> LENGTH: 25
<212> TYPE: DNA
<213> ORGANISM: Homo sapiens

<400> SEQUENCE: 32
caggcattct cttagcatct ctttt                                         25

<210> SEQ ID NO 33
<211> LENGTH: 30
<212> TYPE: DNA
<213> ORGANISM: Homo sapiens

<400> SEQUENCE: 33
ctcttttagc ctctgtggtc tgaaggccat                                    30

<210> SEQ ID NO 34
<211> LENGTH: 24
<212> TYPE: DNA
<213> ORGANISM: Homo sapiens
```

```
<400> SEQUENCE: 34
ttcagcttga ccctcaacac caac                                          24

<210> SEQ ID NO 35
<211> LENGTH: 18
<212> TYPE: PRT
<213> ORGANISM: Homo sapiens

<400> SEQUENCE: 35

Asp Ala Ile Glu Pro Arg Tyr Tyr Glu Ser Trp Thr Arg Glu Thr Glu
1               5                   10                  15

Ser Thr

<210> SEQ ID NO 36
<211> LENGTH: 14
<212> TYPE: PRT
<213> ORGANISM: Homo sapiens

<400> SEQUENCE: 36

Asp Ser Ile Gln Gln Met Asp Arg Ser Arg Arg Ile Thr Lys
1               5                   10

<210> SEQ ID NO 37
<211> LENGTH: 25
<212> TYPE: PRT
<213> ORGANISM: Homo sapiens

<400> SEQUENCE: 37

Arg Ala Asp Ala Ile Glu Pro Arg Tyr Tyr Glu Ser Trp Thr Arg Glu
1               5                   10                  15

Thr Glu Ser Thr Trp Leu Thr Tyr Thr
            20                  25

<210> SEQ ID NO 38
<211> LENGTH: 34
<212> TYPE: DNA
<213> ORGANISM: Homo sapiens

<400> SEQUENCE: 38
gtgcggtacc aagcttccgc ggcgcaggag gatg                               34

<210> SEQ ID NO 39
<211> LENGTH: 32
<212> TYPE: DNA
<213> ORGANISM: Homo sapiens

<400> SEQUENCE: 39
cggggtaccg ttgacacagt tctttgtgat tc                                 32
```